(12) United States Patent
Mehrotra et al.

(10) Patent No.: US 11,883,430 B2
(45) Date of Patent: Jan. 30, 2024

(54) CD38-NAD+ REGULATED METABOLIC AXIS IN ANTI-TUMOR IMMUNOTHERAPY

(71) Applicant: MUSC FOUNDATION FOR RESEARCH DEVELOPMENT, Charleston, SC (US)

(72) Inventors: Shikhar Mehrotra, Mount Pleasant, SC (US); Shilpak Chatterjee, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 477 days.

(21) Appl. No.: 16/347,743

(22) PCT Filed: Nov. 8, 2017

(86) PCT No.: PCT/US2017/060537
§ 371 (c)(1),
(2) Date: May 6, 2019

(87) PCT Pub. No.: WO2018/089423
PCT Pub. Date: May 17, 2018

(65) Prior Publication Data
US 2019/0255111 A1 Aug. 22, 2019

Related U.S. Application Data

(60) Provisional application No. 62/419,612, filed on Nov. 9, 2016.

(51) Int. Cl.
| | |
|---|---|
| *A61K 35/17* | (2015.01) |
| *A61P 35/00* | (2006.01) |
| *A61K 35/26* | (2015.01) |
| *C07K 16/24* | (2006.01) |
| *C12N 5/0783* | (2010.01) |
| *A61K 45/06* | (2006.01) |
| *A61K 9/00* | (2006.01) |
| *C07K 16/28* | (2006.01) |
| *C07K 16/30* | (2006.01) |
| *A61K 39/395* | (2006.01) |

(52) U.S. Cl.
CPC ............ *A61K 35/17* (2013.01); *A61K 9/0019* (2013.01); *A61K 35/26* (2013.01); *A61K 39/39558* (2013.01); *A61K 45/06* (2013.01); *A61P 35/00* (2018.01); *C07K 16/249* (2013.01); *C07K 16/2896* (2013.01); *C07K 16/30* (2013.01); *C12N 5/0636* (2013.01); *C12N 5/0638* (2013.01); *C07K 2317/55* (2013.01); *C07K 2317/76* (2013.01); *C12N 2501/15* (2013.01); *C12N 2501/2301* (2013.01); *C12N 2501/2306* (2013.01); *C12N 2501/2312* (2013.01); *C12N 2501/2323* (2013.01); *C12N 2501/599* (2013.01)

(58) Field of Classification Search
CPC ...... A61K 35/17; A61K 35/26; C07K 16/249; C12N 2501/2306; C12N 2501/2323; C12N 2501/2312; C12N 2501/2301
See application file for complete search history.

(56) References Cited

U.S. PATENT DOCUMENTS

| | | |
|---|---|---|
| 2010/0323383 A1 | 12/2010 | Manel et al. |
| 2013/0209355 A1 | 8/2013 | De Weers et al. |
| 2015/0361396 A1 | 12/2015 | Regev et al. |

FOREIGN PATENT DOCUMENTS

| | | |
|---|---|---|
| WO | WO 2014/169011 | 10/2014 |
| WO | WO 2016/011210 | 1/2016 |
| WO | WO 2016/126608 | 8/2016 |

OTHER PUBLICATIONS

Lexberg et al. IFN-gamma and IL-12 synergize to convert in vivo generated .Th17 into Th1/Th17 cells. Eur. J. Immunol. 2010. 40: 3017-3027 (Year: 2010).*
Chatterjee et al. Reducing CD73 Expression by IL1b-Programmed Th 17 Cells Improves Immunotherapeutic Control of Tumors. Cancer Res; 74(21) Nov. 1, 2014. *of record* (Year: 2014).*
Gerosa et al. Differential regulation of interleukin 12 and interleukin 23 production in human dendritic cells. J. Exp. Med. vol. 205 No. 6 1447-1461. 2008 (Year: 2008).*
Muranski et al. Tumor-specific Th17-polarized cells eradicate large established melanoma. Blood, Jul. 15, 2008 vol. 112, No. 2. *Of Record* (Year: 2008).*
Aksoy et al., "Regulation of intracellular levels of NAD: a novel role for CD38," *Biochem. Bhiophys. Res. Commun.*, 345(4):1386-92, 2006.
Aksoy et al., "Regulation of SIRT 1 mediated NAD dependent deacetylation: a novel role for the multifunctional enzyme CD38," *Biochem. Biophys. Res. Commun.*, 349(1):353-9, 2006.
Boniface et al., "Human Th17 cells comprise heterogeneous subsets including IFN-gamma-producing cells with distinct properties from the Th1 lineage," *J. Immunol.*, 185(1):679-87, 2010.
Bruzzone et al., "Catastrophic NAD+ depletion in activated T lymphocytes through Nampt inhibition reduces demyelination and disability in EAE," *PLoS One*, 4(11):e7897, 2009.
Chalmin et ali., "Stat3 and Gfi-1 transcription factors control Th17 cell immunosuppressive activity via the regulation of ectonucleotidase expression," *Immunity*, 36:362-73, 2012.

(Continued)

*Primary Examiner* — Amy E Juedes
*Assistant Examiner* — Brian Hartnett
(74) *Attorney, Agent, or Firm* — Parker Highlander PLLC

(57) ABSTRACT

The present disclosure provides methods of producing hybrid Th1/Th17 cells. Also provided herein are methods of treating cancer comprising targeting the CD38-mediated metabolic axis.

14 Claims, 14 Drawing Sheets
Specification includes a Sequence Listing.

(56) References Cited

OTHER PUBLICATIONS

Chang et al., "Posttranscriptional control of T cell effector function by aerobic glycolysis," *Cell*, 153(6):1239-1251, 2013.

Chapuis et al., "Transferred WT1-reactive CD8+ T cells can mediate antileukemic activity and persist in post-transplant patients," *Science Translational Medicine*, 5(174):174ra127, 2013.

Chatterjee et al., "Reducing CD73 expression by IL1β-Programmed Th17 cells improves immunotherapeutic control of tumors," *Cancer Research*, 74(21):6048-6059, 2014.

Chatterjee et al., "Cd38-NAD$^+$ Axis Regulates Immunotherapeutic Anti-Tumor T Cell Response," *Cell Metabolism*, 27(1):85-100, 2018.

Chini, "CD38 as a regulator of cellular NAD: a novel potential pharmacological target for metabolic conditions," *Curr. Pharm. Des.*, 15(1):57-63, 2009.

Duhen et al., "IL-1β promotes the differentiation of polyfunctional human CCR6+CXCR3+ Th1/17 cells that are specific for pathogenic and commensal microbes," *The Journal of Immunology*, 193(1):120-129, 2014.

Extended European Search Report issued in European Patent Application No. 17869121.8, dated Aug. 3, 2020.

Flores-Borja et al., "CD19+CD24hiCD38hi B cells regulatory T cells while limiting TH1 and TH17 differentiation," *Sci. Transl. Med.*, 5(173):173ra23, pp. 1-13, 2013.

Klebanoff et al., "IL-15 enhances the in vivo antitumor activity of tumor-reactive CD8+ T cells," *Proceedings of the National Academy of Sciences of the United States of America*, 101(7):1969-1974, 2004.

Klysz et al., "Glutamine-dependant α-ketoglutarate production regulates the balance between T helper 1 cell and regulatory T cell generation," *Sci Signal*, 8:ra97, 2015.

Lexberg et al., "IFN-γ and IL-12 synergize to convert in vivo generated Th17 into Th1/Th17 cells," *Eur. J. Immunol.*, 40(11):3017-27, 2010.

Lu et al., "Th9 cells promote antitumor immune responses in vivo," *The Journal of Clinical Investigation*, 122:4160-4171, 2012.

Mihara et al., "Synergistic and persistent effect of T-cell immunotherapy with anti-CD19 or anti-CD38 chimeric receptor in conjugation with rituximab on B-cell non-Hodgkin lymphoma," *British Journal of Haematology*, 151(1):37-46, 2010.

Morandi et al., "A non-canonical adenosinergic pathway led by CD38 in human melanoma cells induces suppression of T cell proliferation," *Oncotarget*, 6(28):25602-18, 2015.

Moroz et al., "IL-21 enhances and sustains CD8+ T cell responses to achieve durable tumor immunity: comparative evaluation of IL-2, IL-15, and IL-21," *Journal of Immunology*, 173:900-909, 2004.

Muranski et al., "Tumor-specific Th17-polarized cells eradicate large established melanoma," *Blood*, 112(2):362-73, 2008.

PCT International Search Report and Written Opinion issued in International Application No. PCT/US2017/060537, dated Mar. 13, 2018.

Rao et al., "Transcription factor Foxo1 represses T-bet mediated effector functions and promotes memory CD8+ T cell differentiation," *Immunity*, 36(3):374-387, 2012.

Scalzo-Inguanti et al., "CD38 identifies a hypo-proliferative IL-13-secreting CD4+ T-cell subset that does not fit into existing naive and memory phenotype paradigms," *European Journal of Immunology*, 41(5):1298-1308, 2011.

Scharping et al., "The Tumor Microenvironment Represses T Cell Mitochondrial Biogenesis to Drive Intratumoral T Cell Metabolic Insufficiency and Dysfunction," *Immunity*, 45(2):374-388, 2016.

Sukumar et al., "Inhibiting glycolytic metabolism enhances CD8+ T cell memory and antitumor function," *J. Clin. Invest.*, 123(10):4479-4488, 2013.

Sundrud et al., "Identity crisis of Th17 cells: many forms, many functions, many questions," *Seminars in Immunology*, 25(4):263-272, 2013.

Tsung et al., "IL-12 induces T helper 1-directed antitumor response," *Journal of Immunology*, 158:3359-3365, 1997.

Tullius et al., "NAD+ protects against EAE by regulating CD4+ T-cell differentiation," *Nat. Commun.*, 5:5101, 2014.

Yadong Hu et al., "Overexpression of CD38 decreases cellular NAD levels and alters the expression of proteins involved in energy metabolism and antioxidant defense," *J. Proteome Res.*, 13(2):786-795, 2014.

Yu et al., "Adoptive transfer of Tc1 or Tc17 cells elicits antitumor immunity against established melanoma through distinct mechanisms," *J. Immunol.*, 190(4):1873-81, 2013.

Zhang and Kraus, "SIRT1-dependant regulation of chromatin and transcription. linking NAD$^+$ metabolism and signaling to the control of cellular functions," *Biochim. Biophys. Acta*, 1804:1666-1675, 2010.

Gerosa et al., "Differential regulation of interleukin 12 and interleukin 23 production in human dendritic cells", *The Journal of Experimental Medicine*, 205(6): 1447-1461, 2008.

Office Communication issued in correspondence European Application No. 17869121.8 dated Jul. 29, 2022.

* cited by examiner

CD38-NAD+ REGULATED METABOLIC AXIS IN ANTI-TUMOR IMMUNOTHERAPY

This application is a national phase application under 35 U.S.C. § 371 of International Application No. PCT/US2017/060537, filed Nov. 8, 2017, which claims the benefit of U.S. Provisional Patent Application No. 62/419,612, filed Nov. 9, 2016, the entirety of each of which is incorporated herein by reference.

Pursuant to 37 C.F.R. 1.821(c), a sequence listing is submitted herewith as an ASCII compliant text file named "MESCP0102US ST25.txt", created on May 3, 2019 and having a size of ~18 kilobytes. The content of the aforementioned file is hereby incorporated by reference in its entirety.

BACKGROUND OF THE INVENTION

The invention was made with government support under grant numbers CA138930, CA137725 and CA154778 awarded by the National Institutes of Health. The government has certain rights in the invention.

1. Field of the Invention

The present invention relates generally to the fields of molecular biology and medicine. More particularly, it concerns targeting the CD38-mediated metabolic axis for cancer immunotherapy.

2. Description of Related Art

Adoptive T cell therapy (ACT) is a powerful strategy for controlling cancer (Rosenberg and Restifo, 2015). However, elimination of established tumor is hampered either due to loss of T cell effector function or its survival (Crompton et al., 2014). Therefore, strategies to increase persistence and sustain effector function of the anti-tumor T cells in the tumor-bearing host are of immense importance. Several strategies involving duration of expansion (Klebanoff et al., 2011), or using different cytokines (e.g., IL2, IL15, IL21) (Chapuis et al., 2013; Klebanoff et al., 2004; Moroz et al., 2004), and employing different helper T (Th) or cytotoxic T (Tc) subsets programed ex vivo (e.g., Th1 or Tc1, Th9 or Tc9, Th17 or Tc17) (Emtage et al., 2003; Lu et al., 2012; Muranski et al., 2008) have been tested to improve the efficacy of ACT. While each one of these strategies results in a unique effector signature and may show an incremental improvement in tumor control (Lu et al., 2012; Muranski et al., 2008; Tsung et al., 1997), efforts to incorporate optimal anti-tumor attributes of these strategies into one effector population have not yet been successful.

Different cytokine cues direct naive CD4 T cells to acquire distinct functional and survival traits that differentially affect their anti-tumor response. For instance, Th1 cell secretes IFNγ, but due to their poor survivability are less efficacious than Th17 cells with "stem cell-like" characteristics in controlling tumor. Although Th17 cells have survival advantage in the tumor-bearing host, the anti-tumor property is dependent on their ability to secrete IFNγ. Thus, defining conditions that would preserve "effector cytokine function" of Th1/Tc1 cells along with the "stem cell-like phenotype" of the Th17/Tc17 cells would be advantageous for ACT.

SUMMARY OF THE INVENTION

A first embodiment of the present disclosure provides an ex vivo method for producing hybrid Th1/Th17 cells comprising obtaining a starting population of T cells, and culturing the starting population of T cells in the presence of IL6, IL1β, IL23, TGFβ and IL12, thereby differentiating the starting population of T cells to hybrid Th1/Th17 cells. In particular aspects, the initial culture does not comprise IL2, such as essentially no exogenous IL-2. In some aspects, the culturing is for 2 to 5 days, such as 2-3 or 3-4 days, particularly 3 or 4 days. In certain aspects, the culture further comprises anti-IL4, anti-IFNα and/or anti-IFNγ.

In some aspects, the TGFβ is present at a concentration of about 0.1 to 0.5 ng/mL (e.g., 0.1-0.2, 0.2-0.3, 0.3-0.4, or 0.4-0.5 ng/mL, particularly about 0.1, 0.2, 0.3, 0.4, or 0.5 ng/mL). In certain aspects, the IL1β, IL23, IL6, and/or IL12 are present at a concentration of about 5 to 30 ng/mL (e.g., about 10, 15, 20, 25, or 30 ng/mL). In particular aspects, IL1β and/or IL23 is present at a concentration of about 10-30 ng/mL (e.g., about 15, 20, or 25 ng/mL). In some aspects, IL6 is present at a concentration of about 15-35 ng/mL (e.g., about 20, 25, or 30 ng/mL). In some aspects, IL12 is present at a concentration of about 5-15 ng/mL (e.g., about 8, 10, or 12 ng/mL). IL4 may be present at a concentration of about 5-15 μg/mL (e.g., about 8, 10, or 12 μg/mL). IFNγ may be present at a concentration of about 1-10 μg/mL (e.g., about 3, 5, or 7 μg/mL).

In certain aspects, the culture further comprises anti-CD3 and/or anti-CD28. In some aspects, the anti-CD3 and anti-CD28 are bound to a surface, such as plate-bound anti-CD3 and/or anti-CD28. Anti-CD3 and/or anti-CD28 may be present at a concentration of about 1-10 μg/mL (e.g., about 3, 5, or 7 μg/mL).

In some aspects, the starting population of T cells are CD4$^+$ T cells. The starting population of T cells may comprise tumor infiltrating lymphocytes (TILs) or a mixed population of T cells, such as CD4$^+$ and CD8$^+$ T cells. In particular aspects, the T cells, such as CD4$^+$ T cells, are isolated from splenocytes. In some aspects, the starting population of T cells are human T cells. In certain aspects, the isolation is performed by magnetic-bead sorting or fluorescence-activated cell sorting.

In certain aspects, the hybrid Th1/Th17 cells have an effector and sternness phenotype. In some aspects, the hybrid cells have increased NAD$^+$ levels as compared to Th17 cells. In particular aspects, the increase in NAD$^+$ levels is at least 10-fold, such as at least 20-fold, 25-fold, or 30-fold as compared to NAD$^+$ levels in Th17 cells. In some aspects, the hybrid Th1/Th17 cells have reduced expression of CD38 as compared to Th1 or Th17 cells. In certain aspects, the hybrid Th1/Th17 cells have at least two-fold higher Sirt1 activity as compared to Th17 cells. In particular aspects, the hybrid Th1/Th17 cells co-express elevated levels of IFNγ and IL17. In some aspects, the hybrid Th1/Th17 cells express transcription factors T-bet, RORγ, and/or IRF-4. In certain aspects, the hybrid Th1/Th17 cells express chemokine receptors CXCR3 and/or CCR6. In some aspects, the hybrid Th1/Th17 cells express effector genes GzmB, Tbx21, and/or GM-CSF. In certain aspects, the hybrid Th1/Th17 cells express sternness genes IL22, IL23R, TCF7, BCL6, and/or β-catenin. In particular aspects, the hybrid Th1/Th17 cells exhibit increased anti-tumor activity as compared to Th1 or Th17 cells.

Further provided herein is a pharmaceutical composition comprising hybrid Th1/Th17 cells with low or no expression of CD38 and a pharmaceutical carrier. In some aspects, the hybrid Th1/Th17 cells are produced according to the above embodiments. In other aspects, the T cells with decreased or no expression of CD38 are produced by activating T cells in the presence of an anti-CD38 antibody. In some aspects, the T cells with decreased or no expression of CD38 are produced by contacting the T cells with siRNA or shRNA. In other aspects, the T cells with decreased or no expression of CD38 are produced by genetically modifying the T cells. In particular aspects, genetically modifying comprises the use of TALENs or the CRISPR/Cas9 system.

In a further embodiment, there is provided a composition comprising an effective amount of hybrid Th1/Th17 cells with low or no expression of CD38 for the treatment of cancer in a subject.

In another embodiment, there is provided a method of treating cancer in a subject comprising administering (e.g., performing adoptive cell transfer (ACT)) T cells with low or no expression of CD38, and/or administering anti-CD38 antibody in combination with the T cells to the subject. In one embodiments, there is provided a method of treating cancer in a subject comprising administering an effective amount of T cells with low or essentially no expression of CD38 to the subject. In another embodiment, there is provided a method of treating cancer in a subject comprising administering an anti-CD38 antibody in combination with T cells to the subject.

In some aspects of the present embodiments, the cancer is lung cancer, melanoma, or prostate cancer. In particular aspects, the subject is human. In certain aspects, the T cells administered in combination with anti-CD38 antibody are unprogrammed Th0 cells.

In certain aspects of the present embodiments, the hybrid Th1/Th17 cells have an effector and stemness phenotype. In some aspects, the hybrid cells have increased NAD$^+$ levels as compared to Th17 cells. In particular aspects, the increase in NAD$^+$ levels is at least 10-fold, such as at least 20-fold, 25-fold, or 30-fold as compared to NAD$^+$ levels in Th17 cells. In some aspects, the hybrid Th1/Th17 cells have reduced expression of CD38 as compared to Th1 or Th17 cells. In certain aspects, the hybrid Th1/Th17 cells have at least two-fold higher Sirt1 activity as compared to Th17 cells. In particular aspects, the hybrid Th1/Th17 cells co-express elevated levels of IFNγ and IL17. In some aspects, the hybrid Th1/Th17 cells express transcription factors T-bet, RORγ, and/or IRF-4. In certain aspects, the hybrid Th1/Th17 cells express chemokine receptors CXCR3 and/or CCR6. In some aspects, the hybrid Th1/Th17 cells express effector genes GzmB, Tbx21, and/or GM-CSF. In certain aspects, the hybrid Th1/Th17 cells express stemness genes IL22, IL23R, TCF7, BCL6, and/or β-catenin. In particular aspects, the hybrid Th1/Th17 cells exhibit increased anti-tumor activity as compared to Th1 or Th17 cells.

In some aspects, the T cells with decreased or no expression of CD38 are the hybrid Th1/Th17 cells produced according to the embodiments (e.g., culturing the T cells in the presence of IL6, IL1β, IL23, TGFβ and IL-12). In other aspects, the T cells with decreased or no expression of CD38 are produced by activating T cells in the presence of an anti-CD38 antibody. In some aspects, the T cells with decreased or no expression of CD38 are produced by contacting the T cells with siRNA or shRNA. In other aspects, the T cells with decreased or no expression of CD38 are produced by genetically modifying the T cells. In particular aspects, genetically modifying comprises the use of TALENs or the CRISPR/Cas9 system.

In some aspects, the T cells are antigen-specific T cells. In certain aspects, the T cells are genetically modified to express a recombinant T cell receptor (TCR) or a chimeric antigen receptor (CAR) comprising an intracellular signaling domain, a transmembrane domain, and an extracellular domain comprising an antigen binding region. In particular aspects, the antigen is a tumor-associated antigen.

In certain aspects, the anti-CD38 antibody or antigen-binding fragment thereof is a monoclonal antibody, a chimeric antibody, a CDR-grafted antibody, a humanized antibody, a Fab, a Fab', a F(ab')2, a Fv, or a scFv.

In some aspects, the method further comprises administering an immune checkpoint inhibitor. In particular aspects, the immune checkpoint inhibitor is an anti-PD1 antibody and/or an anti-CTLA antibody. In some aspects, the at least one checkpoint inhibitor is selected from an inhibitor of CTLA-4, PD-1, PD-L1, PD-L2, LAG-3, BTLA, B7H3, B7H4, TIM3, KIR, or A2aR. In certain aspects, the PD-1 binding antagonist is nivolumab, pembrolizumab, pidilizumab, AMP-514, REGN2810, CT-011, BMS 936559, MPDL3280A or AMP-224. In one specific aspects, the anti-CTLA-4 antibody is tremelimumab or ipilimumab.

In certain aspects, the method further comprises administering at least a second therapeutic therapy. In some aspects, the at least a second therapeutic agent comprises chemotherapy, immunotherapy, surgery, radiotherapy, or biotherapy. In some aspects, the T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B, 1C, 1D, 1E, 1F:
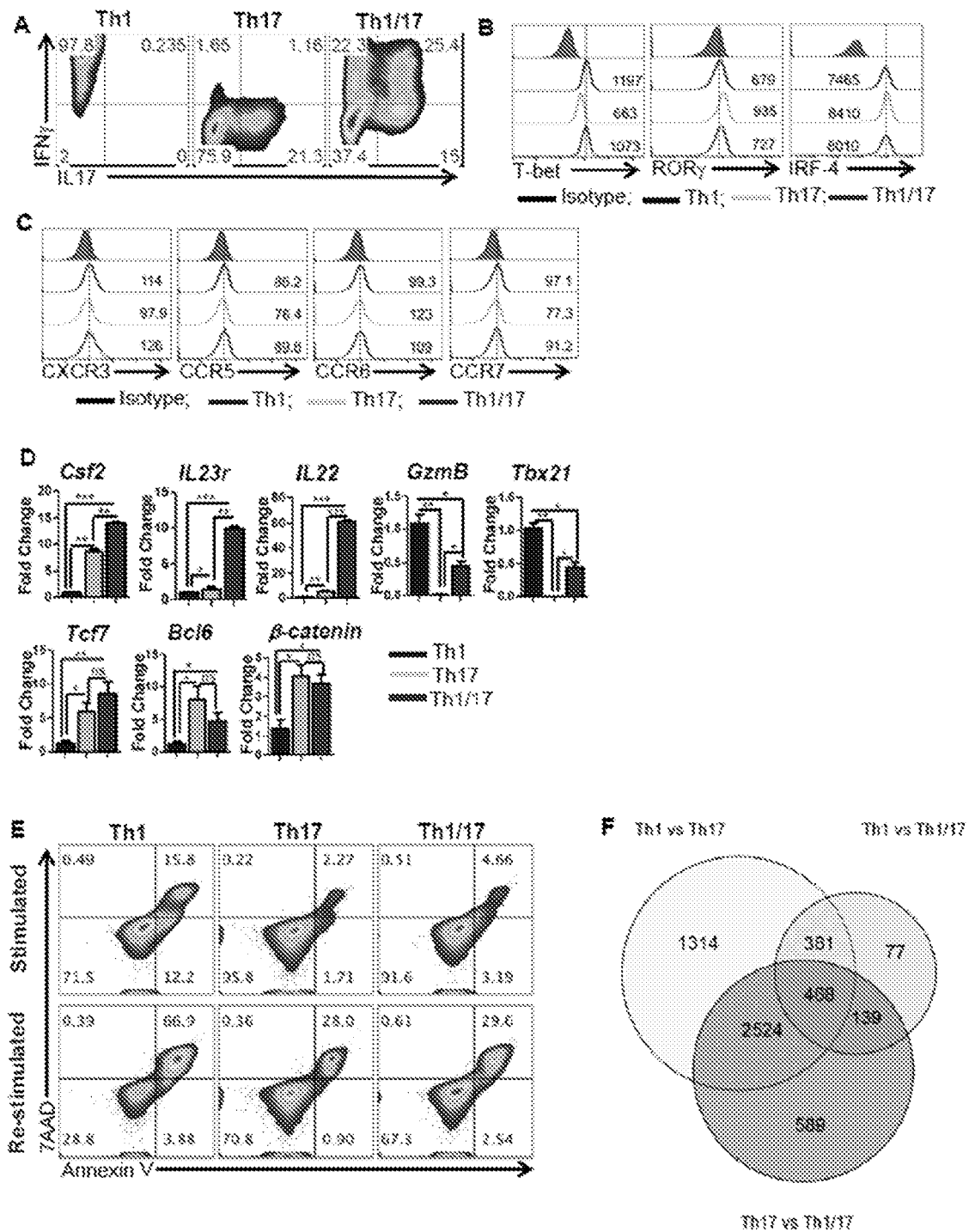
FIGS. 1A-1F: Hybrid Th1/17 cells possess traits of both Th1 and Th17 cells. The in vitro differentiated Th1, Th17 and hybrid Th1/17 cells were characterized for: (A-C) flow cytometry analysis of (A) intracellular cytokine secretion; (B) Th subset signature transcription factors (top to bottom: Isotype, Th1, Th17, TH1/Th17), (C) Th subset signature chemokine receptor, (D) qPCR based mRNA levels for key effector (upper panel) and stemness associated genes (lower panel). (E) Activation induced cell death of different Th subsets after overnight restimulation with anti-CD3 and anti-CD28 antibody (left to right: Th1, Th17, Th1/Th17), (F) Venn diagram representing the transcripts (obtained after Illumina bead-array) from Th1, Th17 and Th1/17 comparison. *p<0.05, p<0.01 and *p<0.005.

Adoptive T cell therapy (ACT) holds immense promise in eradicating large established tumors. Despite major advancements in understanding the functionality and the characteristics of various CD4 T cell subsets, the identification of T cell subsets with robust anti-tumor response is still obscure. Given that heightened effector function and prolonged persistence, the key attributes of Th1 and Th17 cells respectively, are prerequisites of potent anti-tumor T cells, certain embodiments of the present disclosure provides optimized culture conditions to ex vivo program hybrid Th1/17 cells that exhibit characteristics of both Th1 and Th17 cells.

Specifically, the method may comprise culturing a starting population of T cells in culture conditions to program the cells to a hybrid Th1/Th17 cell population. These hybrid Th1/Th17 cells can persist long-term in vivo while maintaining their effector function.

The present studies including transcriptional, metabolic, and proteomic profiling established that the enhanced anti-tumor property was attributed to increased NAD$^+$ mediated activity of histone deacetylase Sirt1 in the hybrid Th1/17 cells. Inhibition of NAD$^+$ or Sirt1 activity pharmacologically, or by using Sirt1-KO T cells exhibited a loss of stable anti-tumor control. Pharmacological or genetic inhibition of Sirt1 activity impaired the anti-tumor potential of Th1/17 cells. Importantly, T cells with reduced surface expression of the NADase CD38 exhibited intrinsically higher NAD+, enhanced oxidative phosphorylation, higher glutaminolysis and altered mitochondrial dynamics, and vastly improved tumor control. Lastly, blocking CD38 expression improved tumor control even when using Th0 anti-tumor T cells. Importantly, T cells with reduced surface expression of NADase CD38 and intrinsically higher NAD$^+$ exhibited improved tumor control and enhanced oxidative phosphorylation that correlated with higher glutaminolysis and altered mitochondrial dynamics as discerned in hybrid Th1/17 cells. Lastly, replenishing NAD$^+$ during the T cell expansion process or blocking the CD38 expression also resulted in improved tumor control even in the unpolarized anti-tumor T cells. Thus, strategies targeting the CD38-NAD$^+$ axis may have translational potential to increase the efficacy of ACT therapy.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. For example, a treatment may include administration of a hybrid Th1/Th17 cell therapy.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The term "immune checkpoint" refers to a molecule such as a protein in the immune system which provides signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, MR. The pathways involving LAG3, BTLA, B7H3, B7H4, TIM3, and MR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

The term "hybrid Th1/Th17" or "Th1/17" cells refers to a population of T cells which co-express IFNγ and IL17.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

II. T Cells for Adoptive Cell Transfer (ACT)

Embodiments of the present disclosure concern obtaining and administering T cells with low or no expression of CD38 to a subject as an immunotherapy to target cancer cells. Several basic approaches for the derivation, activation and expansion of functional anti-tumor effector T cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods of the present disclosure.

A. T Cell Preparation

In some embodiments, the T cells are derived from the blood, bone marrow, lymph, or lymphoid organs. In some aspects, the cells are human cells. In certain embodiments, T cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T (TSC$_M$), central memory T (TC$_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In particular aspects, the T cells are helper T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations. In particular aspects, the CD4+ T cells are sorted by methods known in the art, such as fluorescence assisted cell sorting (FACS).

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about $2 \times 10^6$ lymphocytes), e.g., from about 5 to about 21 days, preferably from about 10 to about 14 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days, preferably about 14 days. More preferably, rapid expansion provides an increase of at least about 200-fold (e.g., 200-, 300-, 400-, 500-, 600-, 700-, 800-, 900-, or greater) over a period of about 10 to about 14 days, preferably about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

In particular aspects, the T cells are differentiated to hybrid Th1/Th17 cells by culturing the presence of IL6, IL1β, IL23, TGFβ and IL12. The TGFβ may be present at a concentration of about 0.1 to 0.5 ng/mL. The IL1β, IL23, IL6, and/or IL12 may be present at a concentration of about 5 to 30 ng/mL. In particular aspects, the concentration of IL6 is about 25 ng/mL, IL1β is about 20 ng/mL, IL23 is about 20 ng/mL, TGFβ is about 0.3 ng/mL and IL12 is about 20 ng/mL. The differentiation may occur in the presence of anti-CD3 and/or anti-CD28 beads. The culture may further comprise anti-IL4 and/or anti-IFNα.

In other aspects, T cells with decreased or no expression of CD38 are produced by disruption of the expression of CD38. Disruption in some cases is transient or reversible and in other cases is permanent. Disruption in some cases is of a functional or full length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. In one method, the T cells are activated in the presence of anti-CD38 antibody. In another method, the T cells are contacted with siRNA or shRNA specific to CD38. Finally, the T cells may be genetically modified to disrupt CD38 using DNA-targeting molecule, such as a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be "engineered" to bind to a predetermined nucleotide sequence, for example via engineering (altering one or more amino acids) of the recognition helix region of a naturally occurring zinc finger or TALE protein.

B. Genetically Engineered Antigen Receptors

The T cells can be genetically engineered to express antigen receptors such as engineered TCRs and/or chimeric antigen receptors (CARs). For example, the autologous T-cells are modified to express a T cell receptor (TCR) having antigenic specificity for a cancer antigen. Suitable TCRs include, for example, those with antigenic specificity for a mesothelin antigen. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al., 2008 and Johnson et al., 2009.

In some embodiments, the T cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., Curr. Opin. Immunol., 2012; Wu et al., 2012. In some aspects, the genetically engineered antigen receptors include a CAR as described in U.S. Pat. No. 7,446,190, and those described in International Patent Application Publication No.: WO/2014055668 A1.

In some aspects, the tumor antigen is a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (Dl). For example, the target antigen is hTERT or survivin. In some aspects, the target antigen is CD38. In other aspects, the target antigen is CD33 or TIM-3. In other aspects, it is CD26, CD30, CD53, CD92, CD148, CD150, CD200, CD261, CD262, or CD362. In some embodiments, the engineered immune cells can contain an antigen that targets one or more other antigens. In some embodiments, the one or more other antigens is a tumor antigen or cancer marker. Other antigens include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gplOO, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD 123, CS-1, c-Met, GD-2, and MAGE A3, CE7, Wilms Tumor 1 (WT-1), a cyclin, such as cyclin Al (CCNA1), and/or biotinylated molecules, and/or molecules expressed by HIV, HCV, HBV or other pathogens.

2. Chimeric Antigen Receptors

In certain embodiments, the T cells are genetically modified to express a chimeric antigen receptor. In some embodiments, the chimeric antigen receptor comprises: a) an intracellular signaling domain, b) a transmembrane domain, and c) an extracellular domain comprising an antigen binding region.

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb). The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CDS, CD7, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3$^+$ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-ζ or Fc receptor γ and CD8, CD4, CD25 or CD16. In specific embodiments, intracellular receptor signaling domains in the CAR include those of the T-cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T-cell receptor complex in the intracellular domain. One or multiple cytoplasmic domains may be employed, as so-called third generation CARs have at least two or three signaling domains fused together for additive or synergistic effect, for example.

It is contemplated that the chimeric construct can be introduced into T cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the T cells. A large number of vectors are known that are based on viruses, where the copy number of the virus maintained in the cell is low enough to maintain the viability of the cell, such as, for example, vectors based on HIV, SV40, EBV, HSV, or BPV.

3. T Cell Receptor (TCR)

In some embodiments, the genetically engineered antigen receptors include recombinant T cell receptors (TCRs) and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; see also Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vβ; typically amino acids 1 to 116 based on Kabat numbering Kabat et al., 1991) at the N-terminus, and one constant domain (e.g., a-chain constant domain or $C_a$, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ζ chains, and a homodimer of CD3ζ chains. The CD3γ, CD3δ, and CD3δ chains are highly related cell surface proteins of the immunoglobulin superfamily containing a single immunoglobulin domain. The transmembrane regions of the CD3γ, CD3δ, and CD3δ chains are negatively charged, which is a characteristic that allows these chains to associate with the positively charged T cell receptor chains. The intracellular tails of the CD3γ, CD3δ, and CD3δ chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005. In some embodiments, the TCR or antigen-binding portion thereof can be synthetically generated from knowledge of the sequence of the TCR.

4. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

In some embodiments, the presently disclosed process can be used to genetically modify $CD26^{high}$ T cells derived from peripheral blood and/or umbilical cord blood to express CAR(s) that can be numerically expanded in vitro using aAPC (Singh et al., 2008; Singh et al., 2011; Shah et al., 2013). The process has implications for cell and gene therapy, due to the relative ease of DNA plasmid production, electroporation, use of thawed γ-irradiated master-bank aAPC, and can be readily transferred to facilities operating in compliance with current good manufacturing practice (cGMP) for clinical trials.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

III. Methods of Treatment

Provided herein are methods for treating or delaying progression of cancer in an individual comprising administering to the individual an effective amount T cell therapy, particularly T cells with decreased or no expression of CD38, such as hybrid Th1/Th17 of the present disclosure. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments, the T cells (e.g. unprogrammed Th0 cells) are administered in combination with at least one additional anti-cancer therapy, such as anti-CD38 antibody. The T cell therapy may be administered before, during, after, or in various combinations relative to an anti-cancer agent. The administrations may be in intervals ranging from concurrently to minutes to days to weeks. In embodiments where the T cell therapy is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the T therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m$^2$ fludarabine is administered for five days.

In certain embodiments, a T cell growth factor that promotes the growth and activation of the autologous T cells is administered to the subject either concomitantly with the autologous T cells or subsequently to the autologous T cells. The T cell growth factor can be any suitable growth factor that promotes the growth and activation of the autologous T cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2, IL-12 is a preferred T cell growth factor.

The T cell therapy and anti-cancer agent may be administered by the same route of administration or by different routes of administration. In some embodiments, the T cell therapy and/or anti-cancer agent is administered intravenously, intramuscularly, subcutaneously, topically, orally, transdermally, intraperitoneally, intraorbitally, by implantation, by inhalation, intrathecally, intraventricularly, or intranasally. An effective amount of the T cell therapy and anti-cancer agent may be administered for prevention or treatment of disease. The appropriate dosage of the T cell therapy and anti-cancer agent be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

B. Pharmaceutical Compositions

Also provided herein are pharmaceutical compositions and formulations comprising the activated T cell therapy, optionally an anti-cancer agent and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

C. Anti-Cancer Therapy

In certain embodiments, the compositions and methods of the present embodiments involve a T cell therapy in combination with at least additional anti-cancer agent. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may another subset of T cells, such as CD8$^+$ T cells. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a T cell therapy is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegalI); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above 2. Radiotherapy Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include, e.g., Mycobacterium bovis, Plasmodium falciparum, dinitrochlorobenzene, and aromatic compounds (U.S. Pat. Nos. 5,801,005 and 5,739,169); cytokine therapy, e.g., interferons α, β, and γ, IL-1, GM-CSF, and TNF; gene therapy, e.g., TNF, IL-1, IL-2, and p53 (U.S. Pat. Nos. 5,830,880 and 5,846,945); and monoclonal antibodies, e.g., anti-CD20, anti-ganglioside GM2, and anti-p185 (U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Articles of Manufacture or Kits

An article of manufacture or a kit is provided comprising the hybrid Th1/Th17 T cells is also provided herein. The article of manufacture or kit can further comprise a package insert comprising instructions for using the hybrid Th1/Th17 T cells to treat or delay progression of cancer in an individual or to enhance immune function of an individual having cancer. Any of the hybrid Th1/Th17 T cells described herein may be included in the article of manufacture or kits. In some embodiments, the hybrid Th1/Th17 T cells are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Hybrid Th1/Th17 Cells

Combined culture conditions of Th1 and Th17 cells generate hybrid Th1/17 cells: To merge the best functional traits of Th1 to Th17 cells, the culture conditions of Th17$^{IL1\beta+TGF\beta}$ cells (generated in presence of IL1β plus low dose of TGFβ) were modified since they exhibited superior anti-tumor response as compared to conventional Th17 cells (generated in the presence of TGFβ) due to reduced ecto-nucleotidase expression (Chatterjee et al., 2014). It was observed that using the culture conditions of IL6, IL1β, IL23, TGFβ$^{lo}$ with IL12 resulted in hybrid Th1/17 cells, which not only co-express elevated levels of IFNγ and IL17 (FIG. 1A and FIG. 8A, 8B) but also exhibit a phenotypic signature akin to the pathogenic Th17 cells (Lee et al., 2012). The hybrid Th1/17 cells displayed intermediate levels of both Th1 and Th17 signature transcription factors (T-bet, RORγ, IRF-4) (FIG. 1B), chemokine receptors (CXCR3, CCR6) (FIG. 1C), effectors (GzmB, Tbx21, GM-CSF) and sternness-associated genes (IL22, IL23R, TCF7, BCL6, β-catenin) (FIG. 1D), along with TCR restimulation induced cell death (FIG. 1E). Taken together, this data confirm that the unique ex vivo programming condition can generate hybrid Th1/17 cells with the best characteristics of Th1 and Th17 cells.

Figures 8A, 8B, 8C, 8D:
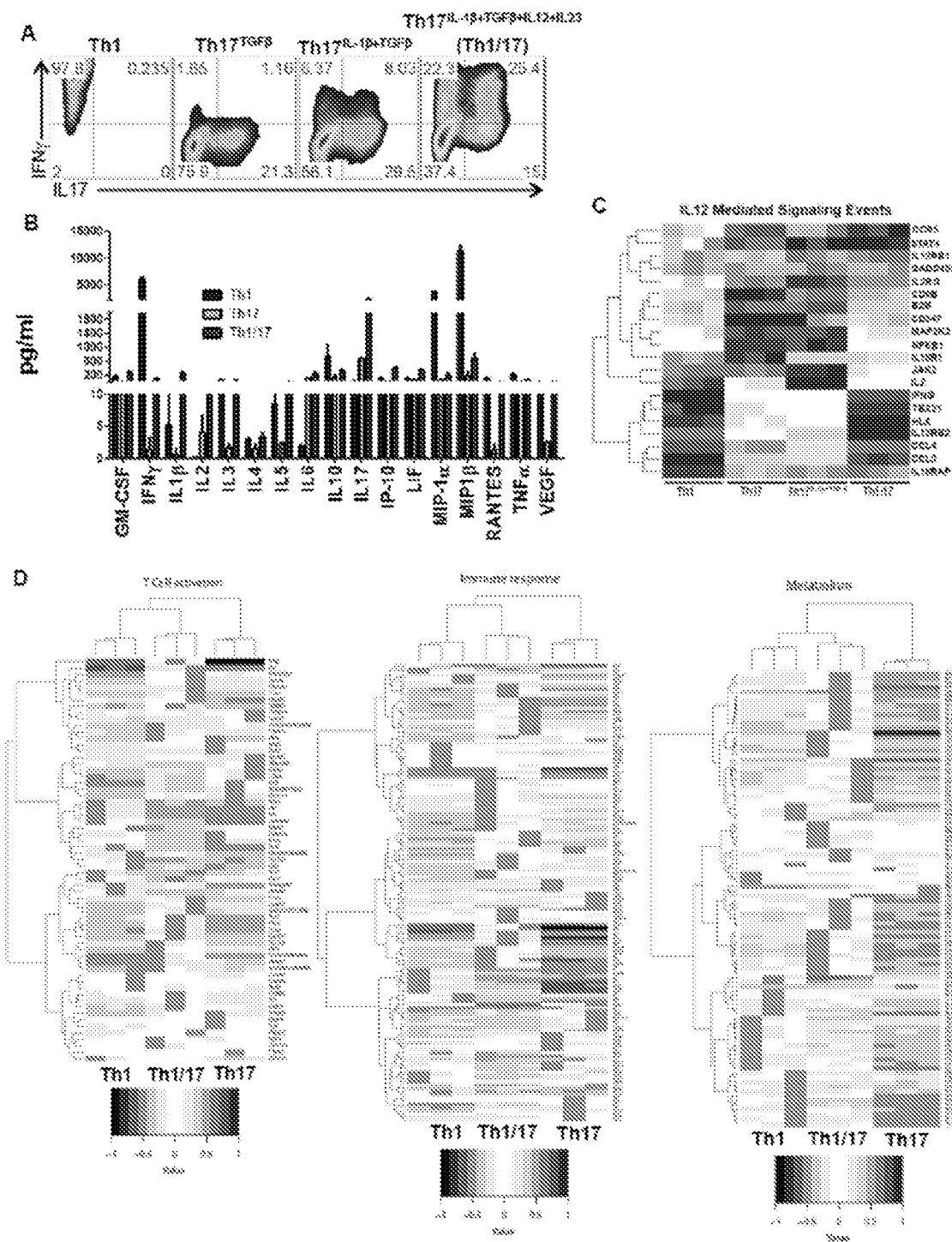
FIGS. 8A-8D: Hybrid Th1/17 cells possess traits of both Th1 and Th17 cells (see FIG. 1). (A) Purified CD4+ T cells differentiated ex vivo to Th1, Th17 and Th1/17 cells were re-stimulated for 4 hr with PMA and ionomycin before the samples were stained with fluorochrome conjugated antibodies and acquired using flow cytometry. Data are representative of three independent experiments with similar results. (B) Purified CD4+ T cells differentiated ex vivo to Th1, Th17 and Th1/17 cells were re-stimulated overnight with anti-CD3 (2 µg/ml)+anti-CD28 (2 µg/ml). Supernatant obtained after re-stimulation were evaluated for different cytokines and chemokines using multiplex assay. (C-D) Transcripts (obtained from Illumina bead array analysis) significant at <0.1 from Th1, Th17 and Th1/17 were compared using Venny, a tool for generating and visualizing area proportional Venn diagrams and 607 transcripts were common to both the Th1 vs Th1/17 and Th17 vs Th1/17 comparisons. Heatmap (C and D) represent the genes that mapped to T cell activation, immune response and metabolism pathways.

Next, a comparative Illumina microarray analysis showed that 589 genes were exclusively expressed in hybrid Th1/17 cells (FIG. 1F), with Th1/17 cells exhibiting dominant Th1 or Th17 genes. For instance, analysis of IL12 signaling-related molecules showed that hybrid Th1/17 programming results in upregulation of STAT4 and higher levels of the IL12 receptor component, IL12Rβ2, which is normally reduced in Th17 cells (FIG. 8C). Given the role of IL18 in immunosuppression (Terme et al., 2011), Hlx in maintaining a heritable Th1 gene expression (Mullen et al., 2002), and CCL3-CXCR3 circuit in trafficking of T cells to sites of inflammation (Lord et al., 2005), it was proposed that this unique molecular signature would be advantageous in exhibiting reduced susceptibility of hybrid Th1/17 cells to immunosuppression and increased anti-tumor activity. Further, a unique metabolic and T cell signalling pathway gene expression was also observed in hybrid Th1/17 cells (FIG. 8D).

Figures 2A, 2B, 2C, 2D:
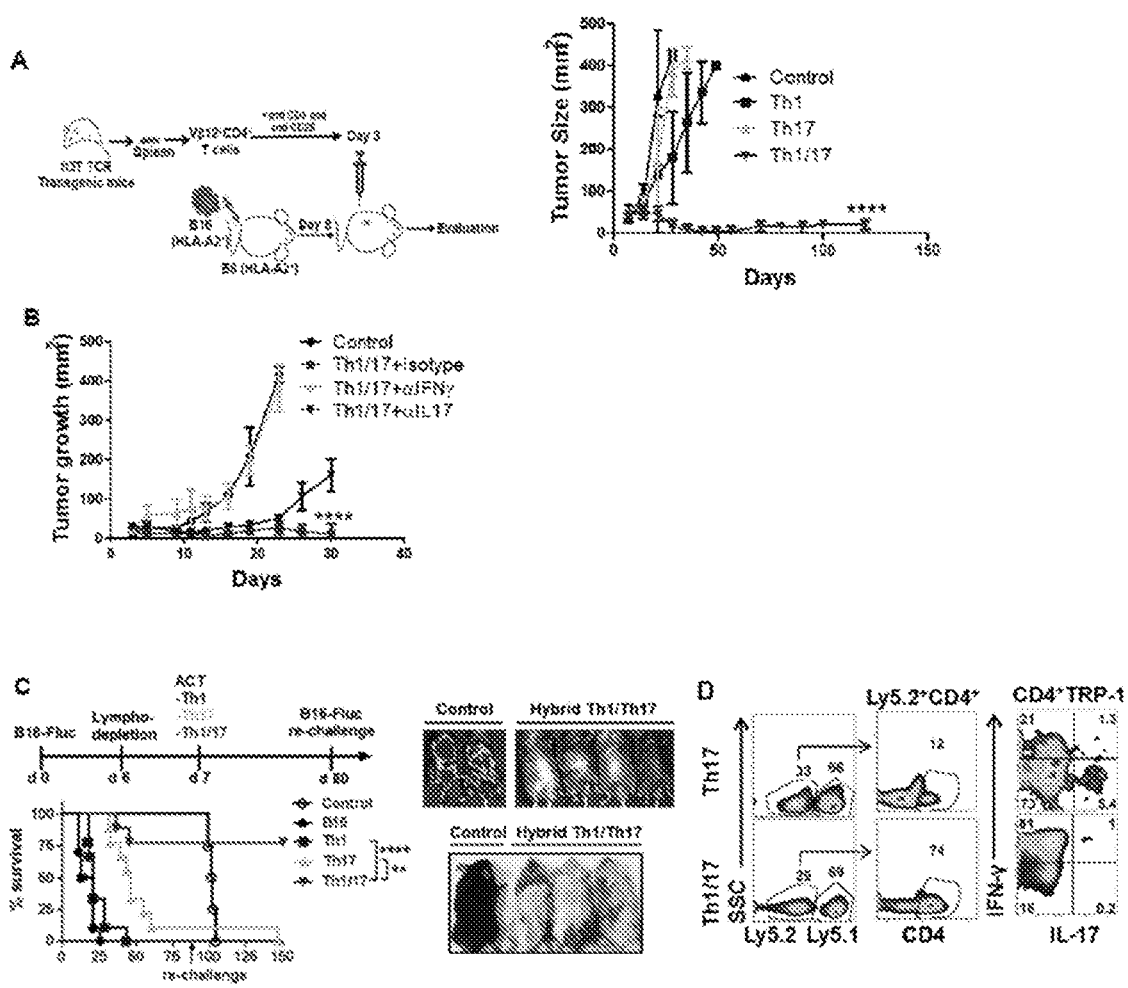
FIGS. 2A-2D: Hybrid Th1/17 cells exhibit superior anti-tumor response. (A) Schematic presentation of the experimental strategy (left panel) and the differences observed in tumor growth (right panel) when subcutaneously established B16-A2 tumor in HLA-A$^+$ mice (n=8 mice/group) were treated by adoptively transferring tyrosinase reactive TIL 13831 TCR transgenic T cells differentiated to Th1, Th17 and hybrid Th1/17 cells. Data demonstrate mean tumor size at each time point in 1 of the 3 experiments with similar results. (B) C57BL/6 mice with 10 day subcutaneously established B16-F10 melanoma tumor were either kept untreated or treated by transferring $0.5\times10^6$ TRP-1 Th1/17 cells. The treated group was subdivided to administer 100 μg neutralizing antibody against IFNγ, IL17 or isotype control Ab intraperitoneally every alternate day. Tumor growth curve for various groups with n=4 is shown. (C) C57BL/6 Ly5.1$^+$ recipients were injected (i.v.) with $0.5\times10^6$ luciferase-transduced B16-F10 (B16-Fluc) and following lymphodepletion (sub-lethally irradiation with 500 cGy) on day 6. Groups of mice were adoptively transferred with either $0.25\times10^6$ TRP-1 Th1, Th17 or Th1/17 cells on day 7. Survival and tumor growth (left panel) were followed with bioluminescent imaging. On day 80, recipient mice were re-challenged by injecting $0.5\times10^6$ B16-Fluc tumors. Survival and tumor growth were followed until day 150 by bioluminescent imaging (upper right). Lower right panel shows that mice receiving hybrid Th1/17 developed a strong vitiligo on the skin. (D) Representative flow panel showed tumor-infiltrating lymphocytes (TILs) recovered from lung on day 150 from Ly5.1$^+$ recipient mice and re-stimulated with PMA and Ionomycin for 4 h in vitro to measure IFNγ and IL17 secretion. ****$p<0.0001$.
Figures 9A, 9B, 9C, 9D:
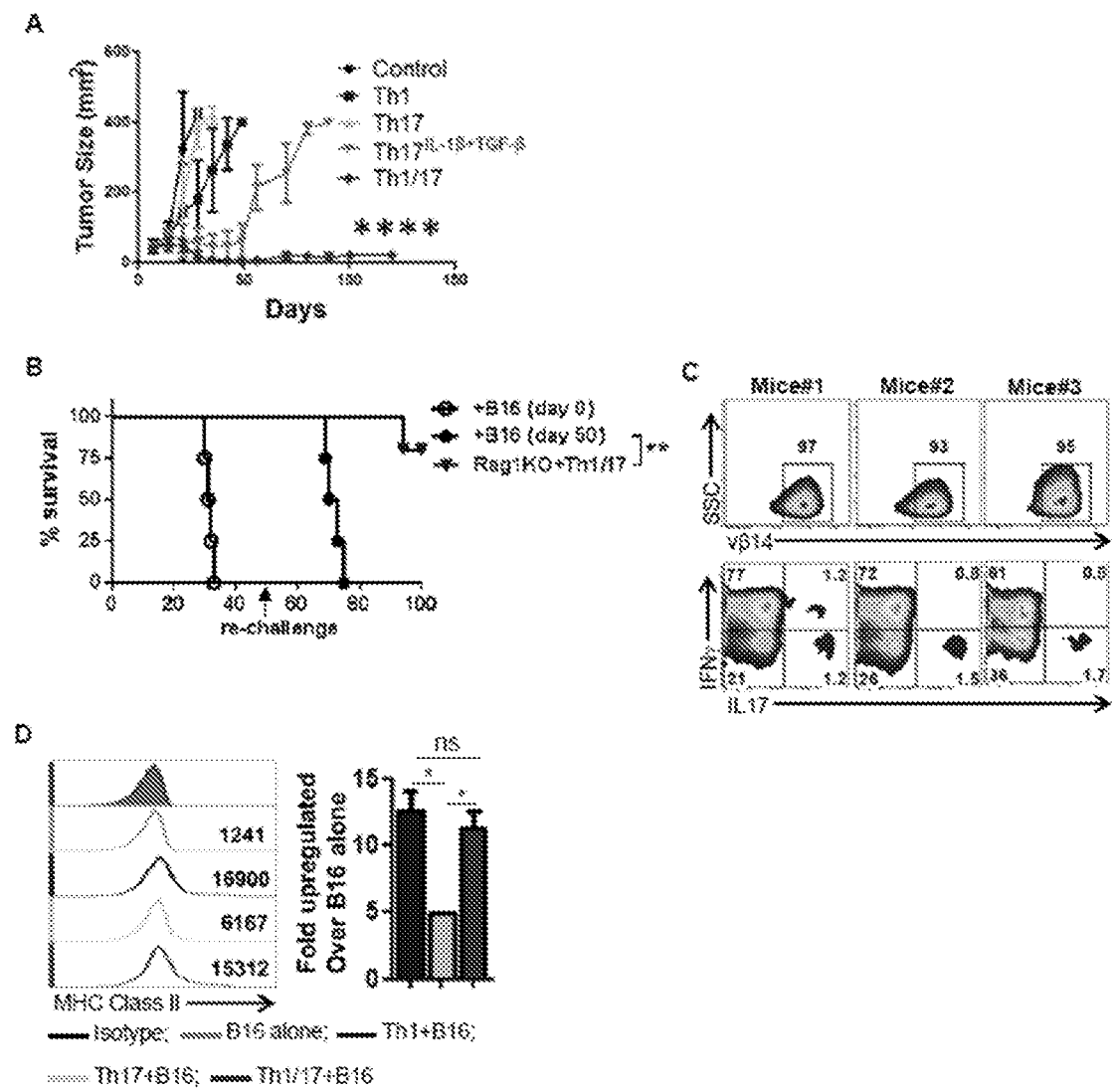
FIGS. 9A-9D: Hybrid Th1/17 cells exhibit superior anti-tumor response (see FIG. 2). (A) HLA-A2+ (n=8 mice/group) mice were inoculated (s.c.) with 0.25×106 B16-F10-HLA-A2+ murine melanoma cells and after nine days mice were either left as untreated control or treated by adoptively transferring 0.3×10$^6$ tyrosinase reactive TIL1383I TCR transgenic T cells differentiated to Th1, Th17, Th17IL1β+ TGFβ and hybrid Th1/17 cells. Tumor growth was measured using digital caliper every fourth day. Data in the figure demonstrates mean tumor size at each time point in one of the three experiments with similar results. (B-C) Rag1 deficient (Rag1KO) mice were i.v. injected with 0.5×10$^6$ luciferase-transduced B16-F10. Lympho-depletion was induced one day prior to hybrid Th1/17 T cell transfer. B16-Fluc was infused for tumor re-challenge on day 50. (B) Survival and tumor growth were followed. (C) Representative flow panel depicts TILs recovered from lungs of Rag1KO mice on day 120 and analyzed for expression of Vβ14+CD4+ T cells. Recovered TILs were stimulated with PMA and ionomycin before analysis for intracellular IFNγ and IL17 levels was done using flow cytometry. (D) Flow cytometry analysis of MHC Class II expression on B16 melanoma cells was performed after overnight co-culture at 1:1 ratio with either in vitro differentiated TRP-1 Th1, Th17 or Th1/17 cells. Adjacent bar diagram represents fold upregulation of MHC class II expression on B16 melanoma from Th subset co-culture group over B16 alone. Data are representative of 3 independent experiments with similar results. *p<0.05 and ****p<0.0001
Figures 10A, 10B, 10C, 10D, 10E, 10F, 10G, 10H, 10I, 10J:
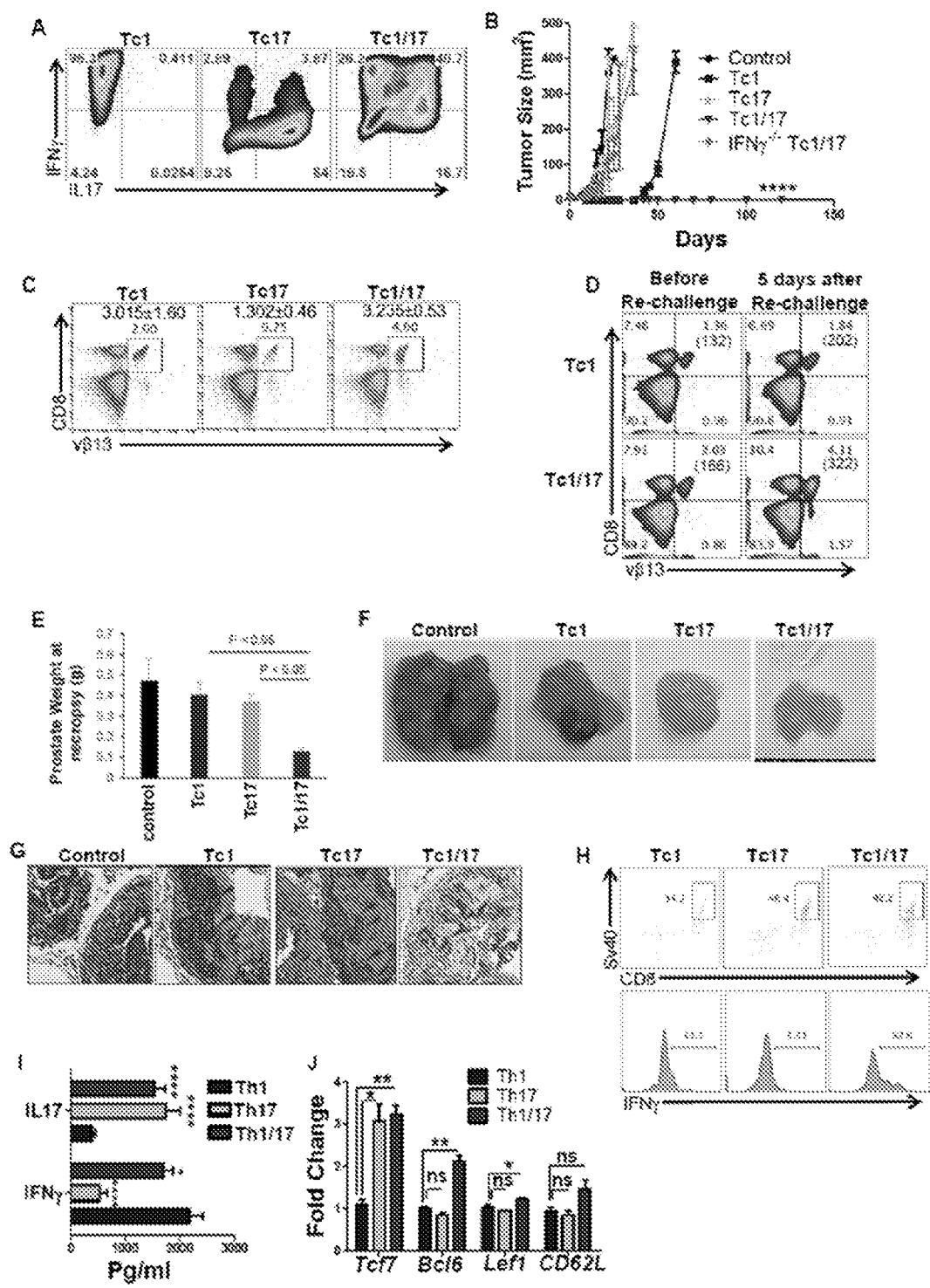
FIGS. 10A-10J: Hybrid Tc1/17 cells is superior to Tc1 and Tc17 cells in controlling tumor (see FIG. 2). (A) Melanoma epitope gp100 reactive T cells obtained from Pmel TCR transgenic mouse were used for differentiation to Tc1, Tc17 and Tc1/17 cells using the similar protocol that was used to differentiate Th1/17 cells. These Tc subsets were then re-stimulated with PMA and ionomycin for 4h and analyzed for the intracellular cytokine accumulation using flow-cytometry. Data are representative of three independent experiments with similar results. (B-D) C57BL/6 mice (n=5 mice/group) were inoculated (s.c.) with 0.25×106 B16-F10 murine melanoma cells and after nine days mice either left as untreated control or treated by adoptively transferring ex vivo differentiated 1×106 Pmel Tc1, Th17, Tc1/17 or IFNγ−/− Tc1/17 cells. Tumor growth was measured using digital calipers every fourth day. B) Data in figure demonstrate mean tumor size at each time point. (C) Persistence of adoptively transferred cells in the peripheral blood of tumor bearing mice following 21 days after ACT. (D) The mice from the group which received Tc1 and Tc1/17 were re-challenged with B16-F10 tumors on day 50, and the transferred gp100 specific Vβ13+ cells were tracked five days later in the blood using FACS. E-H) TRAMP (Transgenic Adenocarcinoma of the Mouse Prostate) mice were adoptively transferred with either Sv40 antigen specific Tc1 or Tc17 or Tc1/17 cells and were euthanized 57 days post ACT for detailed analysis. (E) Graph depicts the prostate weight of mice at necropsy showing significant reduction in prostate weight of TRAMP mice that were treated by adoptively transferred Tc1/Tc17 cells, as compared to those treated with either Tc1 or Tc17 cells alone. (F) Representative images of the prostate from TRAMP mice treated in E are shown. (G) Representative micrographs of H&E staining showing the histology of the prostate from TRAMP mice. Arrowheads indicate tumors in the prostate gland. (H) Flow cytometry analyses demonstrating significantly higher IFNγ secretion (lower panel) within the Sv40 tetramer specific CD8+ T cells (upper panel). (I) Peripheral blood from normal healthy human donor was used to purify CD4+ T cells using magnetic beads and subjected to differentiation ex vivo to Th1, Th17 and Th1/17 cells. These Th subsets were re-stimulated overnight with anti-CD3 (2 µg/ml) and anti- CD28 (2 µg/ml) and the supernatant collected was characterized for IFNγ and IL17 levels using ELISA. (J) RNA prepared from human Th1, Th17 and Th1/17 cells was used for qPCR based analysis of various sternness associated genes. *p<0.05, p<0.01 and *p<0.005, ****p<0.0001

Hybrid Th1/17 cells exhibit enhanced anti-tumor potential: A comparative determination of the anti-tumor property between Th1, Th17 or Th1/17 cells differentiated ex vivo using melanoma epitope tyrosinase reactive CD4$^+$ T cells obtained from h3T TCR transgenic mice (Mehrotra et al., 2012), showed that adoptive transfer of hybrid Th1/17 cells exhibit superior tumor control as compared to Th1, Th17 (FIG. 2A) or even Th17$^{IL1\beta+TGF\beta}$ cells (FIG. 9A). Administering anti-IFNγ or anti-IL17 antibody to the recipient mice along with ACT showed that IL17 neutralization had minimal effect on B16 tumor progression, at least during the initial three weeks, whereas blocking of IFNγ completely diminished the anti-tumor potential of Th1/17 cells (FIG. 2B). This indicates that IFNγ is needed for the anti-tumor response of Th1/17 cells. Further, hybrid Th1/17 cells generated using a different tumor epitope, tyrosinase-related protein-1 (TRP-1) TCR, were also better than Th1 or Th17 cell in treating metastatic lung tumors (FIG. 2C). Importantly, tumor-free mice when re-challenged with the same tumor did not show any tumor growth until 150 days, the latest time point observed, and instead developed vitiligo, (FIG. 2C, right lower panel), while maintaining IFNγ signature (FIG. 2D). This indicates the sustained lytic activity of the adoptively transferred T cells against TRP-1 antigen which is also expressed by the melanocytes. Moreover, the anti-tumor property of hybrid Th1/17 was independent upon endogenous immune cells, as it also controlled tumor effectively in Rag1$^{-/-}$ recipients (FIGS. 9B and 9C). The direct tumoricidal activity of the Th1/17 cells is explained by their ability to enhance MHC Class II expression on B16 melanoma cells, after melanoma epitope TRP-1 specific T cells differentiated to either Th1 or Th17 or Th1/17 were co-cultured in vitro with B16 tumor overnight (FIG. 9D). A complete necropsy revealed that histologically there were no obvious pathological manifestation in the experimental animals, and any changes observed reflected physiological responses to the experiment. The organ weight to body weight ratios was also compared and no significant differences were noticed between groups.

Given long-term tumor control observed with murine hybrid Th1/17 cells, similar strategies to generate hybrid Tc1/17 using class I restricted epitope reactive T cells also exhibited vastly improved tumor control as compared to Tc1 and Tc17 cells alone in both murine melanoma (using gp100 reactive T cells), and a spontaneous prostate tumor model (using Sv40 reactive T cells) (FIG. 10A-H). Next, it was determined if the ex vivo programming strategy has the potential to generate tumor-reactive human T cells for ACT. Using purified CD4$^+$ T cells from normal healthy donors human Th1/17 hybrid cells were able to be generated, as indicated by the IFNγ and IL17 cytokine profile (FIG. 10I). Further, the data in FIG. 10J shows that ex vivo programming of tumor infiltrating lymphocytes (TILs) obtained from a metastatic melanoma patient resulted in increased 'stern-ness' features associated with the present programming protocol.

Figures 3A, 3P:
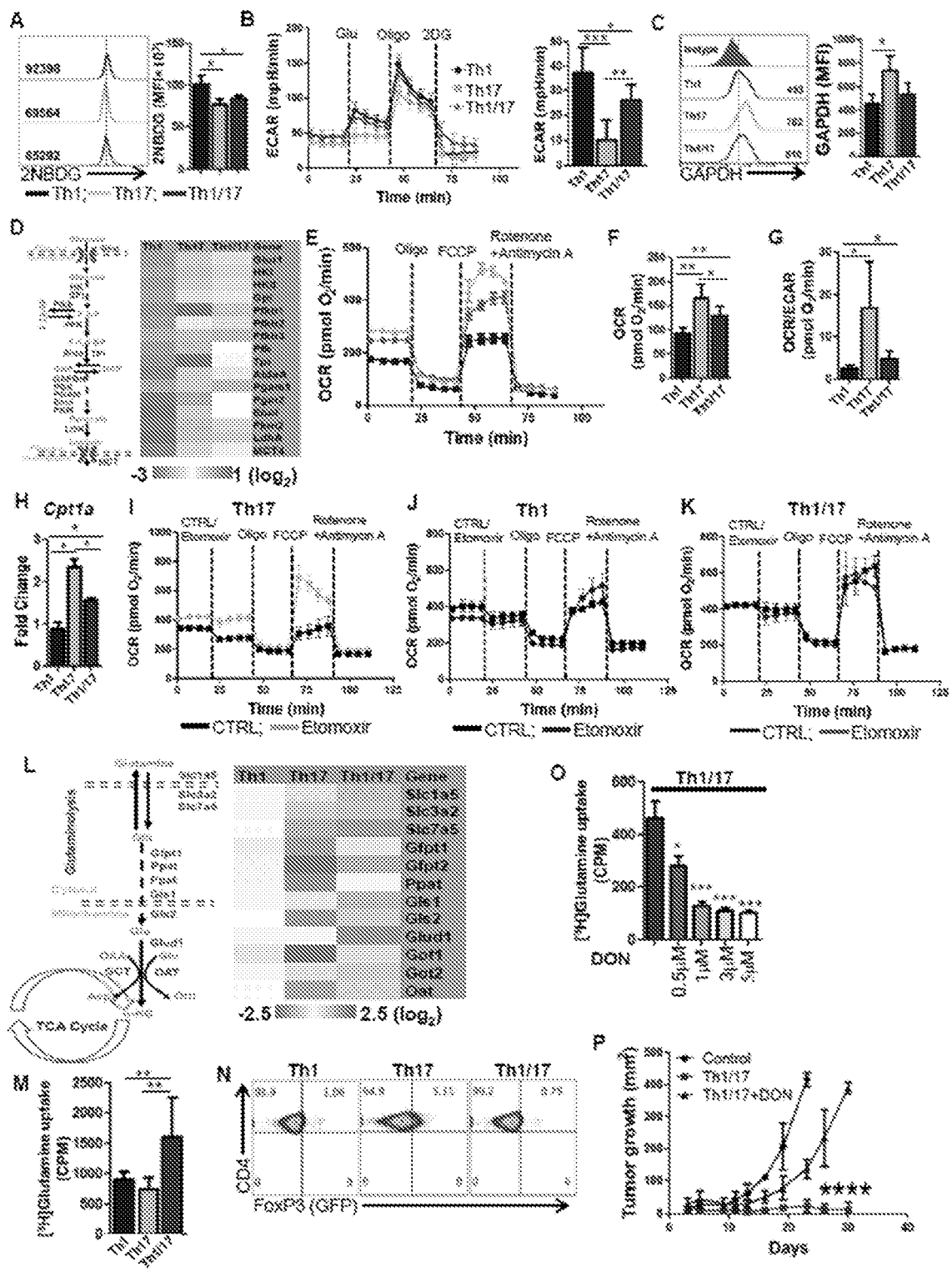
FIGS. 3A-3P: Hybrid Th1/17 cells are metabolically distinct from Th1 and Th17 cells and depend upon glutaminolysis. The ex vivo programmed Th1, Th17 and Th1/17 cells were used to determine: (A) Glucose uptake using 2NBDG. Adjacent bar diagram represents the cumulative data of mean fluorescence intensity (MFI) from three independent experiments. (B) ECAR time course in response to glucose, oligomycin and 2DG (left panel). Adjacent bar shows ECAR levels after glucose addition. (C) Intracellular expression of GAPDH by FACS. Adjacent bar represents cumulative data from 3 experiments. (D) Glycolysis associated genes using qPCR. Genes including Glut1, HKI, HKII, Pfkb1, Pkm2, and LdhA are lower in Th1/Th17 while Pfkb3 and Pgam 1 are higher. (E-G) Oxygen consumption rate (OCR) under basal condition and in response to indicated mitochondrial inhibitors. Graphs representing time course (E), basal OCR (F), and OCR/ECAR ratio (G). (H) Expression of CTP1a using qPCR. (I-K) OCR in presence or absence of etomoxir (200 μM) followed by the addition of various mitochondrial inhibitors as indicated in Th17 (I), Th1 (J) and Th1/17 (K). (L) Expression of various glutaminolysis associated genes using qPCR. (M) Uptake of radiolabelled glutamine that was measured in count per minute (CPM). Data is mean of 4 replicate samples from the 3 repeat experiments. (N) FoxP3 expression in FoxP3-GFP knock-in CD4$^+$ T cells differentiated to Th1, Th17 and Th1/17 phenotype. (O) Uptake of radiolabelled glutamine in Th1/17 cells cultured in presence of different conc. of DON. Representative data from 1 of 3 independent experiments is shown. (P) TRP-1 Th1/17 cells differentiated either in presence of vehicle control (DMSO) or DON (3 μM) were adoptively transferred ($0.5\times10^6$) in 9 days s.c. established B16-F10 melanoma tumor bearing mice and tumor growth was measured. Results for tumor area are the mean of measurements±standard deviation, from at least 4 mice per group. *$p<0.05$, $p<0.01$ and *$p<0.005$.

Metabolically unique Th1/17 cells depend upon glutaminolysis: Metabolic commitment plays an important role in function and survival of T cells in a tumor microenvironment (Scharping et al., 2016; Sukumar et al., 2013). It was observed that uptake of 2NBDG, a fluorescent glucose analogue which indicates glycolytic commitment, was highest in Th1 cells followed by intermediate level in Th1/17 and lowest in Th17 cells (Th1>Th1/17>Th17) (FIG. 3A). Similarly, extracellular acidification rate (ECAR) was also intermediate in Th1/17 cells relative to Th1 and Th17 cells (FIG. 3B). This corresponds to the intermediate level of free GAPDH (FIG. 3C), which inversely regulate IFNγ by binding to the AU-rich elements within its 3' UTR mRNA (Chang et al., 2013). Hybrid Th1/17 also exhibited intermediate expression of various glycolytic enzymes as determined by quantitative PCR (q-PCR) (FIG. 3D). Th17 and Th1/17 cells showed lower expression of lactate dehydrogenase A (LDHA, converts pyruvate to lactate) and MCT4 (transports lactate out of the cell) as compared to Th1 cells, suggesting that pyruvate generated in glycolysis can be more efficiently integrated into the TCA cycle to fuel mitochondrial metabolism (FIG. 3D). Additionally, mitochondrial oxygen consumption rate (OCR), an indicator of OXPHOS, was also intermediate in hybrid Th1/17 cells (FIGS. 3E and 3F). Notably, the Th17 and Th1/17 cells possessed a higher OCR/ECAR ratio as compared to Th1 cells (FIG. 3G), indicating that Th17 and Th1/17 cells preferentially use OXPHOS whereas Th1 cells mostly use glycolysis to fulfil their bioenergetic demands.

Since fatty acid oxidation (FAO) has been shown to modulate OXPHOS by providing acetyl-CoA, a substrate for TCA cycle, the influence of FAO was evaluated in affecting OXPHOS of different T cell subsets. Consistent with lower OXPHOS, mRNA level of CPT1a, a rate-limiting enzyme that regulates the entry of fatty acid from cytosol to mitochondria (Jogl et al., 2004), was significantly reduced in Th1 and Th1/17 cells as compared to Th17 cells (FIG. 3H). Moreover, inhibition of CPT1a using etomoxir significantly depleted OCR and SRC values in Th17 cells (FIG. 3I), whereas OXPHOS in Th1 and Th1/17 cells were mostly unaffected (FIGS. 3J and 3K), suggesting less dependence of Th1/17 cells on FAO as compared to Th17 cells in maintenance of high OXPHOS.

Figures 11A, 11B, 11C, 11D, 11E, 11F, 11G, 11H, 11I, 11J, 11K, 11L:
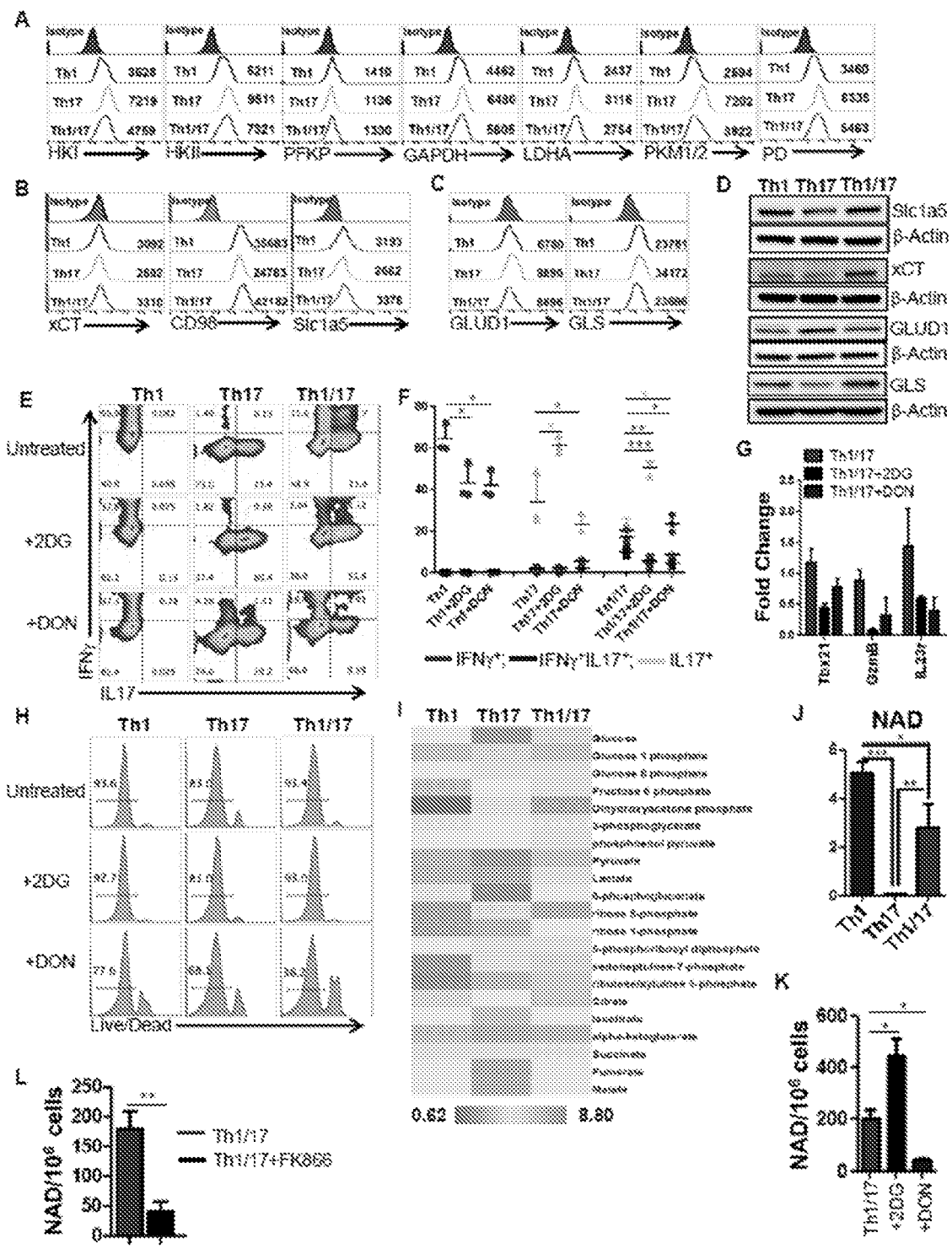
FIGS. 11A-11L: Metabolic commitment of Th1, Th17 and Th1/17 cells (see FIGS. 3-4). (A-C) In vitro differentiated murine Th1, Th17 and Th1/17 cells were used for determining: (A) intracellular expression of various glycolytic enzymes, (B) cell surface expression of different amino acid transporters, and (C) intracellular expression of glutaminolytic enzymes by flow cytometry. Data are representative of three independent experiments with similar results. (D) Western blot analysis determined the protein level of various glutamine transporters and glutaminolytic enzymes in in vitro differentiated Th1, Th17 and Th1/17 cells. β-actin was used as a loading control. Data are representative of two independent experiments with similar results. (E-F) Purified $CD4^+$ T cells were differentiated to Th1, Th17 and Th1/17 cells either in presence or absence of 2DG (1 mM) or DON (3 µM) and characterized for: (E) intracellular cytokine secretion after restimulating them with PMA and ionomycin for 4 hr, (F) determining the frequency of cells that were $IFNγ^+$, $IL17^+$ or $IFNγ^+IL17^+$ in each treatment groups and presented using scatter plot. Statistical comparison between treated and untreated groups are indicated. (G) RNA preparation that was used for qPCR based analysis of various effector genes, and (H) determining the percentage of viable cells by FACS based staining with live/dead dye. Numerical values represent the percent gated viable cells. Data are representative of three independent experiments with identical results. (I) Purified $CD4^+$ T cells were differentiated into Th1, Th17 and Th1/17 cells and intracellular metabolites were measured using mass spectrometry. Depicted heat maps are the representation of the relative amount of each metabolite from Glycolysis, PPP and TCA cycle. (J) Th1, Th17 and Th1/17 cells were used for determining intracellular levels of $NAD^+$. (K-L) Th1/17 cells differentiated ex vivo either in presence of vehicle control or (K) 2DG (1 mM) or DON (3 µM), (L) or FK866 (10 nM) were used to determine intracellular levels of $NAD^+$. Data are representative of three independent experiments with similar results. *p<0.05, p<0.01 and *p<0.005.

Because activation of T cells is also accompanied by the up-regulation of glutamine catabolism that provides intermediates such as α-ketoglutarate which can be metabolised through TCA cycle to fuel OXPHOS (Newsholme et al., 1985), it was next sought to determine the impact of glutaminolysis in the metabolic commitment of different T cell subsets. The genes associated with glutamine uptake (e.g., glutamine transporters Slc1a5, Slc3a2 and Slc7a5), and its catabolism were considerably higher in hybrid Th1/17 cells as compared to Th1 and Th17 cells (FIG. 3L). Upon evaluating key glycolytic and glutamine pathway proteins analysed using flow cytometry (FIG. 11A-C), the lowest levels of free glycolytic enzymes were observed indicating active glycolysis in Th1 cells (FIG. 11A), while the Th1/17 cells exhibited the highest levels of glutamine transporters (FIG. 11B) and lower level of free enzyme in glutamine pathway (FIG. 11C). Immunoblot analysis also showed increased protein level of glutamine transporters and catabolic enzymes in Th1/17 cells (FIG. 11D), indicating its increased dependence on glutamine metabolism. This suggests that higher glutaminolysis in Th1/17 cells could play a major role in maintaining high OXPHOS commitment. Importantly, increased incorporation of radio labelled glutamine in Th1/17 cells relative to Th1 and Th17 cells also confirmed glutaminolysis dependence of hybrid cells (FIG. 3M).

The functional consequence of differential gluatamine metabolism in Th subsets was supported by the observation that Th17 cells with low glutaminolysis express a sizable population positive for FoxP3, whereas its expression is significantly reduced in Th1/17 with high glutaminolysis (FIG. 3N). This is in accordance with the study that inefficient or reduced glutaminolysis promotes expression of FoxP3 in T cells (Klysz et al., 2015). Thus, increased glutaminolysis in hybrid Th1/17 cells likely contributes to reduced trans-differentiation to FoxP3$^+$ phenotype and an effective tumor control.

To comprehensively determine the dependence of Th1/17 cells on glutaminolysis for its effector function and antitumor potential, glutaminolysis was inhibited in Th1/17 cells using 6-Diazo-5-oxo-L-norleucine (DON), a glutaminase inhibitor. Similar to 2DG which has been shown to affect IFNβ production by T cells (Chang et al., 2013), the data suggest that blocking of glutaminolysis also reduces the differentiation of Th1/17 cells as evident by reduction in IFNγ$^+$IL-17$^+$ secreting fraction (FIGS. 11E and 11F). Most importantly, effector molecules (FIG. 11G) and the viability of Th1/17 cells was also reduced by two-folds in Th1/17 cells as compared to Th1 or Th17 cell cultured in presence of DON (FIG. 11H). Further, DON pre-treatment of Th1/17 cells not only reduced the uptake of radio labelled glutamine in a dose dependent manner (FIG. 3O) but also showed significant attenuation of the anti-tumor response upon ACT (FIG. 3P), likely due to reduced in vivo viability in absence of active glutaminolysis.

Figures 4A, 4B, 4C, 4D, 4E:
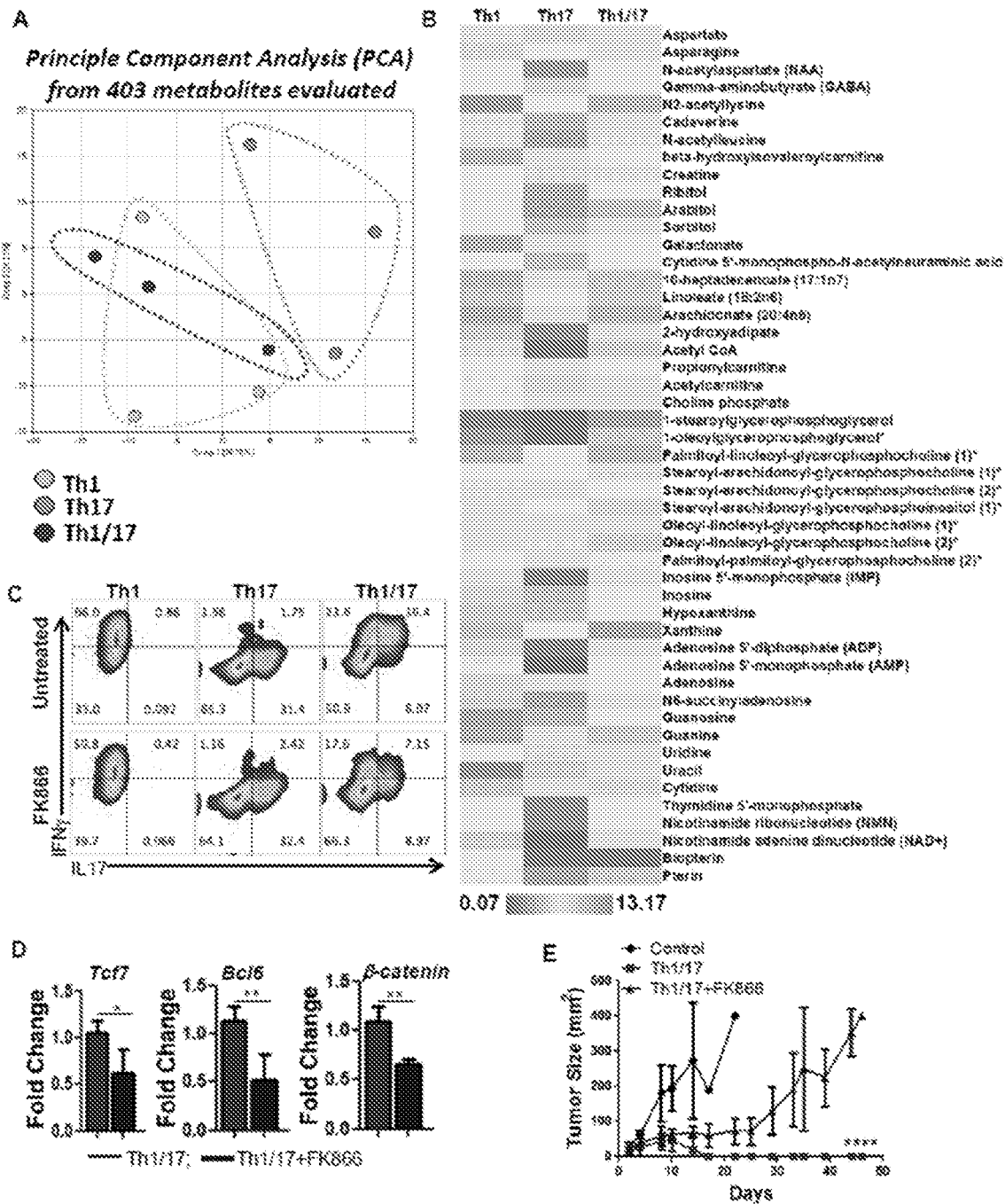
FIGS. 4A-4E: Metabolite NAD regulates hybrid Th1/17 cell function. Purified CD4$^+$ T cells differentiated to Th1, Th17 and Th1/17 were used for quantifying intracellular metabolite levels using mass spectrometry. The principle component analysis (PCA) is shown in (A), and (B) shows relative levels of metabolite. Th1, Th17 and Th1/17 cells differentiated either in presence of vehicle control (DMSO) or FK866 (10 nM) were used for determining: (C) intracellular cytokine secretion by FACS, (D) expression of stemness associated genes, (E) ability to control growth of tumor s.c. established B16-F10-HLA-A2$^+$ murine melanoma cells upon adoptive transfer. Tumor growth was measured using digital calipers every fourth day. Data in Figure demonstrate mean tumor size at each time point in 1 of the 2 experiments with similar results. *$p<0.05$, $p<0.01$, *$p<0.005$ and ****$p<0.0001$.

Increased levels of metabolite nicotinamide adenine dinucleotide (NAD$^+$) in Th1/17 cell: A comprehensive evaluation of principle metabolites (using services from Metabolon, Inc.) shows that hybrid Th1/17 cells possess a metabolite signature that is also intermediate between the Th1 and Th17 cells (FIG. 4A). FIG. 4B shows the panel of metabolites that were significantly different between the Th1, Th17 and Th1/17 cell groups. Consistent with the gene expression and metabolic flux data, metabolomic analysis also revealed that Th17 cells had higher level of acyl carnitine and propionylcarnitine required for FAO relative to Th1/17 cells (FIG. 4B). Late TCA cycle intermediates like fumarate and malate were also higher in Th1/17 cells, which may indicate the preferential FAO in Th17 cells while increased pyruvate and glutamine oxidation in Th1/17 cells (FIG. 11I).

Interestingly, it was found that there was a striking 34-fold increase in NAD$^+$ levels in Th1/17 cells as compared to Th17 cells (FIG. 11J). This was dependent on glutaminolysis since DON treatment significantly reduced NAD$^+$ levels, whereas 2DG treatment increased the NAD$^+$ level in Th1/17 cells (FIG. 11K). Owing to the well-characterized role of NAD$^+$ in regulating T cell proliferation, cytokine production and survival (Bruzzone et al., 2009; Tullius et al., 2014), the impact of modulating NAD$^+$ on Th1/17 cell function was determined. It was observed that depletion of NAD$^+$ using FK866 (FIG. 11L), an inhibitor of nicotinamide phosphoribosyltransferase (Nampt) that is required for the biosynthesis of NAD$^+$ (Bruzzone et al., 2009), resulted in a two-fold decrease in the frequency of IL17$^+$IFNγ$^+$ population in Th1/17 cells (FIG. 4C) and reduced expression of stemness-associated molecules such as Tcf7, Bcl6, and β-catenin (FIG. 4D). It was also observed that FK866-treated Th1/17 cells failed to exhibit potent tumor control upon adoptive transfer as compared to untreated Th1/17 cells (FIG. 4E), indicating that elevated levels of NAD$^+$ in Th1/17 cells is required for the maintenance of their anti-tumor activity and viability in vivo.

Figures 12A, 12B, 12C, 12D:
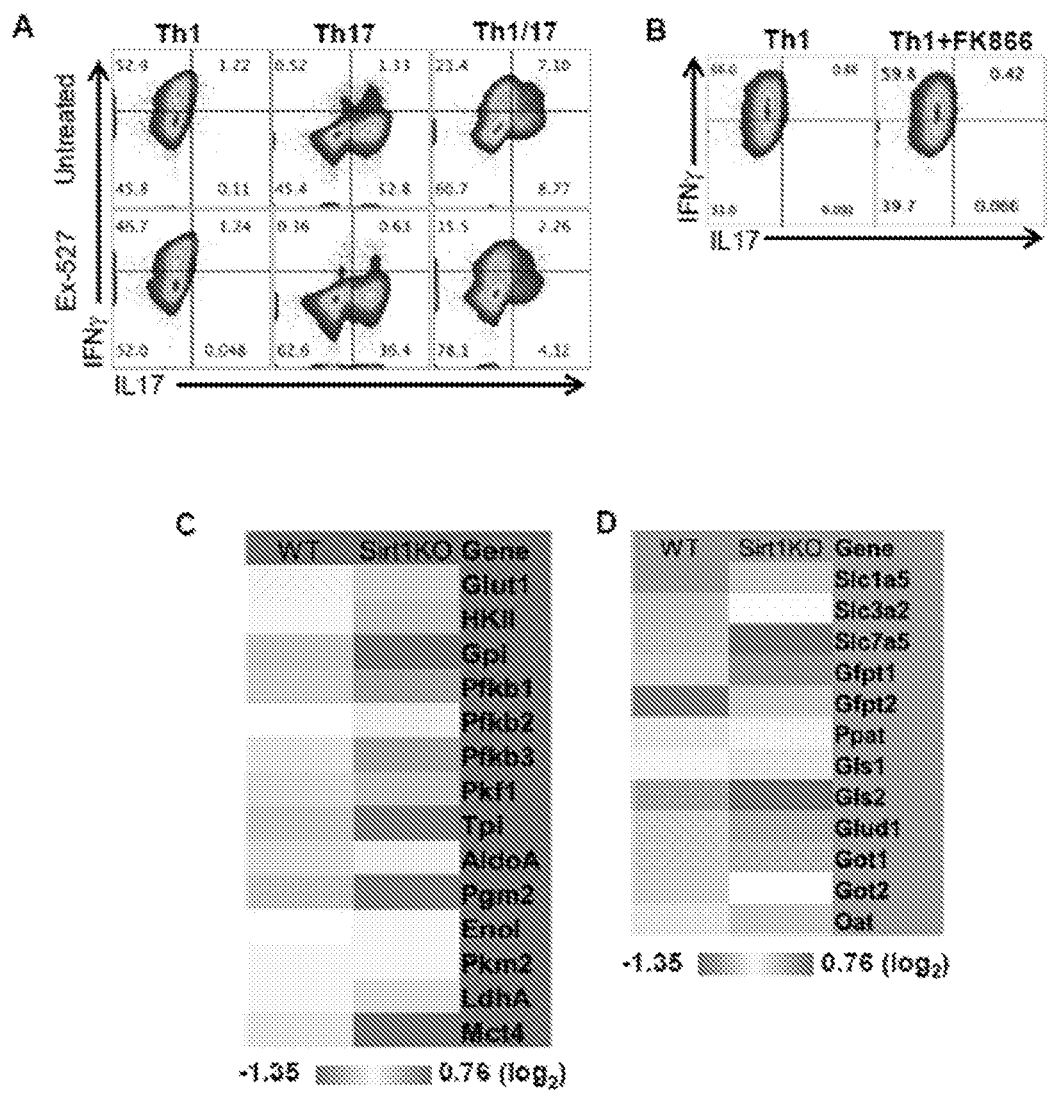
FIGS. 12A-12D: Loss of Sirt1 expression and NAD+ levels on Th1/17 cell phenotype and function (see FIG. 5). (A) Purified $CD4^+$ T cells from C57BL/6 were used to differentiate to Th1/17 cells either alone or in the presence of Ex527, a pharmacological inhibitor of Sirt1. Cells were then restimulated with PMA and ionomycin for 4 hr in presence of golgi block to stain for intracellular accumulation of cytokines IFNγ and IL17. (B) Th1 cells were cultured either in presence or absence of NAD+ inhibitor FK866 (10 nM) and intracellular staining was performed for IFNγ and IL17. Data was acquired using FACS and analysis was carried out using FlowJo software. (C-D) Purified splenic $CD4^+$ T cells from either C57BL/6 WT or Sirt1fl/flCD4Cre (Sirt1KO) mouse were used to ex vivo program for Th1/17 cells. RNA was prepared and quantitative PCR analysis was performed for the expression of various glycolysis (C) and glutaminolysis (D) associated genes in either WT or Sirt1KO Th1/17 cells. Data in section A-D are representative of three independent experiments.

NAD$^+$-Sirt1 axis is required to exert anti-tumor response by Th1/17 cells: Sirt1, an NAD$^+$ dependent protein deacetylase, acts as an epigenetic modulator of key transcription factors regulating immune cell function (Zhang and Kraus, 2010). It was observed that Sirt1 deacetylase activity was two-fold higher in Th1/17 cells (FIG. 5A), and a decreased frequency of IL17$^+$ population in both Th17 and Th1/17 cells was noticed when using Sirt1-KO T cells (FIGS. 5B and 5C), or programming WT T cells in the presence of Sirt1 pharmacological inhibitor Ex527 (FIG. 12A). No significant difference in IFNγ secreting fraction was observed with Ex527 or FK866 with Th1 subsets (FIGS. 12A and 12B).

Figures 5A, 5B, 5C, 5D, 5E, 5F, 5G:
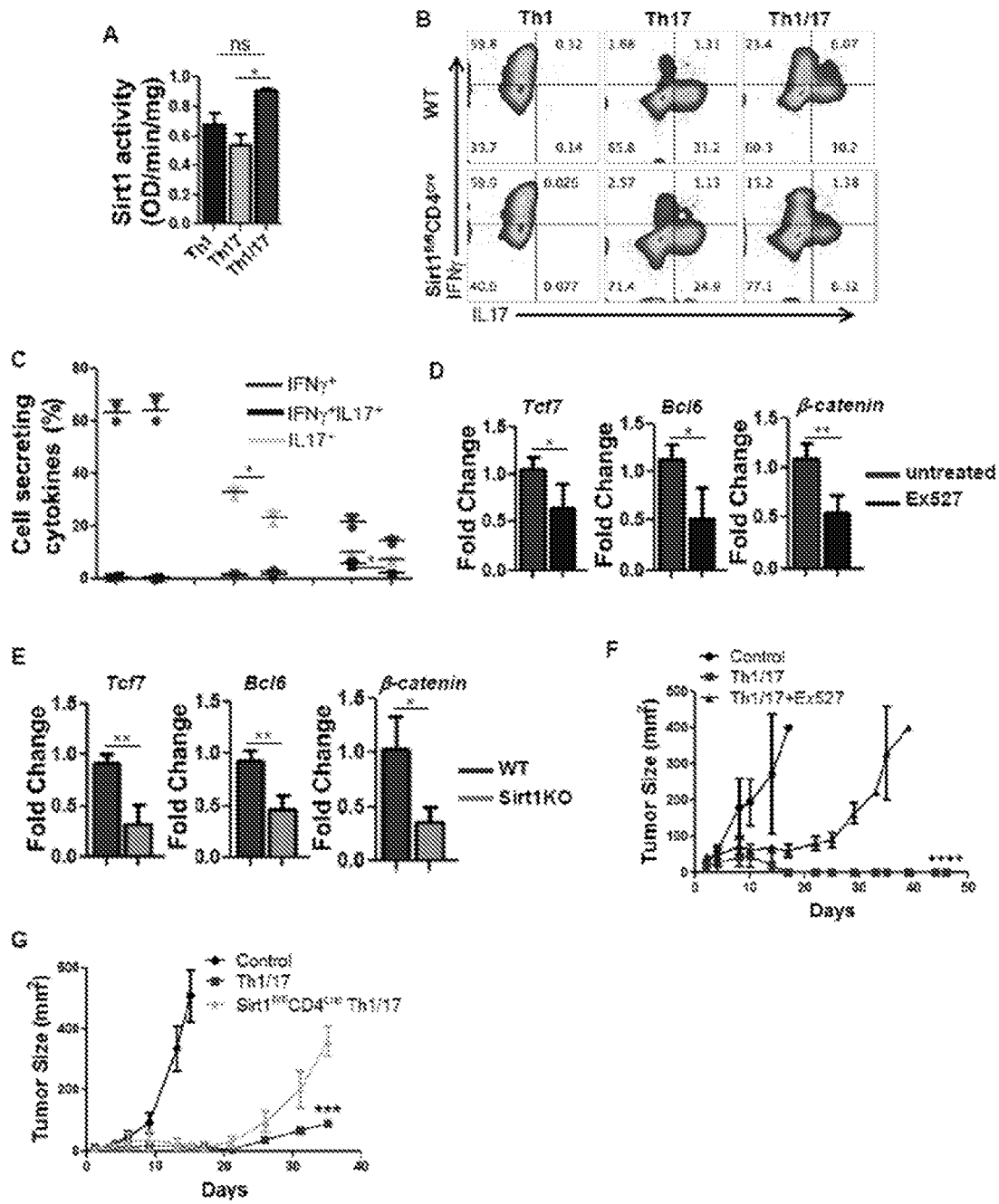
FIGS. 5A-5G: NAD-SIRT1 axis is central to Th1/17 anti-tumor response. Purified CD4$^+$ T cells differentiated to Th1, Th17 and Th1/17 were used for determining: (A) Sirt1 activity using equal amount of nuclear protein (10 μg). Data is presented as activity/mg of protein. (B-C) Flow cytometry analysis (B), and frequency (C) of Intracellular cytokines secretion after WT and Sirt1KO T cells were differentiated to Th1/17 cells. Th1/17 cells obtained from WT, Sirt1KO or WT differentiated in presence of Ex527 were used for: (D-E) determining expression of stemness associated genes, (F) B16-F10-HLA-A2$^+$ murine melanoma established s.c. for 9 days were treated by adoptively transferring $0.5\times10^6$ TIL13831 TCR transduced T cells differentiated to Th1/17 with or without Ex527, (G) B16-F10 murine melanoma established s.c. in C57BL/6 mice (n=5/group) for 9 days were treated by adoptively transferring $0.5\times10^6$ TRP-1 TCR transduced Th1/17 cells generated either from WT or Sirt-$1^{fl/fl}$CD4$^{Cre}$ mice. Tumor growth was measured using digital calipers every fourth day. Data in figure demonstrate mean tumor size at each time point. *$p<0.05$, $p<0.01$, *$p<0.005$ and ****$p<0.0001$.

Expression of the stemness-associated genes was also markedly reduced in Th1/17 cells when using Sirt1 pharmacological inhibitor (FIG. 5D) or Sirt1KO (FIG. 5E), suggesting that NAD$^+$-mediated Sirt1 activity is crucial for Th1/17 cells to exert their functionality and stemness phenotype. Since Sirt1 acts as a key metabolic sensor and regulates both glucose and lipid metabolism in various tissues (Li, 2013), it was next sought to determine whether high Sirt1 activity in Th1/17 cell endows them with the unique metabolic phenotype (i.e. Glutaminolysis$^{hi}$ Glycolysis$^{medium}$). However, qPCR analysis did not show a marked difference in the expression of key enzymes associated with different metabolic pathways in Th1/17 cells derived from WT vs. Sirt1KO (FIGS. 12C and 12D). This suggests that high Sirt1 activity in Th1/17 cells does not dictate their metabolic fate but rather acts downstream of NAD$^+$ to regulate the functionality and stemness phenotype of the cell. Further, melanoma epitope tyrosinase reactive hybrid Th1/17 cells (h3T CD4$^+$ T cells) differentiated ex vivo in the presence of Ex527 exhibited reduced ability to control tumor growth as compared to the vehicle treated cells (FIG. 5F). Similarly, Sirt-1$^{fl/fl}$CD4$^{Cre}$ mouse splenic T cells retrovirally transduced with TRP-1 TCR and programmed to hybrid Th1/17 phenotype exhibited reduced tumor control when adoptively transferred to the murine melanoma B16-F10 bearing mice (FIG. 5G). Thus, Sirt1 deacetylase activity is essential for the anti-tumor activity of hybrid Th1/17 cells.

Figures 6A, 6B, 6C, 6D, 6E, 6F, 6G, 6H, 6I, 6J, 6K:
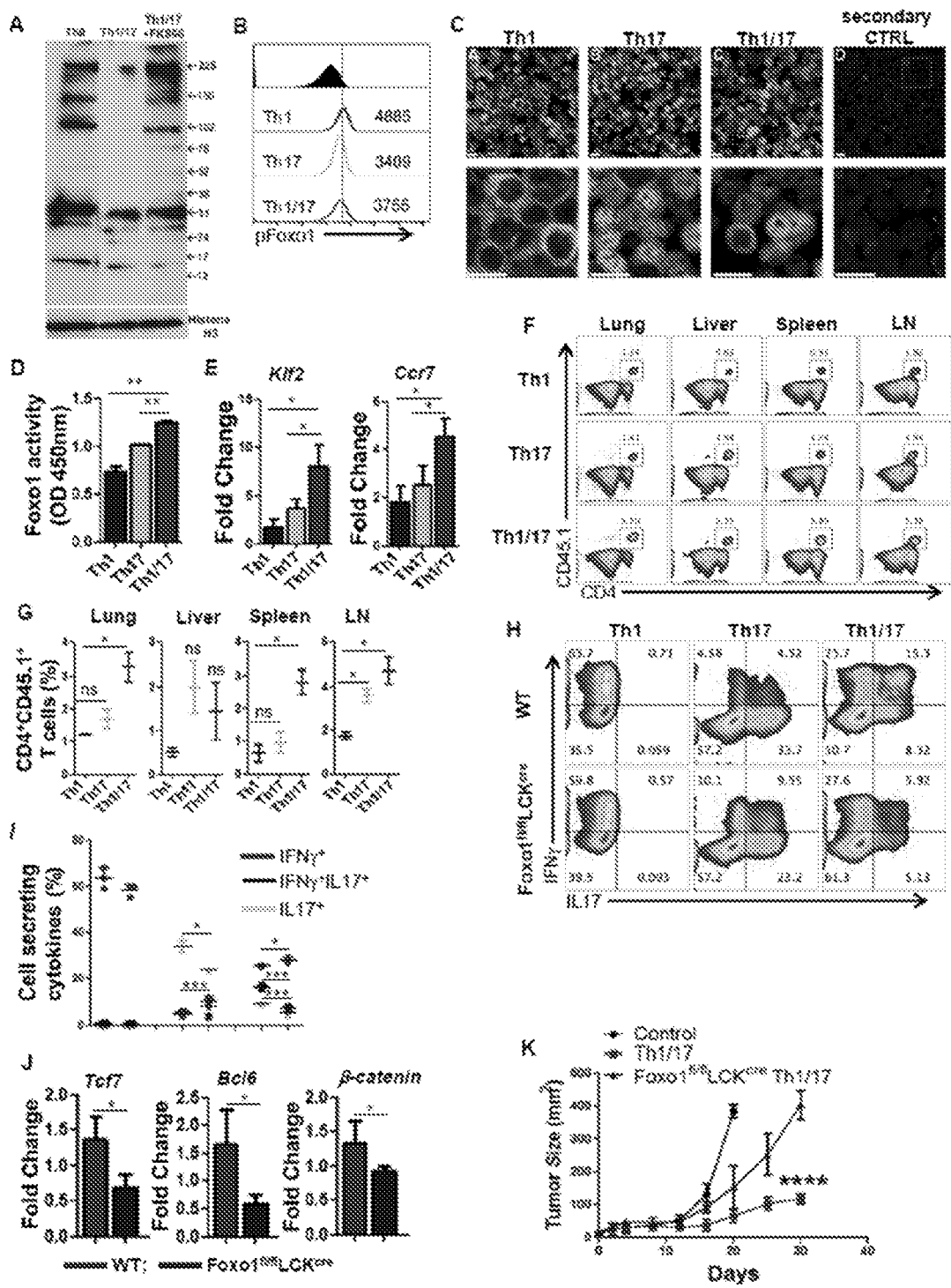
FIGS. 6A-6K: High Foxo1 activity in Th1/17 cell contributes to enhanced tumor control. (A) Determination of global acetylation of nuclear protein in Th0, Th1/17 and Th1/17+FK866 cells using western blot. Membrane was blotted for Histone H3 (bottom panel) for loading correction. (B) Flow cytometry analysis of phosphorylated Foxo1 (S256) in Th1, Th17 and Th1/17 cells. Data are representative of 3 independent experiments. (C) Confocal images of the indicated cell stained with Foxo1. Nuclei were stained with DAPI. Lower panels show the magnified images of the cells in the box drawn in the upper panels. Degree of Foxo1 retention in the nucleus is higher in Th17 cells followed by Th1/17 and Th1 cells. Bar=10 μm. (D) ELISA based determination of Foxo1 activity in Th1, Th17 and Th1/17 cells. Data are means±SD of 2 samples from 1 representative experiment out of 3 is shown. (E) qPCR analysis of the expression of Klf2 and Ccr7 in differentiated Th1, Th17 and Th1/17 cells. (F-G) Flow cytometric analysis (F) and frequency (G) of donor cells (Ly5.1$^+$) retrieved from the lung, liver, spleen and lymph nodes 24 hr after adoptive transfer of Th1, Th17 and Th1/17 cells into wild-type mice (Ly5.2$^+$). (H-J) WT or Foxo1$^{fl/fl}$Lck$^{cre}$ CD4$^+$T cells differentiated to Th1, Th17 and Th1/17 cells were used to determine: (G) intracellular cytokine secretion, (I) frequency of cells secreting cytokines and (J) stemness associated genes using qPCR. (K) C57BL/6 mice (n=4 mice/group) with subcutaneously established B16-F10 melanoma for 9 days were either kept untreated or adoptively transferred with $0.5\times10^6$ TRP-1 TCR transduced Th1/17 cells from either WT or Foxo1$^{fl/fl}$Lck$^{cre}$ mice. The tumor growth curve from various groups of recipient mice is shown. Data are representative of 3 independent experiment in H-J and from 2 independent experiments with similar result in I. *$p<0.05$, $p<0.01$, *$p<0.005$ and ****$p<0.0001$.
Figures 13A, 13B, 13C, 13D, 13E, 13F, 13G, 13H, 13I, 13J:
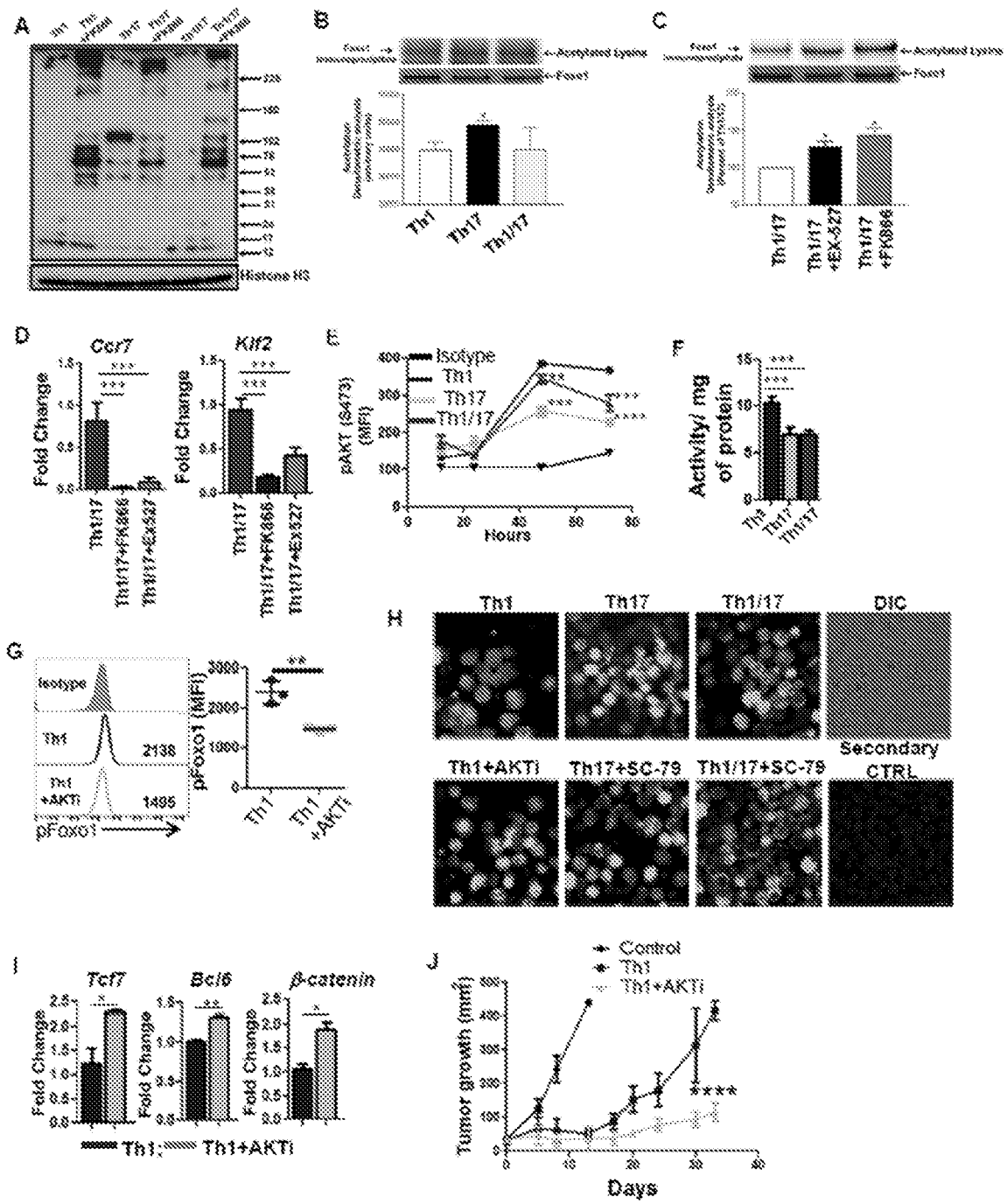
FIGS. 13A-13J: Acetylation levels of Foxo1 regulate Th1/17 phenotype and function (see FIG. 6). (A) Purified $CD4^+$ T cells differentiated to Th1, Th17 and Th1/17 (with or without $NAD^+$ inhibitor FK866) were used for determining global acetylation of nuclear protein using western blot, where membrane was probed with anti-acetylated lysine antibody followed by incubation with peroxidase conjugated secondary antibody. Membrane was blotted for Histone H3 (bottom panel) for loading correction. (B-C) Foxo1 immunoprecipitated from either (B) Th1, Th17 and Th1/17 cells or (C) Th1/17 cells treated with either Ex527 (10 µM) or FK866 (10 nM), using anti-Foxo1 monoclonal antibody for 16 h at 4° C. followed by incubation with Protein A/G-Sepharose for 1 h at 4° C. The immunoprecipitated Foxo1 was separated on 10% SDS-PAGE and then transferred to nitrocellulose membranes. The membranes were probed with anti-Acetyl-Lysine antibody (1:1000 dilution) followed by incubation with secondary antibody (HRP-conjugated goat anti-rabbit IgG at 1:3000 dilution) for 1 h at 20° C. as previously described. For chemiluminescent detection, the membranes were treated with enhanced chemiluminescent reagent (ECL), and the signal was monitored using a Biorad Versadoc imaging system (Biorad, Hercules, CA). Total Foxo levels in the samples are shown below the immunoprecipitation blot. Bars represent quantified differences in Foxo acetylation between samples. Data represent mean±SE; *p<0.05; n=3. (D) qPCR analysis for the expression of Klf2 and Ccr7 in Th1/17 cells differentiated either in presence or absence of FK866 (10 nM) or Ex527 (10 µM) was performed. (E) AKT phosphorylation (at S473) was determined in Th1, Th17 and Th1/17 cells using flow-cytometery. Mean fluorescence intensity (MFI) of pAKT (S473) at different time point is depicted, and statistical analysis determining the significance of reduction as compared to Th1 group is shown. p<0.01 and *p<0.005, ****p<0.001. (F) Purified $CD4^+$ T cells differentiated to Th1, Th17 and Th1/17 cells were used to determine the kinase activity of AKT using an ELISA based method flowing the manufacturer's protocol. Data are representative of 3 independent experiments with identical observation. (G) Purified $CD4^+$ T cells were differentiated to Th1 cells either in the presence or absence of AKT inhibitor (AKTi; 1 µM) and used for determining phosphorylation of Foxo1 (S257) by flow cytometry. Overlay plot with numerical values representing mean fluorescence intensity (MFI) from one representative experiment is shown. Cumulative data from three independent experiments with similar result is shown on right. (H) As in G), $CD4^+$ T cells were differentiated to Th17 and Th1/17 in the absence or presence of AKT activator SC-79 (0.5 µg/ml) before confocal imaging was performed to determine the localization of Foxo. Nuclei were stained with DAPI. Bar represents 10 µM. (I) Cells in G) were used to determine the expression of various stemness associated genes using qPCR, and (J) ability to control growth of s.c. established B16-F10-HLA-A2+ murine melanoma upon adoptive transfer. Tumor growth was measured using digital calipers every fourth day. Data in figure demonstrate mean tumor size at each time point in one of the two experiments with similar results. *p<0.05, p<0.01 and *p<0.005.

NAD$^+$ mediated Sirt1 deacetylase regulates Foxo1 activity, a key determinant of anti-tumor response of Th1/17 cells: Because the deacetylase activity of Sirt1 modulates the acetylation/deacetylation status of various transcription factors involved in the regulation of key cellular responses (Zhang and Kraus, 2010), the degree of acetylation was compared in hybrid Th1/17 cells. Using the global acetylation antibody that tracks the acetylation sites on the lysine residues, it was observed that Th1/17 cells indeed have reduced acetylation, which was reversed to a certain extent when NAD$^+$ levels were lowered due to Nampt inhibitor FK866 treatment (FIG. 6A, FIG. 13A). However, it was unclear if the anti-tumor property exhibited by Th1/17 cells was a synergistic effect of acetylation/deacetylation induced functional modulation of multiple proteins.

Given that Foxo1 has been implicated in the generation of T cell memory response, migration (Rao et al., 2012) and is regulated both by phosphorylation and acetylation levels (Daitoku et al., 2011), the next studies focused on evaluating this protein between the Th subsets. The Th1/17 cells exhibited intermediate level of Foxo1 phosphorylation (FIG. 6B). Since phosphorylation levels of Foxo1 facilitate its export from the nucleus to the cytoplasm, leading to its degradation and loss of transcriptional activity, this data suggests that Th1 cells have minimal nuclear retention of Foxo1, which could be the reason for their reduced memory or persistence as compared to Th17 and Th1/17 cells. The confocal imaging studies correlated with the phosphorylation data and showed that degree of Foxo1 retention in the nucleus is higher in Th17 cells followed by Th1/17 and Th1 cells (FIG. 6C). Analysis of Foxo1 acetylation, which correlates to attenuation of its transcriptional activity (Daitoku et al., 2004), showed reduced acetylation levels in Th1 and Th1/17 cells (FIG. 13B). Given that Th1 cells exhibit increased phosphorylation and reduced retention in the nucleus, it is likely that the cumulative activity of Foxo1 is higher in Th1/17 cells as compared to Th1 cells (despite having high NAD$^+$). A quantitative determination of the transcriptional activity of Foxo1 in Th subsets showed that Foxo1 activity was indeed highest in Th1/17 cells as compared to the Th1 and Th17 cells (FIG. 6D). Further, the elevated Foxo1 activity translated into higher expression of key Foxo1 targets as Klf2 and Ccr7 in Th1/17 cells as compared to Th17 and Th1 cells (FIG. 6E). This difference also led to functionally increased homing of Th1/17 cells to the lung, liver, spleen and lymph nodes after 24 hours of adoptive transfer into CD45.2$^+$ congenically different recipient (FIGS. 6F and 6G).

In further studies, pharmacological inhibition of NAD$^+$ and Sirt1 in Th1/17 cells not only resulted in increased acetylation in Th1/17 cells (FIG. 13C) but also resulted in decreased expression of the Foxo1 targets Klf2 and Ccr7 (FIG. 13D). This indicates that NAD$^+$ mediated Sirt1 activity regulates acetylation levels of Foxo1, which in turn affects its transcriptional activity and modulates the functional outcome of a T cell immune response. Differentiation of hybrid Th1/17 cells was also compromised when using splenic T cells from Foxo1$^{fl/fl}$Lck$^{Cre}$ mouse, as evident by decreased fraction of IL17$^+$IFNγ$^+$ (FIGS. 6H and 6I) and reduced expression of 'sternness' genes (FIG. 6J). Importantly, Foxo1$^{fl/fl}$Lck$^{Cre}$ derived T cells transduced with TRP-1 TCR and ex vivo programmed to Th1/17 phenotype also showed reduced ability to control tumor growth upon adoptive transfer (FIG. 6K). This data suggests that NAD$^+$-Sirt1 based modulation of Foxo1 activity plays a key role in hybrid Th1/17 cell migration, effector function, stemness and anti-tumor responses.

Next, it was sought to determine whether maintenance of transcriptionally active nuclear Foxo1 is a key regulator of anti-tumor property in general, and could ameliorate the anti-tumor response of Th1 cells (that exhibit high NAD$^+$ and Sirt1 but low nuclear Foxo1). Phosphorylation of AKT (S473) inversely correlates with the nuclear Foxo1 level, as its kinase activity phosphorylates Foxo1 and facilitates nuclear export (Rao et al., 2012). To interrogate whether reduced nuclear Foxo1 in Th1 cells is due to increased activity of AKT, both pAKT (S473) level and their kinase activity was determined in Th subsets. It was observed that pAKT (S473) level and their kinase activity are markedly elevated in Th1 cells as compared to Th17 and Th1/17 cells (FIGS. 13E and 13F). Next, the activity of AKT was inhibited in Th1 cells in order to block the phosphorylation of Foxo1. Inhibition of AKT in Th1 cells significantly reduced the phosphorylation of Foxo1 (FIG. 13G), and concomitantly increased its nuclear retention (FIG. 13H). Importantly, using Th17 and Th1/17 cells programmed in presence of AKT activator SC-79 showed reduced nuclear Foxo1 levels (FIG. 13H). The reduction of AKT in Th1 cells also led to upregulation of genes associated with memory response (FIG. 13I). Furthermore, Th1 cells cultured in the presence of AKTi also exhibited improved tumor control when compared with vehicle control treated Th1 cells (FIG. 13J). Thus, although Th1 cells have levels of NAD$^+$ comparable to Th1/17 cells, their inferior anti-tumor phenotype can be improved by inhibiting the AKT-Foxo1 circuit.

TABLE 1 p value for glycolytic genes expression in Th1, Th17, and Th1/Th17 cells (see FIG. 3)

| Gene name | Th1 vs. Th17 | Th1 vs. Th1/17 | Th17 vs. Th1/17 |
|---|---|---|---|
| Glucose transporter 1 (Glut1) | 0.04013 | 0.00181 | 0.96403 |
| Hexokinase 1 (HK1) | 0.15463 | 0.01092 | 0.80529 |
| Hexokinase 2 (HK2) | 0.05468 | 0.00251 | 0.94528 |
| Glucose-6-phosphate isomerase (Gpi) | 0.08248 | 0.07438 | 0.91092 |
| Phosphofructokinase b 1 (Pfkb1) | 0.01116 | 0.01188 | 0.12497 |
| Phosphofructokinase b 2 (Pfkb2) | 0.22222 | 0.22473 | 0.88340 |

TABLE 1-continued p value for glycolytic genes expression in
Th1, Th17, and Th1/Th17 cells (see FIG. 3)

| Gene name | Th1 vs. Th17 | Th1 vs. Th1/17 | Th17 vs. Th1/17 |
|---|---|---|---|
| Phosphofructokinase b 3 (Pfkb3) | 0.84016 | 0.78659 | 0.99723 |
| Phosphofructokinase 1 (Pfk1) | 0.00816 | 0.00261 | 0.17861 |
| Triose Phosphate isomerase (Tpi) | 0.01430 | 0.02120 | 0.10837 |
| Aldolase A | 0.04038 | 0.05181 | 0.80448 |
| Phosphoglycerate mutase 1 (Pgam1) | 0.04068 | 0.48843 | 0.00561 |
| Phosphoglucomutase 2 (Pgm2) | 0.09448 | 0.12308 | 0.05527 |
| Enolase (Eno1) | 0.00278 | 0.00909 | 0.12473 |
| Pyruvate kinase 2 (Pkm2) | 0.03252 | 0.03600 | 0.01143 |
| Lactate dehrodenase A (LdhA) | 0.01342 | 0.00862 | 0.04871 |
| Monocarboxylate transporter 4 (MCT4) | 0.01342 | 0.00862 | 0.04871 |

TABLE 2 p value for glutaminolysis genes expression
in Th1, Th17, and Th1/17 cells (see FIG. 3).

| Gene name | Th1 vs. Th17 | Th1 vs. Th1/17 | Th17 vs. Th1/17 |
|---|---|---|---|
| Solute carrier family 1 member 5 (Slc1a5) | 0.10571 | 0.01140 | 0.02497 |
| Solute carrier family 3 member 2 (Slc3a2) | 0.04713 | 0.03538 | 0.01239 |
| Solute carrier family 7 member 5 (Slc7a5) | 0.05303 | 0.01560 | 0.00765 |
| Glutamine-fructose-6-phosphate transaminase 1 (Gfpt1) | 0.00856 | 0.02245 | 0.00669 |
| Glutamine-fructose-6-phosphate transaminase 2 (Gfpt2) | 0.01416 | 0.15260 | 0.12616 |
| Phosphoribosyl pyrophosphate Aminotransferase (Ppat) | 0.01199 | 0.19293 | 0.01605 |
| Glutaminase 1(Gls1) | 0.35285 | 0.14691 | 0.09248 |
| Glutaminase 2 (Gls2) | 0.05839 | 0.09548 | 0.02848 |
| Glutamate dehydrogenase 1 (Glud1) | 0.90391 | 0.01053 | 0.01413 |
| Glutamate oxaloacetate transaminase 1 (Got1) | 0.04930 | 0.24485 | 0.02564 |
| Glutamate oxaloacetate transaminase 2 (Got2) | 0.17816 | 0.15652 | 0.00212 |
| Ornithine aminotransferase (Oat) | 0.04263 | 0.11451 | 0.02350 |

TABLE 3 p value for glutaminolysis genes expression
in WT and CD38KO CD4$^+$ T cells (FIG. 7).

| Gene name | WT vs. CD38KO CD4$^+$ T cells |
|---|---|
| Solute carrier family 1 member 5 (Slc1a5) | 0.113438 |
| Solute carrier family 3 member 2 (Slc3a2) | 0.045317 |
| Solute carrier family 7 member 5 (Slc7a5) | 0.021036 |
| Glutamine-fructose-6-phosphate transaminase 1 (Gfpt1) | 0.049051 |
| Glutamine-fructose-6-phosphate transaminase 2 (Gfpt2) | 0.057432 |
| Phosphoribosyl pyrophosphate Aminotransferase (Ppat) | 0.194268 |
| Glutaminase 1(Gls1) | 0.039745 |
| Glutaminase 2 (Gls2) | 0.043545 |
| Glutamate dehydrogenase 1 (Glud1) | 0.137267 |
| Glutamate oxaloacetate transaminase 1 (Got1) | 0.050179 |
| Glutamate oxaloacetate transaminase 2 (Got2) | 0.019091 |
| Ornithine aminotransferase (Oat) | 0.034764 |

TABLE 4

STAR methods.

| Gene | Forward | Reverse | Source |
|---|---|---|---|
| Mouse qPCR primers: 5'-3' | | | |
| Glut1 | CAGTTCGGCTATAACACTGGTG | GCCCCCGACAGAGAAGATG | IDT, Coralville |
| HKI | CGGAATGGGGAGCCTTTGG | GCCTTCCTTATCCGTTTCAATGG | IDT, Coralville |
| HKII | GGAACCGCCTAGAAATCTCC | GGAGCTCAACCAAAACCAAG | IDT, Coralville |
| Gpi | TCAAGCTGCGCGAACTTTTTG | GGTTCTTGGAGTAGTCCACCAG | IDT, Coralville |
| Pfkb1 | ATGAGCTGCCCTATCTCAAGT | GTCCCGGTGTGTGTTCACAG | IDT, Coralville |
| Pfkb2 | GACAAGCCAACTCACAACTTCC | ACACTGTAATTTCTTGGACGCC | IDT, Coralville |
| Pfkb3 | CCCAGAGCCGGGTACAGAA | GAGCCCCACCATCACAATCAC | IDT, Coralville |
| Pfk | AGGAGGGCAAAGGAGTGTTT | TTGGCAGAAATCTTGGTTCC | IDT, Coralville |
| TpI | CTTACATCGACTTTGCCAGACA | CTAGGGCGTGGCTCACTTT | IDT, Coralville |
| AldoA | TCAGTGCTGGGTATGGGTG | GCTCCTTAGTCCTTTCGCCT | IDT, Coralville |
| Pgam1 | TCTGTGCAGAAGAGAGCAATCC | CTGTCAGACCGCCATAGTGT | IDT, Coralville |
| Pgm2 | AGTGAAGACGCAGGCATATCC | GGCTCCACGGTAGAGACGA | IDT, Coralville |
| Eno1 | AAAGATCTCTCTGGCGTGGA | CTTAACGCTCTCCTCGGTGT | IDT, Coralville |
| Pkm2 | GTCTGAATGAAGGCAGTCCC | GTCCGCTCTAGGTATCGCAG | IDT, Coralville |
| LdhA | TGTCTCCAGCAAAGACTACTGT | GACTGTACTTGACAATGTTGGGA | IDT, Coralville |
| MCT4 | TCACGGGTTTCTCCTACGC | GCCAAAGCGGTTCACACAC | IDT, Coralville |
| Slc1a5 | GGACGTCTTCTATCTCCACAA | ACTCCTTCAATGATGCCACC | IDT, Coralville |
| Slc3a2 | TGCAACCAAGAACTCAGAGC | TCATTTTGGACCTCACTCCC | IDT, Coralville |
| Slc7a5 | ACAGCTGTGAGGAGCAGCAC | TCTTCGCCACCTACTTGCTC | IDT, Coralville |
| Gfpt1 | GCCAACGCCTGCAAAATCC | GCCCAACGGGTATGAGCTAT | IDT, Coralville |
| Gfpt2 | TGATGGGAATAACCACGAAGTCA | CGAAGTGTGTCTCAAACTCCAC | IDT, Coralville |
| Ppaf | GGGAGTGCAGTGCCTAAATTC | GTACCTCGTATGTCCGATTCCA | IDT, Coralville |
| Gls | GCTGTGCTCTATTGAAGTGACA | TTGGGCAGAAACCACCATTAG | IDT, Coralville |
| Gls2 | TGCATATAGTGGAGATGTCTCG | GCTCCATATCCATGGCCGACAA | IDT, Coralville |
| Glud1 | CCCAACTTCTTCAAGATGGTGG | AGAGGCTCAAACACATGGTTGC | IDT, Coralville |
| Got1 | ACCGCACAGATGAATCTCAGC | ATGGGCAGGTACTCGTGGT | IDT, Coralville |
| Got2 | TGGGCGAGAACAATGAAGTGT | CCCAGGATGGTTTGGGCAG | IDT, Coralville |
| Oaf | TGCCACCCAAAGATCATAGATGC | TGTACTCCTCGTATTCACCAAGG | IDT, Coralville |
| Kif2 | CTCAGCGAGCCTATCTTGCC | CACGTTGTTTAGGTCCTCATCC | IDT, Coralville |

TABLE 4-continued

STAR methods.

| Gene | Forward | Reverse | Source |
|---|---|---|---|
| CCR7 | GTCTCTCTCCAGCTAGCCCA | CAAACAGGAGCTGATGTCCA | IDT, Coralville |
| Cpt1a | TCTATGAGGGCTCGCG | CGTCAGGGTTGTAGCA | IDT, Coralville |
| PGC1α | TGAGGACCGCTAGCAAGTTT | TGTAGCGACCAATCGGAAAT | IDT, Coralville |
| Csf2 | GGCCTTGGAAGCATGTAGAGG | GGAGAACTCGTTAGAGACGACTT | IDT, Coralville |
| IL23r | TTCAGATGGGCATGAATGTTTCT | CCAAATCCGAGCTGTTGTTCTAT | IDT, Coralville |
| IL22 | ATGAGTTTTTCCCTTATGGGGAC | GCTGGAAGTTGGACACCTCAA | IDT, Coralville |
| GzmB | GCCCACAACATCAAAGAACAG | AACCAGCCACATAGCACACAT | IDT, Coralville |
| Tbx21 | AGCAAGGACGGCGAATGTT | GGGTGGACATATAAGCGGTTC | IDT, Coralville |
| Tcf7 | GTGGACTGCTGAAATGTTCG | AGCATCCGCAGCCTCAAC | IDT, Coralville |
| Bcl6 | GATACAGCTGTCAGCCGGG | AGTTTCTAGGAAAGGCCGGA | IDT, Coralville |
| β-catenin | ATGGAGCCGGACAGAAAAGC | CTTGCCACTCAGGGAAGGA | IDT, Coralville |
| β-actin | ACGTAGCCATCCAGGCTGGTG | TGGCGTGAGGGAGAGCAT | IDT, Coralville |

Human qPCR primer: 5'-3'

| Tcf7 | AGAGAGAGAGTTGGGGGACA | TCTGCTCATGCATTACCCAC | IDT, Coralville |
| Bcl6 | CTGGCTTTTGTGACGGAAAT | GTTTCCGGCACCTTCAGACT | IDT, Coralville |
| Lef1 | CACTGTAAGTGATGAGGGGG | TGGATCTCTTTCTCCACCCA | IDT, Coralville |
| CD62L | CTTTCACCAAGGGCGATTTA | GGCATTTATCATTTGGCTGG | IDT, Coralville |
| Hprt1 | TTTGCTTTCCTTGGTCAGGC | GCTTGCGACCTTGACCATCT | IDT, Coralville |

Figures 7A, 7P:
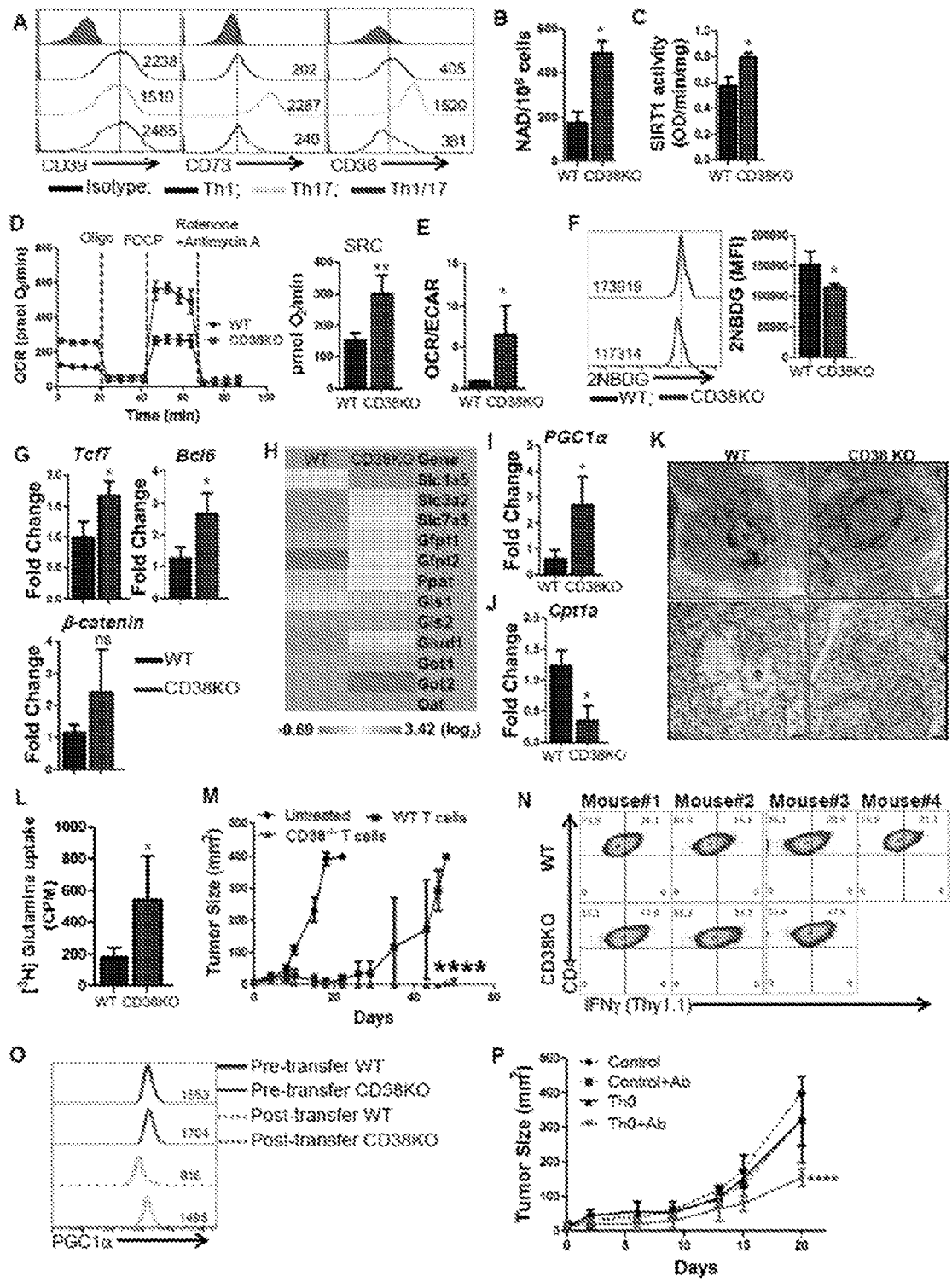
FIGS. 7A-7P: Inverse correlation between CD38 and NAD regulates anti-tumor property of T cells. (A) Purified CD4$^+$ T cells differentiated to Th1, Th17 and Th1/17 were used for determining the relative expression of cell surface molecules involved in canonical and non-canonical adenosinergic pathways. Splenic CD4+ T cells from C57BL/6 WT and CD38KO mice after 3 day of TCR activation was used to determine: (B) intracellular NAD+ levels, and (C) nuclear Sirt1 activity. TCR activated WT and CD38KO CD4+ T cells were used for determining: (D) time course of OCR (left panel), and SRC (right panel), and (E) basal OCR/ECAR ratio. (F) Glucose uptake by using fluorescent labelled glucose analogue 2-NBDG. Adjacent bar diagram represents the cumulative data of mean fluorescence intensity (MFI) from 3 independent experiments. (G-J) qPCR analysis of the expression of (G) various stemness associated genes, (H) Glutaminolysis associated genes (CD38KO T cells showed enhanced expression of glutaminolysis pathway genes), (I) PGC1a expression and (J) Cpt1a expression. (K) Transmission Electron Microscopy of activated WT and CD38KO CD4+ T cells. Lower panels show the magnified images of the cells in the box drawn in the upper panels. Bar=1 µM (upper panel) and 200 nM (Lower panel). (L) Uptake of radiolabelled glutamine measured in count per minute (CPM) is presented from 1 of 2 independent experiments. (M) Anti-tumor ability upon adoptive transfer of $0.5\times10^6$ tyrosinase reactive TIL1383I TCR transduced CD4+ T cells from either C57BL/6 IFNγ$^{Thy1.1}$ or CD38KO-IFNγ$^{Thy1.1}$ mice to HLA-A+ mice (N=8/group) with s.c. established B16-F10-HLA-A2+ murine melanoma cells. Data from 1 of the 2 experiments with similar results is shown. (N) Tumor infiltrating lymphocytes from the treated mice (as in M) were retrieved and expression of Thy1.1 (≈IFN-γ) was evaluated in CD4+Vβ12+ cells using flow cytometry. (O) Flow cytometry analysis for intranuclear expression of PGC1α was performed using the WT or CD38KO CD4+ T cell retrieved 24 hr after injection to the ascites of EL-4 ascites tumor bearing mice (n=2). PGC1α expression pre- and post-injection is shown. (P) C57BL/6 mice (n=4-5 mice/group) with 9 days subcutaneously established B16-F10 melanoma tumor were either kept untreated or adoptively transferred with 1×10$^6$ TRP-1 CD4+ T cells (Th0). Group of mice that received T cells were either kept untreated or injected with anti-CD38 Ab (50 µg/mouse; i.p.) 3 times in a week up to day 20. Shown is the tumor growth curve of various groups of recipient mice. *p<0.05, p<0.01, *p<0.005 and ****p<0.0001.

Inverse correlation between CD38 and NAD+ controls long-term anti-tumor response by T cells. Recent studies have implicated that in addition to being a part of non-canonical adenosinergic pathway (Morandi et al., 2015), the cell surface molecule CD38 is also a NADase and its expression inversely correlates with NAD+ levels (Chini, 2009). While the expression of CD38 was found to be upregulated on Th17 cells, hybrid Th1/17 cells exhibited reduced expression of CD38 and other ectonucleotidases (CD39, CD73) (FIG. 7A). Further, TCR activated CD38KO T cells showed intrinsically higher NAD+ and Sirt1 activity (FIGS. 7B and 7C) that also correlated with significantly higher OCR and spare respiratory capacity as compared to WT T cells (FIG. 7D). The preferential dependence of CD38KO T cells on OXPHOS was evident by their higher OCR/ECAR ratio as compared to WT T cells (FIG. 7E).

Figures 14A, 14T:
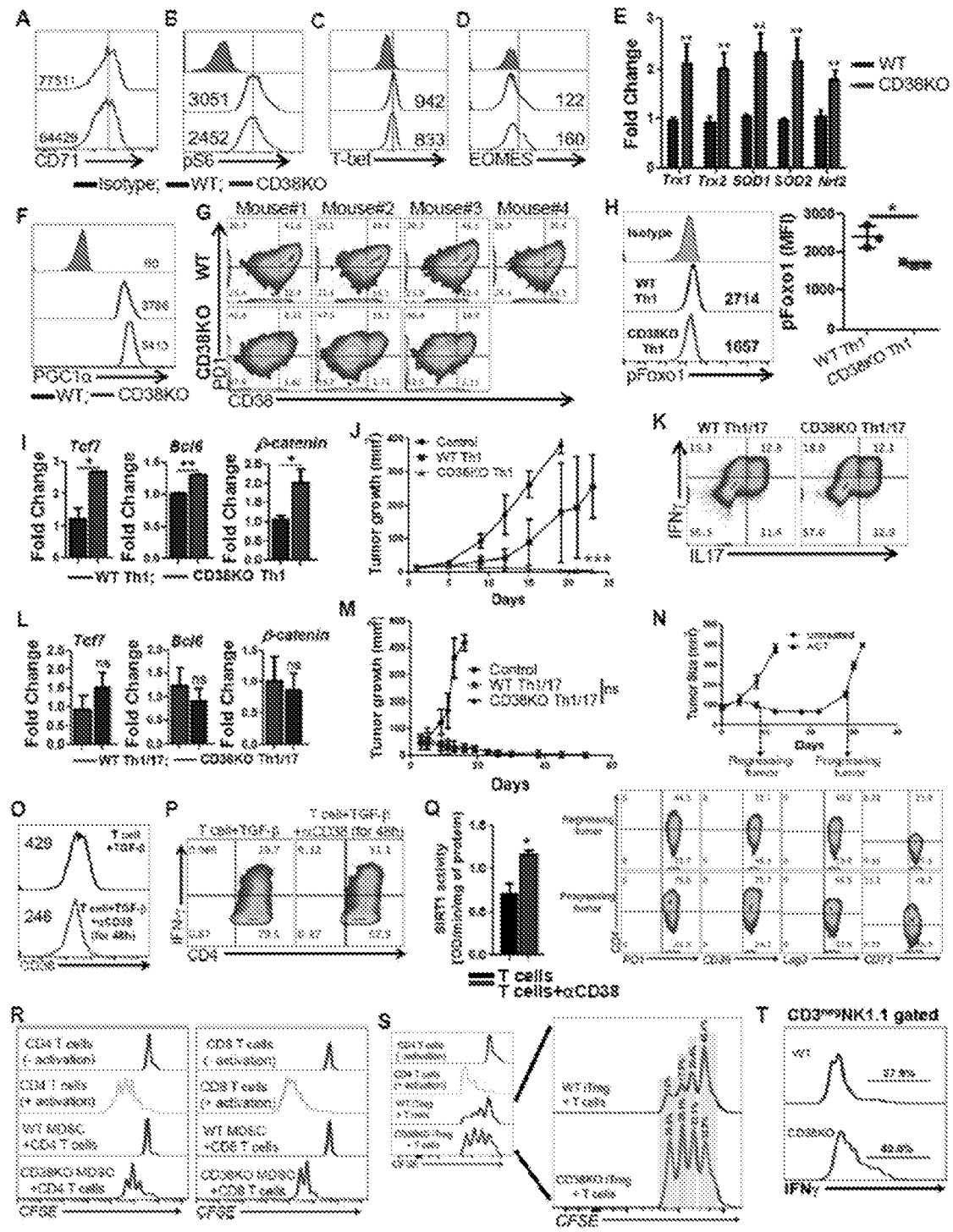
FIGS. 14A-14T: Inverse correlation between CD38 and NAD+ regulates anti-tumor property of T cells (see FIG. 7). (A-F) Splenic T cells from WT or CD38KO were used for TCR mediated activation using anti-CD3 and anti-CD28 for three days in presence of rIL2 (50 units/ml). Activated cells were then used for various assays. Flow cytometry based analysis for the cell surface expression of (A) CD71, (B) intracellular expression of pS6, (C) T-bet and (D) EOMES. (E) qPCR analysis of the expression of various anti-oxidant genes, and (F) flow cytometry analysis of the intracellular expression of PGC1α. Numerical values in A-D and F are mean fluorescence intensity. (G) $CD4^+$ T cells from either WT or CD38KO IFNγThy1.1 knock in mice were retrovirally transduced with TIL1383I TCR and adoptively transferred ($0.5 \times 10^6$ cells/mouse) to HLA-A2$^+$ mice with ten days subcutaneously established B16-F10-HLA-A2$^+$ melanoma tumors. TILs were retrieved and expression of PD1 vs. CD38 was evaluated on transferred CD4$^+$ Vβ12$^+$ TIL1383I TCR specific cells using flow cytometry. (H-J) Purified CD4$^+$ T cells from either WT or CD38KO mice differentiated to Th1 cells were used for determining: (H) phosphorylation of Foxo1 (S257) by flow cytometry. Scatter plot representing cumulative data for mean fluorescence intensity (MFI) from three independent experiments. (I) qPCR analysis of various stemness associated genes was performed on samples used in parallel experiments in H. (J) ability to control the growth of 10 days subcutaneously established B16-F10 melanoma tumor in C57BL/6 mice (n=4 mice/group) upon adoptive transfer of either WT or CD38KO TRP-1 TCR transduced Th1 cells ($0.5 \times 10^6$ cells/mouse). Tumor growth curve averaged from different mice in various experimental groups of recipient mice is shown. (K-L) Purified CD4$^+$ T cells from either WT or CD38KO mice differentiated to Th1/17 cells were used to determine: (K) intracellular cytokine secretion after re-stimulating them with PMA and ionomycin for 4 hr; (L) qPCR based mRNA levels for key stemness associated genes; (M) ability to control the growth of 10 days subcutaneously established B16-F10 melanoma tumor in C57BL/6 mice (n=4mice/group) upon adoptive transfer of either WT or CD38KO TRP-1 TCR transduced Th1/17 cells ($0.5 \times 106$ cells/mouse). Tumor growth curve averaged from different mice in various experimental groups of recipient mice is shown. (N) CD4$^+$ TRP-1 T cells were activated in vitro for 3 days and adoptively transferred ($1 \times 106$ cells/mouse) in a group of 8 mice with subcutaneously established B16-F10 melanoma tumors. A group of 4 mice were euthanized either on day 8 or day 28 post ACT (upper panel) and TILs were retrieved from the tumor site to evaluate for the expression of various negative regulatory molecules within the CD4$^+$ Vβ14$^+$ gate using flow cytometry (lower panel). (O-Q) C57BL/6 (WT) derived splenic CD4$^+$ T cells were activated for three days in presence of TGF-β (1 ng/ml) and treated with or without of anti-CD38 (5 μg/ml) antibody for last 48 h of culture. Activated cells from these groups were then used for flow cytometric analysis to determine the expression of CD38 (O), intracellular staining of IFNγ (P), and nuclear Sirt1 activity (Q). (R-T) WT T cells labelled with CFSE (1 μM) were co-cultured at 1:1 ratio with either (R) MDSCs isolated from the tumor site of WT or CD38KO mouse, or (S) in vitro differentiated iTreg from WT or CD38KO for three days in presence of anti-CD3 (1 μg/ml) and anti-CD28 (1 μg/ml). T cells without anti-CD3 and anti-CD28 activation were kept as control. Suppression of T cell proliferation was determined by CFSE dilution using flow cytometry. Numerical values in R represent percent proliferating cells that correspond to each division. (T) Activated NK cells (CD3-NK1.1$^+$) from either WT or CD38KO mice were stimulated for 5 h with PMA and ionomycin on day four of the culture, and intracellular cytokine secretion was evaluated by flow cytometry. Numerical values represent percent IFNγ secreting cells. Data presented in sections A-E, H-I, J, K-L and N-T are representative of three experiments, whereas data in section F is from one in four independent experiment with similar results. *$p<0.05$, $p<0.01$ and *$p<0.005$.

A comparative analysis of key metabolic regulators identified reduced glucose uptake (measured using 2-NBDG) (FIG. 7F), CD71 (FIG. 14A), pS6 (FIG. 14B), T-bet (FIG. 14C), and increased expression of Eomes (FIG. 14D) in CD38KO T cells as compared to WT T cells. Further, CD38KO T cells also exhibited increased expression of the antioxidant genes (thioredoxin1, thioredoxin2, SOD1, SOD2 and Nrf2) (FIG. 14E) and genes associated with stem-cell like phenotypes (e.g., Tcf7, Bcl6 and β-catenin) (FIG. 7G). As observed for hybrid Th1/17 cells, the CD38KO T cells also showed similar metabolic gene signature with enhanced expression of glutaminolysis pathway genes (FIG. 7H) and mitochondrial biogenesis regulator PGC1α (FIG. 7I and FIG. 14F), whereas the expression of FAO regulator Cpt1α was significantly reduced (FIG. 7J). Increased expression of PGC1α also correlated with a higher mitochondrial number in CD38KO T cells relative to WT T cells as determined by electron microscopy (FIG. 7K). Dependence on the glutaminolysis pathway also correlated with increased uptake of radiolabelled glutamine by CD38KO T cells as compared to the WT T cells (FIG. 7L). Further, subcutaneously established murine melanoma B16-F10 treated by adoptively transferring TRP-1 TCR transduced Th0 cells (i.e. activated for three days in presence of IL2) obtained from either WT (i.e. IFNγ$^{Thy1.1}$ knock-in reporter) or CD38KO/IFN=$^{Thy1.1}$ mice showed that even in absence of ex vivo programming, CD38-KO derived Th0 cells could efficiently control tumor growth (FIG. 7M).

It was also observed that there was almost a 50% reduction in the cytokine secretion from WT T cells infiltrating tumors as compared to the CD38KO T cells (FIG. 7N). Thus, maintaining increased NAD+ by limiting the induced expression of CD38 on T cells renders them with a phenotype to persist longer and maintain anti-tumor function. Importantly, the expression of exhaustion molecule PD1 was not much different between the tumor infiltrating WT or CD38KO T cells (FIG. 14G). This implies that CD38 expression plays a key role in metabolically modulating even PD1-expressing exhausted T cells.

Given a recent report that blockade of PD1 is not sufficient to reverse mitochondrial insufficiency observed in tumor infiltrating lymphocytes (TILs) (Scharping et al., 2016), it was postulated that it is the expression of CD38 on the PD1 expressing T cells which regulates its metabolism. This idea was confirmed when the CD38-KO T cells did not lose functionality and maintained higher levels of PGC1a as compared to WT T cells after overnight exposure to EL4 tumor ascitis (FIG. 7O). Thus, it is likely that CD38 mediated NAD+level is key for maintaining PGC1α expression in the TILs. Further analysis of Th1 cells differentiated using CD38KO splenic T cells showed reduced pFoxo1 (FIG. 14H), increased expression of sternness associated genes (FIG. 14I), and improved tumor control (FIG. 14J) compared to WT Th1 cells. However, when CD38KO T cells were used to program hybrid Th1/17 cells no difference was observed in cytokine secretion profile (FIG. 14K), sternness genes expression (FIG. 14L) or in vivo tumor control (FIG. 14M). This suggests that increasing NAD+ could be key for improving the functionality of any Th subset, and ex vivo programming to hybrid phenotype leads to high NAD+ that equates with intrinsic NAD+ levels achieved by CD38 downregulation.

Since adoptively transferred T cells could acquire TGF mediated CD38 expression in a tumor microenvironment (FIG. 14N) which may lead to reduced NAD+ levels, it was posited that combining anti-CD38 antibody along with adoptive transferred T cells would enhance anti-tumor response. After co-culturing murine anti-CD38 antibody and purified T cells with TGFβ1 (to mimic tumor suppressive microenvironment and induce CD38), the initial in vitro data shows that T cells activated in the presence of anti-CD38 antibody exhibit reduced CD38 expression (FIG. 14O), increased cytokine secretion (FIG. 14P), and higher Sirt1 activity (FIG. 14Q). Importantly, the mice treated with combination of anti-CD38 antibody (Fab fragment) and T cells exhibited durable tumor control and longer survival as compared to those that were either treated with anti-CD38 antibody alone or the T cells alone (FIG. 7P). Thus, strategies that lower CD38 expression enhance T cell mediated tumor control.

The data showed that a hybrid Th1/17 subset has a significantly improved anti-tumor activity compared to Th1 or Th17 cells. Importantly, hybrid Tc1/17 cells also exhibited potent anti-tumor phenotype The long persisting hybrid T cells exclusively secreted IFNγ, and showed loss of anti-tumor phenotype upon blocking IFNγ. Thus, the strategy to generate both Th1/17 and Tc1/17 cells using similar programming conditions is of translational value, since it will overcome the current limitation where Th17 cells are better at anti-tumor activity than Th1 cells (Muranski et al., 2008), and Tc1 are better than Tc17 cells (Yu et al., 2013).

Example 2

Materials and Methods

Mice: C57BL/6, B6-HLA-A2$^+$, B6-Rag$^{-/-}$, CD38KO, Sirt1$^{fl/fl}$, CD4$^{cre}$, B6 (CD45.1), IFNγ$^{-/-}$, TRP-1, Pmel, TRAMP mice were obtained from Jackson Laboratory (Bar Harbor, ME). IFNγ$^{Thy1.1}$ knock-in, Foxo1$^{fl/fl}$Lck$^{cre}$ and T Ag TCR-I mice were kind gift from Casey T. Weaver, UAB, Melanie Gubbels Bupp, Randolph-Macon College, VA and Jennifer Wu, MUSC respectively. CD38KO-IFNγ$^{Thy1.1}$ knock-in mice, HLA-A2$^+$-Rag$^{-/-}$ mice and Pmel-IFNγ$^{-/-}$ mice were developed in the lab. Melanoma epitope tyrosinase reactive HLA-A2 restricted TCR transgenic mouse (referred as h3T in the text) was developed in the lab and reported earlier (Mehrotra et al., 2012). Animals were maintained in pathogen-free facilities and experimental procedures were approved by Institutional Animal Care and Use Committees of Medical University of South Carolina, Charleston. Mice were bred and housed under standard housing conditions (group housing up to 5 mice per cage) except B6-Rag$^{-/-}$ and HLA-A2$^+$-Rag$^{-/-}$ mice which require high barrier facility (also group housing up to 5 mice per cage). For tumor experiments, equal number of age and gender matched (both male and female) mice were randomly assigned for the experiments when they were between 8-10 weeks old. No influence of sex on the result of the studies was observed.

Cell Lines: B16-F10 (RRID: CVCL_0159) was obtained from American Type Culture Collection (ATCC), suggested to be of male origin.

T cell differentiation: Naïve CD4$^+$ T cells were purified from the total splenocytes of 6-9 weeks old WT (C57BL/6) and KO (Foxo1$^{fl/fl}$Lck$^{cre}$, Sirt1$^{fl/fl}$CD4$^{cre}$, CD38KO) mice using CD4$^+$ T cell isolation kit (Miltenyi Biotec) according to manufacturer's protocol. Total splenocytes from 6-9 weeks old TCR transgenic mouse TRP-1 (bears class-II restricted CD4$^+$ T cells) or Pmel (bears class-I restricted CD8$^+$ T cells) or TCR-I (bears class-I restricted CD8$^+$ T cells) were also used. Within experiments mice were age and sex matched. Purified naïve CD4$^+$ T cells or total splenocytes were differentiated to Th1 or Tc1 (10 ng/ml IL12, 50 U/ml IL2 and 10 µg/ml anti-IL4), Th17 or Tc17 (3 ng/ml TGFβ, 25 ng/ml IL6, 10 µg/ml anti-IL4 and 10 µg/ml anti-IFNγ), Th1/17 or Tc1/17 (20 ng/ml IL1β, 25 ng/ml IL6, 10 ng/ml IL12, 20 ng/ml IL23, 400 pg/ml TGFβ, 10 µg/ml anti-IL4, 5 µg/ml anti-IFNγ), iTreg (5 ng/ml TGFβ, 100 IU/ml IL2, 10 µg/ml anti-IL4 and 10 µg/ml anti-IFNγ or Th0 (50 IU/ml IL2) in presence of plate bound anti-CD3 (5 µg/ml) and anti-CD28 (5 µg/ml). For TRP-1, gp100 or Sv40 specific generation of different Th or Tc subsets, total splenocytes from either TRP-1, Pmel or TCR-I TCR transgenic mice were stimulated with 1 µg/ml respective peptides in presence of above-mentioned polarizing conditions. T cells were differentiated for three days in IMDM media supplemented with 10% FCS, 4 mM L-glutamine, 100 U/ml penicillin, 100 µg/ml streptomycin, 55 µM beta-mercaptoethanol under 7% CO$_2$, atmospheric oxygen at 37° C. in a humidified incubator. For evaluation of intracellular cytokines by flow cytometry, T cells were re-stimulated with PMA (500 ng/ml) and Ionomycin (500 ng/ml) for 4 hr in presence of Glogi inhibitors. In some experiments, in vitro differentiated T cells were either treated with the vehicle control or inhibitor of AKT, AKTi (1 µM; added into the differentiation media from day 0) or activator of AKT, SC-79 (0.5 µg/ml; added into the differentiation media for last 24 hr) or FK866 (10 nM; added into the differentiation media from day 0) or Ex527 (10 µM; added into the differentiation media from day 0) or 2DG (1 mM; added into the differentiation media from day 0) or DON (3 µM; added into the differentiation media from day 0).

Retroviral Transduction: One day before transfection, 5×10$^6$ Platinum-E ecotropic packaging cells (Cell Biolabs) were seeded in 10 ml antibiotic-free medium in 100 mm dishes (Corning). Packaging cells were transfected with 18 µg retroviral plasmid DNA encoding either the TIL 13831 TCR or the MSGV-1 TRP-1 TCR and the helper plasmid pCL-Eco using 36 µl Lipofectamine 2000 in OptiMEM (Invitrogen). After 24 hr, medium was replaced and the cells were incubated for additional 24 hr, after which the retrovirus-containing supernatant was collected and filtered. The viral supernatant was spun at 2,000 g for 2 hr at 32° C. onto non-tissue-culture-treated 24-well plates (USA Scientific) coated overnight with Retronectin (Takara Bio). Freshly isolated mouse CD4$^+$ T cells were activated with CD3/CD28-coated beads (Dynabeads, Life Technologies) at a 1:1 bead:cell ratio along with either T cell differentiation media (as described above) or IL2 containing media (100 U/ml) the same day as packaging cell transfection. Beads were removed 48 hr post-activation, just prior to transduction, and re-suspended to a concentration of 2×10$^6$ cells ml$^{-1}$ in fresh medium. After removing the virus from the Retronectin-coated plate following the first spin, 1 ml of the activated T cells were then plated in the same wells and 1 ml of fresh virus was added on top of the cells. The plate was spun for an additional 2 hr at 1100 g, 32° C. Post-spin, 1 ml of media was removed and replaced with fresh media containing 200 IU IL-2 ml$^{-1}$ before the cells were incubated overnight. The following day the cells were collected, washed and plated at 0.8-1×10$^6$ cells ml$^{-1}$.

Adoptive T cell protocol: B16-F10 or B16-F10-A2$^+$ mouse melanoma tumor cells (2.5×10$^6$) were injected subcutaneously (s.c.) into left flank of 8-10 weeks old C57BL/6 or HLA-A2$^+$ (or HLA-A2$^+$-RAG$^{-/-}$) mice respectively. After 9 days of tumor establishment, recipient mice were injected (i.p) with cyclophosphamide (4 mg/mice) before adoptively transferring (i.v) either h3T (CD4$^+$Vβ12$^+$) or TRP-1 (CD4$^+$Vβ14$^+$) Th1, Th17, Th1/17 cells on day 10. Similarly, Pmel (CD8$^+$Vβ13$^+$) and TCR-I (CD8$^+$Sv40 antigen specific) Tc1, Tc17 and Tc1/17 cells were adoptively transferred (i.v) into either 9 days established B16-F10 tumor bearing mice or TRAMP (spontaneously develop prostate tumor) respectively. For in vivo neutralization of IFNγ and IL17, neutralizing antibody to IFNγ and IL17 or matched isotype antibody was injected (100 µg/mouse; i.p.) in tumor bearing mice following adoptive transfer of T cells. In some experiments, tumor bearing mice received anti-CD38 antibody (50 µg/mouse; i.p.) after adoptive TRP-1 Th0 cells transfer. Recipient mice were given IL2 (50,000 U/mouse; i.p) for 3 consecutive days after ACT.

Flow cytometry: Staining for cell surface markers was performed by incubating cells with antibody at 1:200 dilutions in FACS buffer (0.1% BSA in PBS) for 30 min at 4° C. For intracellular cytokine staining of IFNγ and IL17a, surface markers were stained before fixation/permeabilization (BD Cytofix/Cytoperm Kit, BD Biosciences, San Jose, CA). For staining of transcription factors (T-bet, RORγ, IRF-4) and PGC1α cells were stained with surface markers and fixed/permeabilized with FoxP3 staining buffer set (eBioscience, San Diego, CA). For pFoxo1 staining, cells were fixed/permeabilized using BD perm III buffer set (BD Bioscience, San Jose, CA) before staining with cell surface markers and pFoxo1 primary antibody (Cell Signaling Technologies, Danvers, MA) followed by fluorochrome conjugated secondary antibody (Jackson ImmunoResearch Laboratories, West Grove, PA). Samples were acquired on LSRFortessa and analysed with FlowJo software (Tree Star, OR).

Real-time quantitative-PCR: Total RNA was extracted from pellets of the indicated T cell subsets ($2 \times 10^6$ cells) using Trizol reagent (Life technologies, Grand Island, NY). cDNA was generated from 1 µg total RNA using iScript cDNA Synthesis Kit (BioRad, Hercules, CA). SYBR Green incorporation quantitative real-time PCR was performed using a SYBR Green mix (Biorad, Hercules, CA) in the CFX96 Detection System (BioRad, Hercules, CA). Expression of different genes was quantified relative to Actb.

Transmission Electron Microscopy (TEM): The cells were pelletized and fixed in 2% Phosphate Buffered Glutaraldehyde for 1 hr. The pellets were rinsed in 0.1M Phosphate Buffered Rinse and then post fixed in 2% Aqueous Osmium Tetroxide for 1 hr. After rinsing in distilled water the pellets were dehydrated through a series of graded Ethyl Alcohol; 50% ETOH for 15 min, 70% ETOH for 15 min, 95% ETOH for 15 min and finally twice with 100% ETOH for 15 min each. The dehydrant was removed using the intermediate fluid, Propylene Oxide, 1 changes of 10 min each. The pellets were infiltrated with a 1:1 solution of propylene oxide and Embed 812 (Electron Microscopy Sciences, Ft. Washington, PA) for 1 hr. The infiltration was continued using a 1:2 solution of propylene oxide and Embed 812, overnight. The pellets were embedded in Embed812 the following day and polymerized in a 60° C. oven for 48 hr. Preliminary ½ micron sections were cut and stained with Toluidine Blue and examined using a light microscope. Then with the cell types identified the 70 nm thin sections are cut and stained with uranyl acetate and led citrate, allowed to dry. The sections are view on the JEOL 1010 and images are taken with a Hamamatsu electron microscope camera.

Immunoblotting and Immunoprecipitation of Foxo1: For evaluation of global protein acetylation, cells were lysed using NE-PER Nuclear and Cytoplasmic Extraction Reagents (Thermo Fisher Scientific, Waltham, MA) and nuclear fraction was isolated according to the manufacturer's protocol. Equal amounts of nuclear protein (20 µg) were separated by 4%-12% SDS-PAGE and then transferred to nitrocellulose membranes. The membranes were probed with anti-Acetyl-Lysine antibody (Cell Signaling Technologies, Danvers, MA) followed by incubation with secondary antibody (HRP-conjugated goat anti-rabbit IgG at 1:3000 dilutions) for overnight at 4° C. Pre-stained molecular weight and magic markers were run in parallel to identify the molecular weight of proteins. For chemiluminescent detection, the membranes were treated with enhanced chemiluminescent reagent, and the signal was monitored using a Biorad Versadoc imaging system (Biorad, Hercules, CA). Same membrane was stripped with stripping buffer (Bioland Scientific, Paramount, CA) according to manufacturer's protocol and re-probed with antibody specific to histone H3 (Cell Signaling Technologies, Danvers, MA) as reference control.

For evaluation of the protein level of glutamine transporters and glutaminolytic enzymes, cell pellets were washed in PBS and lysed in 80 µl RIPA buffer containing protease inhibitor cocktail. After 30 min incubation on ice cell lysates were centrifuged at 12000 g for 15 min at 4° C. Protein concentration in lysates was determined by Bradford method. For immunoblot analyses, 40 µg of protein lysates per sample were denatured in 2×SDS-PAGE sample buffer and subjected to SDS-PAGE on 10% Tris-glycine gel. The separated proteins were transferred onto PVDF membrane followed by blocking with 5% BSA (w/v) in TBS (10 mM Tris, 100 mM NaCl, 0.1% Tween 20) for 1 hr at room temperature. Membrane was probed with either anti-Slc1a5 antibody (Thermo Fisher Scientific, Waltham, MA) or x-CT (Abcam, Cambridge, MA) or Glud1 (Cell Signaling Technology, Danvers, MA) or Gls (Novus Biologicals, Littleton, CO) overnight at 4° C. followed by 1 hr incubation with HRP-conjugated secondary antibody and using a chemiluminescence kit (SuperSignal West Dura Extended Duration Substrate, Thermo Fisher Scientific, Waltham, MA).

For immunoprecipitation of Foxo1, T cells were first washed with phosphate buffer saline (PBS) and lysed in 500 µL of RIPA buffer containing a protease inhibitor cocktail for 30 min on ice. Cell lysates were centrifuged at 6000 g for 10 min. Foxo1 was isolated by immunoprecipitation using the immunoprecipitation kit (Cat #K286, BioVision, Milpitas, CA). Briefly, 500 µL of supernatant (200 µg protein) was incubated with anti-Foxo1 monoclonal antibodies (1:100 dilution) for 16 hr at 4° C. followed by incubation with Protein A/G-Sepharose for 1 hr at 4° C. The immunoprecipitate was washed multiple times with wash buffer and extracted with Tris-Glycine HCl SDS (2×) buffer and heated at 95° C. as per the manufacturer's direction. The proteins were resolved on 10% SDS-PAGE and then transferred to nitrocellulose membranes. The membranes were probed with anti-Acetyl-Lysine antibodies followed by incubation with secondary antibodies (HRP-conjugated goat anti-rabbit IgG at 1:3000 dilution) for 1 hr at 20° C. Pre-stained molecular weight and magic markers were run in parallel to identify the molecular weight of proteins of interest. For chemiluminescent detection, the membranes were treated with enhanced chemiluminescent reagent, and the signal was monitored using a Biorad Versadoc imaging system (Biorad, Hercules, CA).

Metabolism Assays: Glucose uptake by ex vivo differentiated T cells were determined by incubating cells with 100 µM 2NBDG (Cayman chemical, Ann Arbor, MI) for 30 min before measuring fluorescence by flow cytometry.

Oxygen consumption rate (OCR) and Extracellular acidification rate (ECAR) was determined using Seahorse Xfe96 analyser (Agilent Technologies, Santa Clara, CA). Briefly, T cells ($0.5 \times 10^6$/well) were plated on Cell-Tak coated Seahorse culture plate for 30 min. OCR, a measure of OXPHOS, was analysed under basal condition or in response to 200 µM Etomoxir (Sigma-Aldrich, St. Louis, MO) followed by 1.0 µM oligomycin (Sigma-Aldrich, St. Louis, MO), 1.0 µM fluoro-carbonyl cyanide phenylhydrazone (FCCP) (Sigma-Aldrich, St. Louis, MO) and 2 µM rotenone (Sigma-Aldrich, St. Louis, MO) plus 100 nM antimycin A (Sigma-Aldrich, St. Louis, MO). ECAR, a measure of glycolysis was measured under basal conditions and in response to glucose (5.5 mM), Oligomycin (1.0 µM), 2-deoxyglucose (2-DG) (100 mM) (Sigma-Aldrich, St. Louis, MO).

Metabolomics: Intracellular level of different metabolites was determined by performing metabolomics analysis using UPHPLC/MS/MS and GC/MS platform (Metabolon Inc. Durham, NC). Data were then grouped by unsupervised clustering using MetaboAnalyst software. Samples were loaded in an equivalent manner across the platform and normalized to Bradford values prior to statistical analysis.

Glutamine uptake assay: Ex vivo programmed Th cell subsets ($1 \times 10^6$ cells) were starved in glutamine free RPMI-1640 media (Thermo Fisher Scientific, Cat #21870-076) for 15 min before incubated with L-2,3,4-[$^3$H] glutamine (0.5 mCi, PerkinElmer) for 10 min at room temperature. Cells were lysed in 500 µl of lysis buffer (Sigma-Aldrich, St. Louis, MO) and radioactivity was measured by liquid scintillation.

$NAD^+$, Sirt1 activity and Foxo1 activity assay: Intracellular $NAD^+$ level in T cells were measured spectrophotometrically following the manufacturer's protocol (Cayman chemical, Ann Arbor, MI). Using equal amounts of nuclear protein extracted by NE-PER Nuclear and Cytoplasmic Extraction Reagents (Thermo Fisher Scientific, Waltham, MA), Sirt1 activity (Universal Sirt1 Activity Assay Kit, Abcam, Cambridge, MA) and Foxo1 activity (FKHR transcription Factor Assay Kit, Active Motif, Carlsbad, CA) were determined as per manufacturer's protocol.

Isolation of tumor infiltrating T cells: To obtain tumor infiltrating T cells (TILs) from subcutaneously established solid B16-F10 melanoma bearing mice, tumors were excised, chopped finely using tweezers and scissors and then digested with 2 mg/ml collagenase type IV (Stemcell technologies, Vancouver, BC) for 45 min. Following digestion, tumors were filtered through 70 µM cells strainers (BD Biosciences, San Jose, CA) and layered over ficoll-paque (GE Healthcare). After centrifugation at 1200 rpm for 30 min, mononuclear cell layer containing TILs was isolated. For isolation of T cells from EL-4 tumor site, tumor was established as ascites in the peritoneal cavity for 12 days in mice and fluid was withdrawn to obtain TILs. To isolate TILs from prostate tumor sites, the resected prostate tumors were quickly minced with scalpels into small fragments (1-2 $mm^2$) in cold RPMI media with 10% FBS, after trimming away the seminal vesicles, fat and connective tissue. The fragments were then placed on a 70 µm strainer and homogenized using plunger end of a syringe (one fragment at a time to ensure complete homogenization). This process rapidly produces a single cell suspension without the requirement of enzymatic digestion. The cell suspension was washed in culture medium twice by centrifugation at 1500 rpm for 10 min at 4° C. After the second wash, the cells were re-suspended in 6 ml PBS and layered carefully over 3 ml Ficoll-paque (GE healthcare) followed by centrifugation at 1500 rpm for 30 min at room temperature. The enriched TILs obtained at the interface as a thin buffy layer, were washed with PBS twice and finally re-suspended in FACS staining buffer for further staining procedures.

Activation induced T cell death: Differentiated Th1, Th17 and Th1/17 cells were re-stimulated overnight with plate bound anti-CD3 (2 µg/ml) plus anti-CD28 (1 µg/ml). Apoptosis was measured by Annexin V (BD Biosciences, San Jose, CA) vs. 7AAD staining according to the manufacturer's protocol, followed by analysis by flow cytometry. Data were analysed with FlowJo software (Tree Star, OR).

DNA Microarray Experiments: Biotinylated cRNA was prepared using the Illumina RNA Amplification Kit, Catalog #1L1791 (Ambion, Inc., Austin, TX) according to the manufacturer's specifications starting with ~250 ng total RNA. For microarray analysis, the MouseWG-6 v2.0 Expression BeadChip Kit was used (Illumina, San Diego). Hybridization of 67abelled cRNA to the BeadChip, washing and scanning were performed according to the Illumina BeadStation 500x manual. Essentially the amplified, biotin-labeled mouse cRNA samples were re-suspended in a solution of Hyb E1 buffer (Illumina) and 25% (v/v) formamide at a final concentration of 25 ng/µL. 1.5 µg of each cRNA were hybridized. Hybridization was allowed to proceed at 55° C., for 18 hours after which the bead array matrix was washed for 10 min with 1×High temperature buffer (Illumina), followed by a subsequent 10 min wash in Wash E1BC buffer. The arrays were then washed with 100% ethanol for 10 min to strip off any remaining adhesive on the chip. A 2 minute E1BC wash was performed to remove residual ethanol. The arrays were blocked for 5 min with 1% (w/v) casein-PBS (Pierce). The array signal was developed via 10 minute incubation with Streptavidin-Cy3 at a final concentration of 1 µg/mL solution of (GE Healthcare) in 1% casein-PBS blocking solution. The Expression BeadChip was washed a final time in Wash E1BC buffer for 5 min and subsequently dried via centrifugation for 4 min at a setting of 275 rcf.

The arrays were scanned on the Illumina BeadArray Reader, a confocal-type imaging system with 532 (cye3) nm laser illuminations. Image analysis and data extraction was carried out as in accordance with Illumina specifications. Preliminary data analysis and QC was carried out using the GenomeStudio software (Illumina). All array data has been deposited in the EBI ArrayExpress Database. The ArrayExpress accession E-MTAB-5237.

Analysis of microarray data: Normalization of microarray data: Expression level data from the Illumina Bead Studio software were normalized using quantile normalization as implemented in the PIMENTo package (Sasik et al., 2004). Probes whose expression level exceeds a threshold value in at least one sample are called detected. The threshold value is found by inspection from the distribution plots of (log) expression levels.

Sorting the probes according to significance: Detected probes are sorted according to their q-value, which is the smallest false discovery rate (FDR) at which the gene is called significant. FDR is the expected fraction of false positive tests among significant tests (Benjamini and Hochberg, 1995). We evaluate FDR using Significance Analysis of Microarrays (SAM) and its implementation in the official statistical package samr (Tusher et al., 2001).

Statistical analysis of pathways and gene ontology terms: Each gene ontology term or a pathway is treated simply as a set of genes. The probe list, sorted by q-value in ascending order, is translated into Entrez gene ID's and parsed so that whenever several different probes represent the same gene, only the highest-ranking probe is kept for further analysis.

The sorted list of genes is subjected to analysis using the ToppGene Suite (http://toppgene.cchmc.org), a one-stop portal for (i) gene list functional enrichment, (ii) candidate gene prioritization using either functional annotations or network analysis and (iii) identification and prioritization of novel disease candidate genes in the interactome. Functional annotation-based disease candidate gene prioritization uses a fuzzy-based similarity measure to compute the similarity between any two genes based on semantic annotations. The similarity scores from individual features are combined into an overall score using statistical meta-analysis. A P-value of each annotation of a test gene is derived by random sampling of the whole genome (Chen et al., 2009). Area-proportional Venn diagrams were created using Venny.

Heatmaps of expression levels were created using the heatmap.2 hierarchical clustering software. The colors qualitatively correspond to fold changes with respect to a reference which is calculated as the mid-point between compared groups.

Statistical analysis: All data reported are the arithmetic mean from 3 or independent experiments performed in triplicate ±SD unless stated otherwise. The unpaired Student t test was used to evaluate the significance of differences observed between groups, accepting $P<0.05$ as a threshold of significance. Data analyses were performed using the Prism software (GraphPad, San Diego, CA). Tumor size data was modeled using longitudinal linear regression with exchangeable correlation. Comparisons across groups at individual time points were made across groups using Wald tests based on linear combinations of coefficients.

Data And Software Availability: All array data has been deposited in the EBI ArrayExpress Database. The ArrayExpress accession number is E-MTAB-5237,

TABLE 5

| | Materials | |
|---|---|---|
| REAGENT or RESOURCE | SOURCE | IDENTIFIER |
| | Antibodies | |
| Anti-mouse CD3 | BioXCell | Clone: 145-2C11; Cat# BE0001-1; RRID: AB_1107634 |
| Anti-mouse CD28 | BioXCell | Clone: 37.51; Cat# BE0015-1; RRID: AB_1107624 |
| Anti-mouse IL4 | BioXCell | Clone: 11B11; Cat# BE0045; RRID: AB_1107707 |
| Anti-mouse IFNγ | BioXCell | Clone: XMG1.2; Cat# BE0055; RRID: AB_1107694 |
| CD4-PE | eBioscience | Clone: GK5.1; Cat# 12-0041-83; RRID: AB_465506 |
| T-bet-Percp/Cy5.5 | eBioscience | Clone: 4B10; Cat# 45-5825-80; RRID: AB_953657 |
| RORγ-APC | eBioscience | Clone: AFKJS-9; Cat# 17-6988-80; RRID: AB_10609207 |
| IRF-4-eFluor 660 | eBioscience | Clone: 3E4; Cat# 50-9858-80; RRID: AB_2574393 |
| CXCR3-PE | eBioscience | Clone: CXCR3-173; Cat# 12-1831-80; RRID: AB_1210734 |
| CD45.2-PE | eBioscience | Clone: 104; Cat# 12-0454-81; RRID: AB_465678 |
| CD39-PE/Cy7 | eBioscience | Clone: eBioA1 (A1); Cat# 25-0391-80; RRID: AB_1582280 |
| CD90.1-APC | eBioscience | Clone: HIS51; Cat# 17-0900-82; RRID: AB_1272252 |
| CD90.1-Pacific Blue | eBioscience | Clone: HIS51; Cat# 48-0900-80; RRID: AB_1272254 |
| EOMES-PE | eBioscience | Clone: Dan11mag; Cat# 12-4875-80; RRID: AB_1603275 |
| CD4-PE/Cy7 | Biolegend | Clone: GK5.1; Cat# 100422; RRID: AB_312707 |
| CD4-APC | Biolegend | Clone: GK5.1; Cat# 100412; RRID: AB_312697 |
| CD4-APC/Cy7 | Biolegend | Clone: GK5.1; Cat# 100414; RRID: AB_312699 |
| CD8-PE/Cy7 | Biolegend | Clone: 53-6.7; Cat# 100722; RRID: AB_312761 |
| CD8-APC | Biolegend | Clone: 53-6.7; Cat# 100712; RRID: AB_312751 |
| CD8-FITC | Biolegend | Clone: 53-6.7; Cat# 100706; RRID: AB_312745 |
| IL17-PE | Biolegend | Clone: TC11-18H10.1; Cat# 506904; RRID: AB_315464 |
| IL17-Pacific Blue | Biolegend | Clone: TC11-18H10.1; Cat# 506918; RRID: AB_893544 |
| IFNγ-PE | Biolegend | Clone: XMG1.2; Cat# 505808; RRID: AB_315402 |
| IFNγ-Alexa647 | Biolegend | Clone: XMG1.2; Cat# 505814; RRID: AB_493314 |
| T-bet-PE | Biolegend | Clone: 4B10; Cat# 644809; RRID: AB_2028583 |
| CCR5-PE | Biolegend | Clone: HM-CCR5; Cat# 107005; RRID: AB_313300 |
| CCR6-PE | Biolegend | Clone: 29-2L17; Cat# 129803; RRID: AB_1279139 |

TABLE 5-continued

Materials

| REAGENT or RESOURCE | SOURCE | IDENTIFIER |
| --- | --- | --- |
| CCR7-PE | Biolegend | Clone: 4B12; Cat# 120105; RRID: AB_389357 |
| CD73-Pacific Blue | Biolegend | Clone: Ty/11.8; Cat# 127212; RRID: AB_11219190 |
| CD38-PE | Biolegend | Clone: 90; Cat# 102707; RRID: AB_312928 |
| CD38-APC | Biolegend | Clone: 90; Cat# 102711; RRID: AB_312932 |
| CD71-PE/Cy7 | Biolegend | Clone: RI7217; Cat# 113811; RRID: AB_2203383 |
| PD1-PE | Biolegend | Clone: RMP1-30; Cat# 109103; RRID: AB_313420 |
| PD1-PE/Cy7 | Biolegend | Clone: RMP1-30; Cat# 109109; RRID: AB_572016 |
| CD98-PE | Biolegend | Clone: RL388; Cat# 128207; RRID: AB_1186107 |
| Annexin V FITC | BD Biosciences | Clone: N/A; Cat# 51-65874X; RRID: N/A |
| CD45.1-APC | BD Biosciences | Clone: A20; Cat# 558701; RRID: AB_1645214 |
| Vβ13-FITC | BD Biosciences | Clone: MR1 2-3; Cat# 553204; RRID: AB_394706 |
| Vβ14-FITC | BD Biosciences | Clone: 14-2; Cat# 553258; RRID: AB_394738 |
| Vβ12-FITC | Thermo Fisher Scientific | Clone: S511; Cat# TCR2654; RRID: AB_417092 |
| Slc1a5 | Thermo Fisher Scientific | Clone: N/A; Cat# PA5-50527; RRID: AB_2635980 |
| Anti-Goat Alexa647 | Thermo Fisher Scientific | Clone: N/A; Cat# A21447; RRID: AB_141844 |
| pFoxo1 (S256) | Cell Signaling Technology | Clone: N/A; Cat# 9461; RRID: AB_329831 |
| Phospho-S6 Ribosomal Protein (Ser235/236)- Alexa647 | Cell Signaling Technology | Clone: D57.2.2E; Cat# 4851; RRID: AB_916160 |
| Hexokinase I (HK I) | Cell Signaling Technology | Clone: C35C4; Cat# 2024S; RRID: AB_2116996 |
| Hexokinase II (HK II) | Cell Signaling Technology | Clone: C64G5; Cat# 2867S; RRID: AB_2232946 |
| Platelet-type phosphofructokinase (PFKP) | Cell Signaling Technology | Clone: D4B2; Cat# 8164S; RRID: N/A |
| Glyceraldehyde-3-phosphate dehydrogenase (GAPDH) | Cell Signaling Technology | Clone: D16H11; Cat# 5174S; RRID: AB_10622025 |
| Lactate dehydrogenase (LDH) | Cell Signaling Technology | Clone: C4B5; Cat# 3582S; RRID: AB_2066887 |
| Pyruvate kinase M 1/2 (PKM1/2) | Cell Signaling Technology | Clone: C103A3; Cat# 3190S; RRID: AB_2163695 |
| Pyruvate Dehydrogenase | Cell Signaling Technology | Clone: C54G1; Cat# 3205S; RRID: AB_2162926 |
| Glutamate Dehydrogenase 1/2 (Glud1/2) | Cell Signaling Technology | Clone: D9F7P; Cat# 12793S; RRID: N/A |
| Foxo1 | Cell Signaling Technology | Clone: C29H4; Cat# 2880S; RRID: AB_2106495 |
| Acetylated-Lysine | Cell Signaling Technology | Clone: N/A; Cat# 9441S; RRID: N/A |
| Anti-Rabbit HRP | Cell Signaling Technology | Clone: N/A; Cat# 7074S; RRID: N/A |
| PGC1α-Alexa647 | Novus Biologicals | Clone: N/A; Cat# NBP1-04676AF647; RRID: N/A |
| Glutaminase (Gls) | Novus Biologicals | Clone: N/A; Cat# NBP2-29940; RRID: N/A |
| Anti-Rabbit PE | Jackson ImmunoResearch Laboratories | Clone: N/A; Cat# 111-116-144; RRID: AB_2337985 |
| Anti-Rabbit Alexa647 | Jackson ImmunoResearch Laboratories | Clone: N/A; Cat# 111-607-003; RRID: AB_2338084 |
| xCT | Santa Cruz Biotechnology | Clone: Q-18; Cat# Sc79360; RRID: AB_2190856 |
| InVivoMab anti-mouse IL-17A | BioXCell | Clone: 17F3; Cat# BE0173; RRID: AB_10950102 |
| InVivoMAb anti-mouse IFNγ | BioXCell | Clone: XMG1.2; Cat# BE0055; RRID: AB_1107694 |
| Anti CD38 VHH Single Domain Antibody | Creative Biolabs | Clone: N/A; Cat# NABL-079; RRID: N/A |

TABLE 5-continued

Materials

| REAGENT or RESOURCE | SOURCE | IDENTIFIER |
|---|---|---|
| Chemicals, Peptides, and Recombinant Proteins | | |
| FK866 | Cayman Chemical | Cat# 13287 |
| Ex527 | Cayman Chemical | Cat# 10009798 |
| Etomoxir | Cayman Chemical | Cat# 11969 |
| AKTi | Cayman Chemical | Cat# 14870 |
| SC-79 | Sigma Aldrich | Cat# SML0749 |
| 6-Diazo-5-oxo-L-norleucine (DON) | Sigma Aldrich | Cat# D2141 |
| 2-Deoxy-D-glucose (2DG) | Sigma Aldrich | Cat# D6134 |
| Antimycin A | Sigma Aldrich | Cat# A8674 |
| Rotenone | Sigma Aldrich | Cat# R8875 |
| Oligomycin | Sigma Aldrich | Cat# O4876 |
| FCCP | Sigma Aldrich | Cat# C2920 |
| IMDM | GE Healthcare, HyClone | Cat# SH30228.01 |
| RPMI-1640 (Glucose free) | Thermo Fisher Scientific | Cat# 11879-020 |
| RPMI-1640 (glutamine free) | Thermo Fisher Scientific | Cat# 21870-076 |
| Penicillin-Streptomycin | Corning | Cat# 30-001-CI |
| Fetal Bovine Serum (FBS) | Atlanta Biologicals | Cat# S11150 |
| rIL12 | Biolegend | Cat# 577004 |
| rIL6 | Biolegend | Cat# 575704 |
| rIL1β | Biolegend | Cat# 575104 |
| rIL23 | Biolegend | Cat# 589002 |
| rTGFβ | Biolegend | Cat# 580702 |
| rhIL2 | NCI, Biological Resources Branch | https://ncifrederick.cancer.gov/research/brb/productDataSheets/cytokineHumanInterleukins/IL-2Bulk.aspx |
| Foxp3/Transcription Factor Staining Buffer Set | Thermo Fisher Scientific | Cat# 00-5523 |
| Fixation/Permeabilization Solution Kit | BD Biosciences | Cat# 554714 |
| Mouse CD4+ T cell isolation kit | Miltenyi Biotec | Cat# 130-104-454 |
| hgp100$_{25-33}$ peptide (KVPRNQDW) | Genscript | Cat# RP20344 |
| TRP-1$_{106-130}$ peptide (SGHNCGTCRPGWRGAACNQKILTVR) | NeoMPS | Custom synthesized |
| TCR-I peptide (SAINNYAQKL) | Sydlabs | Cat# 075472 |
| RIPA Lysis Buffer | Thermo Fisher Scientific | Cat# 89900 |
| NE-PER ™ Nuclear and Cytoplasmic Extraction Reagents | Thermo Fisher Scientific | Cat# 78833 |
| Critical Commercial Assays | | |
| CellTrace ™ CFSE Cell Proliferation Kit | Thermo Fisher Scientific | Cat# C34554 |
| CellTrace ™ Violet Cell Proliferation Kit | Thermo Fisher Scientific | Cat# C34557 |
| NAD/NADH Cell-Based Assay Kit | Cayman Chemical | Cat# 600480 |
| Universal SIRT Activity Assay Kit | abcam | Cat# ab156915 |
| TransAM ® FKHR (FOXO1) Transcription Factor ELISA Kits | Active Motif | Cat# 46396 |
| Akt kinase activity kit | Enzo Life Sciences | Cat# ADI-EKS-400A |
| Immunoprecipitation (IP) Kit | Biovision | Cat# K286-25 |
| iScript ™ cDNA Synthesis Kit | Biorad | Cat# 1708891 |
| SsoAdvanced ™ Universal SYBR ® Green Supermix | Biorad | Cat# 1725274 |
| Deposited Data | | |
| Gene microarray dataset | Present study | ArrayExpress accession # E-MTAB-5237 |
| Experimental Models: Cell Lines | | |
| B16-F10 | ATCC | CRL-6475 |
| B16-F10-A2+ | Rolf Kiessling, Karolinska Institute, Stockholm, Sweden. Mycoplasma | N/A |

TABLE 5-continued

| | Materials | |
|---|---|---|
| REAGENT or RESOURCE | SOURCE | IDENTIFIER |
| | testing was done in Mehrotra lab. | |
| | Experimental Models: Organisms/Strains | |
| C57BL/6 | Jackson Laboratory | Stock# 000664 |
| C57BL/6-Tg(HLA-A2.1)1Enge/J | Jackson Laboratory | Stock# 003475 |
| B6.129S7-Rag1$^{tm1Mom}$/J | Jackson Laboratory | Stock# 002216 |
| B6.129P2-Cd38$^{tm1Lnd}$/J | Jackson Laboratory | Stock# 003727 |
| B6;129-Sirt1$^{tm1Ygu}$/J | Jackson Laboratory | Stock# 008041 |
| Tg(Cd4-cre)1Cwi/BfluJ | Jackson Laboratory | Stock# 017336 |
| B6.SJL-Ptprc$^a$ Pepc$^b$/BoyJ | Jackson Laboratory | Stock# 002014 |
| B6.129S7-Ifng$^{tm1Ts}$/J | Jackson Laboratory | Stock# 002287 |
| B6.Cg-Rag1$^{tm1Mom}$ Tyrp1$^{B-w}$ Tg(Tcra, Tcrb)9Rest/J | Jackson Laboratory | Stock# 008684 |
| B6.Cg-Thy1$^a$/Cy Tg (TcraTcrb)8Rest/J | Jackson Laboratory | Stock# 005023 |
| C57BL/6-Tg(TRAMP)8247Ng/J | Jackson Laboratory | Stock# 003135 |
| IFNγ$^{Thy1.1}$ knock-in | Casey T. Weaver, University of Alabama at Birmingham (UAB) | (Harrington et al., 2008) |
| Foxo1$^{fl/fl}$Lck$^{cre}$ | Melanie Gubbels Bupp, Randolph-Macon College, VA | (Gubbels Bupp et al., 2009) |
| TCR-I | Jennifer Wu, MUSC | (Staveley-O'Carroll et al., 2003) |
| | Oligonucleotides | |
| Primers for qPCR, see Table S4 | | |
| | Recombinant DNA | |
| MSGV1-TRP-1 vector | (Kerkar et al., 2011) | N/A |
| LV-TCR/sr39TK-GFP vector | (Koya et al., 2010) | N/A |
| | Software and Algorithms | |
| FlowJo 10.2 | TreeStar, OR | https://www.flowjo.com/solutions/flowjo/downloads/ |
| Prism 5 | GraphPad | https://www.graphpad.com/scientific-software/prism/ |
| Agilent Seahorse Wave 2.4 | Agilent | http://www.agilent.com/en-us/products/cell-analysis-(seahorse)/seahorse-wave-software |
| CFX Manager 3.1 | Biorad | http://www.bio-rad.com/en-us/sku/soft-cfx-31-patch-cfx-manager-software-v3-1-upgrade |
| GenomeStudio software | Illumina | https://www.illumina.com/techniques/microarrays/array-data-analysis-experimental-design/genomestudio.html |
| PIMENTo | (Sasik et al., 2004) | github.com/MUSC-CGM/PIMENTo |
| ToppGene Suite | (Chen et al., 2009) | toppgene.cchmc.org |
| Venny | Present study | bioinfogp.cnb.csic.es/tools/venny/index.html |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 6,225,042
U.S. Pat. No. 6,355,479
U.S. Pat. No. 6,362,001
U.S. Pat. No. 6,410,319
U.S. Pat. No. 6,451,995
U.S. Pat. No. 6,790,662
U.S. Pat. No. 7,070,995
U.S. Pat. No. 7,109,304
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 8,008,449
U.S. Pat. No. 8,017,114
U.S. Pat. No. 8,119,129
U.S. Pat. No. 8,252,592
U.S. Pat. No. 8,324,353
U.S. Pat. No. 8,339,645
U.S. Pat. No. 8,354,509
U.S. Pat. No. 8,398,282
U.S. Pat. No. 8,479,118
U.S. Pat. No. 8,735,553
U.S. Patent Publication No. 2002/131960
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. 2011/0008369
U.S. Patent Publication No. 2013/0149337
U.S. Patent Publication No. 2013/287748
U.S. Patent Publication No. 2014/022021
U.S. Patent Publication No. 2014/0294898
EP2537416
WO 00/37504
WO 01/14424
WO 98/42752
WO1995/001994
WO1998/042752
WO2000/037504
WO2000/14257
WO2001014424
WO2007/103009
WO2012/129514
WO2013/071154
WO2013/123061
WO2013/126726
WO2013/166321
WO2014/031687
WO2014/055668
WO2014/055668
WO2015/016718
WO2009/114335
WO2009/101611
WO2010/027827
WO2011/066342

Bruzzone et al., *PLoS One* 4, e7897, 2009.
Camacho et al., *J Clin Oncology* 22(145): Abstract No. 2505 (antibody CP-675206), 2004.
Chang et al., *Cell* 153, 1239-1251, 2013.
Chapuis et al., *Science translational medicine* 5, 174ra127, 2013.
Chatterjee et al., *Cancer research* 74, 6048-6059, 2014.
Chini, *Curr Pharm Des* 15, 57-63, 2009.
Chothia et al., *EMBO J.* 7:3745, 1988.
Cohen et al., *J Immunol.* 175:5799-5808, 2005.
Crompton et al., *Trends in immunology* 35, 178-185, 2014.
Davila et al., *PLoS ONE* 8(4): e61338, 2013.
Deberardinis et al., *J Biol Chem* 281, 37372-37380, 2006.
Emtage et al., *Journal of immunotherapy* 26, 97-106, 2003.
Heemskerk et al., *Hum Gene Ther.* 19:496-510, 2008.
Hurwitz et al., *Proc Natl Acad Sci USA* 95(17): 10067-10071, 1998.
Janeway et al, Immunobiology: The Immune System in Health and Disease, 3$^{rd}$ Ed., Current Biology Publications, p. 4:33, 1997.
Jogl et al., *Ann N Y Acad Sci* 1033, 17-29, 2004.
Johnson et al., *Blood* 114:535-46, 2009.
Jores et al., *Pwc. Nat'lAcad. Sci. U.S.A.* 87:9138, 1990.
Klebanoff et al., *Proceedings of the National Academy of Sciences of the United States of America* 101, 1969-1974, 2004.
Klebanoff et al., *Clinical cancer research: an official journal of the American Association for Cancer Research* 17, 5343-5352, 2011.
Klysz et al., *Sci Signal* 8, ra97, 2015.
Kong et al., *Immunol Cell Biol* 90, 6-13, 2012.
Landry et al., *Proceedings of the National Academy of Sciences of the United States of America* 97, 5807-5811, 2000.
Lee, *Toxicol Res* 29, 81-86, 2013.
Lefranc et al., *Dev. Comp. Immunol.* 27:55, 2003.
Li, *Nat Biotechnol.* 23:349-354, 2005.
Lord et al., *Blood* 106, 3432-3439, 2005.
Lu et al., *The Journal of clinical investigation* 122, 4160-4171, 2012.
Mehrotra et al., *Journal of immunology* 189, 1627-1638, 2012.
Mellman et al., *Nature* 480:480-489, 2011.
Mokyr et al. *Cancer Res* 58:5301-5304, 1998.
Moroz et al., *Journal of immunology* 173, 900-909, 2004.
Mullen et al., *Nature immunology* 3, 652-658, 2002.
Muranski et al., *Blood* 112, 362-373, 2008.
Pardoll, *Nature Rev Cancer* 12:252-264, 2012.
Parkhurst et al., *Clin Cancer Res.* 15: 169-180, 2009.
Ramsay and Zammit, *Mol Aspects Med* 25, 475-493, 2004.
Remington's Pharmaceutical Sciences 22nd edition, 2012
Rosenberg and Restifo, *Science* 348, 62-68, 2015.
Sadelain et al., Cancer Discov., 3(4): 388-398, April 2013.

Sambrook et al., *Molecular Cloning: A Laboratory Manual*, 3rd ed., Cold Spring Harbor Press, Cold Spring Harbor, N.Y. 2001.
Scharping et al., *Immunity* 45, 374-388, 2016.
Singh et al., *Cancer Research*, 68:2961-2971, 2008.
Singh et al., *Cancer Research*, 71:3516-3527, 2011.
Singh et al., *PLoS One*, 8:e64138, 2013.
Terme et al., *Cancer research* 71, 5393-5399, 2011.
Tsung et al., *Journal of immunology* 158, 3359-3365, 1997.
Tullius et al., *Nat Commun* 5, 5101, 2014.
Turtle et al., Curr. Opin. Immunol., 24(5): 633-39, October 2012.
Varela-Rohena et al., *Nat Med.* 14: 1390-1395, 2008.
Wu et al., *Cancer*, 18(2): 160-75, March, 2012.
Zhang and Kraus, *Biochim Biophys Acta* 1804, 1666-1675, 2010.

What is claimed is:

1. An ex vivo method for producing hybrid Th1/Th17 and/or Tc1/Tc17 cells comprising:
   (a) obtaining a starting population of T cells comprising CD4$^+$ and CD8$^+$ T cells; and
   (b) culturing the starting population of T cells in the presence of recombinant IL6, IL1β, IL23, TGFβ and IL-12, thereby differentiating the starting population of T cells to hybrid Th1/Th17 and/or Tc1/Tc17 cells,
   wherein the TGFβ is present at a concentration of 0.1 to 0.5 ng/mL, the IL1β, IL23, IL6, and IL12 are each present at a concentration of 5 to 30 ng/mL.

2. The method of claim 1, wherein the culture further comprises anti-CD3 and anti-CD28.

3. The method of claim 2, wherein the anti-CD3 and anti-CD28 are bound to a surface.

4. The method of claim 1, wherein the culture does not comprise exogenously added IL-2.

5. The method of claim 1, wherein the culturing is for 2 to 5 days.

6. The method of claim 1, wherein the culture further comprises anti-IL4 and/or anti-IFNα.

7. The method of claim 1, wherein the CD4$^+$ T cells are isolated from splenocytes.

8. The method of claim 1, wherein the starting population of T cells are human T cells.

9. The method of claim 1, wherein the isolation is performed by magnetic-bead sorting or fluorescence-activated cell sorting.

10. The method of claim 1, wherein the hybrid Th1/Th17 cells have an effector and stemness phenotype.

11. The method of claim 1, wherein the hybrid cells have increased NAD$^+$ as compared to Th17 cells.

12. The method of claim 11, wherein the increase is at least 10-fold.

13. The method of claim 11, wherein the increase is at least 30-fold.

14. The method of claim 1, wherein the hybrid Th1/Th17 cells have reduced expression of CD38 as compared to Th1 or Th17 cells;
   have at least two-fold higher Sirt1 activity as compared to Th17 cells;
   co-express elevated levels of IFNγ and IL17;
   express transcription factors T-bet, RORγ, and/or IRF-4;
   express chemokine receptors CXCR3 and/or CCR6;
   express effector genes GzmB, Tbx21, and/or GM-CSF;
   express stemness genes IL22, IL23R, TCF7, BCL6, and/or β-catenin;
   and/or exhibit increased anti-tumor activity as compared to Th1 or Th17 cells.

* * * * *

SEQUENCE LISTING

```
<160> NUMBER OF SEQ ID NOS: 92

<210> SEQ ID NO 1
<211> LENGTH: 22
<212> TYPE: DNA
<213> ORGANISM: Artificial sequence
<220> FEATURE:
<223> OTHER INFORMATION: Synthetic primer

<400> SEQUENCE: 1
cagttcggct ataacactgg tg                                              22

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
gcccccgaca gagaagatg                                                  19

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
cggaatgggg agcctttgg                                                  19

<210> SEQ ID NO 4
<211> LENGTH: 23
<212> TYPE: DNA
<213> ORGANISM: Artificial sequence
<220> FEATURE:
<223> OTHER INFORMATION: Synthetic primer

<400> SEQUENCE: 4
gccttcctta tccgtttcaa tgg                                             23

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
ggaaccgcct agaaatctcc                                                 20

<210> SEQ ID NO 6
<211> LENGTH: 20
<212> TYPE: DNA
<213> ORGANISM: Artificial sequence
<220> FEATURE:
```

```
<223> OTHER INFORMATION: Synthetic primer

<400> SEQUENCE: 6
ggagctcaac caaaaccaag                                                    20

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
tcaagctgcg cgaactttt g                                                   21

<210> SEQ ID NO 8
<211> LENGTH: 22
<212> TYPE: DNA
<213> ORGANISM: Artificial sequence
<220> FEATURE:
<223> OTHER INFORMATION: Synthetic primer

<400> SEQUENCE: 8
ggttcttgga gtagtccacc ag                                                 22

<210> SEQ ID NO 9
<211> LENGTH: 21
<212> TYPE: DNA
<213> ORGANISM: Artificial sequence
<220> FEATURE:
<223> OTHER INFORMATION: Synthetic primer

<400> SEQUENCE: 9
atgagctgcc ctatctcaag t                                                  21

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
gtcccggtgt gtgttcacag                                                    20

<210> SEQ ID NO 11
<211> LENGTH: 22
<212> TYPE: DNA
<213> ORGANISM: Artificial sequence
<220> FEATURE:
<223> OTHER INFORMATION: Synthetic primer

<400> SEQUENCE: 11
gacaagccaa ctcacaactt cc                                                 22

<210> SEQ ID NO 12
<211> LENGTH: 22
<212> TYPE: DNA
<213> ORGANISM: Artificial sequence
<220> FEATURE:
<223> OTHER INFORMATION: Synthetic primer

<400> SEQUENCE: 12
acactgtaat ttcttggacg cc                                                 22
```

```
<210> SEQ ID NO 13
<211> LENGTH: 19
<212> TYPE: DNA
<213> ORGANISM: Artificial sequence
<220> FEATURE:
<223> OTHER INFORMATION: Synthetic primer

<400> SEQUENCE: 13
cccagagccg ggtacagaa                                                   19

<210> SEQ ID NO 14
<211> LENGTH: 21
<212> TYPE: DNA
<213> ORGANISM: Artificial sequence
<220> FEATURE:
<223> OTHER INFORMATION: Synthetic primer

<400> SEQUENCE: 14
gagccccacc atcacaatca c                                                21

<210> SEQ ID NO 15
<211> LENGTH: 20
<212> TYPE: DNA
<213> ORGANISM: Artificial sequence
<220> FEATURE:
<223> OTHER INFORMATION: Synthetic primer

<400> SEQUENCE: 15
aggagggcaa aggagtgttt                                                  20

<210> SEQ ID NO 16
<211> LENGTH: 20
<212> TYPE: DNA
<213> ORGANISM: Artificial sequence
<220> FEATURE:
<223> OTHER INFORMATION: Synthetic primer

<400> SEQUENCE: 16
ttggcagaaa tcttggttcc                                                  20

<210> SEQ ID NO 17
<211> LENGTH: 22
<212> TYPE: DNA
<213> ORGANISM: Artificial sequence
<220> FEATURE:
<223> OTHER INFORMATION: Synthetic primer

<400> SEQUENCE: 17
cttacatcga ctttgccaga ca                                               22

<210> SEQ ID NO 18
<211> LENGTH: 19
<212> TYPE: DNA
<213> ORGANISM: Artificial sequence
<220> FEATURE:
<223> OTHER INFORMATION: Synthetic primer

<400> SEQUENCE: 18
ctagggcgtg gctcacttt                                                   19

<210> SEQ ID NO 19
<211> LENGTH: 19
<212> TYPE: DNA
<213> ORGANISM: Artificial sequence
<220> FEATURE:
<223> OTHER INFORMATION: Synthetic primer
```

```
<400> SEQUENCE: 19
tcagtgctgg gtatgggtg                                                19

<210> SEQ ID NO 20
<211> LENGTH: 20
<212> TYPE: DNA
<213> ORGANISM: Artificial sequence
<220> FEATURE:
<223> OTHER INFORMATION: Synthetic primer

<400> SEQUENCE: 20
gctccttagt cctttcgcct                                               20

<210> SEQ ID NO 21
<211> LENGTH: 22
<212> TYPE: DNA
<213> ORGANISM: Artificial sequence
<220> FEATURE:
<223> OTHER INFORMATION: Synthetic primer

<400> SEQUENCE: 21
tctgtgcaga agagagcaat cc                                            22

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
ctgtcagacc gccatagtgt                                               20

<210> SEQ ID NO 23
<211> LENGTH: 21
<212> TYPE: DNA
<213> ORGANISM: Artificial sequence
<220> FEATURE:
<223> OTHER INFORMATION: Synthetic primer

<400> SEQUENCE: 23
agtgaagacg caggcatatc c                                             21

<210> SEQ ID NO 24
<211> LENGTH: 19
<212> TYPE: DNA
<213> ORGANISM: Artificial sequence
<220> FEATURE:
<223> OTHER INFORMATION: Synthetic primer

<400> SEQUENCE: 24
ggctccacgg tagagacga                                                19

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
aaagatctct ctggcgtgga                                               20

<210> SEQ ID NO 26
<211> LENGTH: 20
```

<212> TYPE: DNA
<213> ORGANISM: Artificial sequence
<220> FEATURE:
<223> OTHER INFORMATION: Synthetic primer

<400> SEQUENCE: 26
cttaacgctc tcctcggtgt                                            20

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
gtctgaatga aggcagtccc                                            20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
gtccgctcta ggtatcgcag                                            20

<210> SEQ ID NO 29
<211> LENGTH: 22
<212> TYPE: DNA
<213> ORGANISM: Artificial sequence
<220> FEATURE:
<223> OTHER INFORMATION: Synthetic primer

<400> SEQUENCE: 29
tgtctccagc aaagactact gt                                         22

<210> SEQ ID NO 30
<211> LENGTH: 23
<212> TYPE: DNA
<213> ORGANISM: Artificial sequence
<220> FEATURE:
<223> OTHER INFORMATION: Synthetic primer

<400> SEQUENCE: 30
gactgtactt gacaatgttg gga                                        23

<210> SEQ ID NO 31
<211> LENGTH: 19
<212> TYPE: DNA
<213> ORGANISM: Artificial sequence
<220> FEATURE:
<223> OTHER INFORMATION: Synthetic primer

<400> SEQUENCE: 31
tcacgggttt ctcctacgc                                             19

<210> SEQ ID NO 32
<211> LENGTH: 19
<212> TYPE: DNA
<213> ORGANISM: Artificial sequence
<220> FEATURE:
<223> OTHER INFORMATION: Synthetic primer

<400> SEQUENCE: 32

```
gccaaagcgg ttcacacac                                              19

<210> SEQ ID NO 33
<211> LENGTH: 21
<212> TYPE: DNA
<213> ORGANISM: Artificial sequence
<220> FEATURE:
<223> OTHER INFORMATION: Synthetic primer

<400> SEQUENCE: 33
ggacgtcttc tatctccaca a                                           21

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
actccttcaa tgatgccacc                                             20

<210> SEQ ID NO 35
<211> LENGTH: 20
<212> TYPE: DNA
<213> ORGANISM: Artificial sequence
<220> FEATURE:
<223> OTHER INFORMATION: Synthetic primer

<400> SEQUENCE: 35
tgcaaccaag aactcagagc                                             20

<210> SEQ ID NO 36
<211> LENGTH: 20
<212> TYPE: DNA
<213> ORGANISM: Artificial sequence
<220> FEATURE:
<223> OTHER INFORMATION: Synthetic primer

<400> SEQUENCE: 36
tcattttgga cctcactccc                                             20

<210> SEQ ID NO 37
<211> LENGTH: 20
<212> TYPE: DNA
<213> ORGANISM: Artificial sequence
<220> FEATURE:
<223> OTHER INFORMATION: Synthetic primer

<400> SEQUENCE: 37
acagctgtga ggagcagcac                                             20

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
tcttcgccac ctacttgctc                                             20

<210> SEQ ID NO 39
<211> LENGTH: 19
<212> TYPE: DNA
<213> ORGANISM: Artificial sequence
```

<220> FEATURE:
<223> OTHER INFORMATION: Synthetic primer

<400> SEQUENCE: 39
gccaacgcct gcaaaatcc                                            19

<210> SEQ ID NO 40
<211> LENGTH: 20
<212> TYPE: DNA
<213> ORGANISM: Artificial sequence
<220> FEATURE:
<223> OTHER INFORMATION: Synthetic primer

<400> SEQUENCE: 40
gcccaacggg tatgagctat                                           20

<210> SEQ ID NO 41
<211> LENGTH: 23
<212> TYPE: DNA
<213> ORGANISM: Artificial sequence
<220> FEATURE:
<223> OTHER INFORMATION: Synthetic primer

<400> SEQUENCE: 41
tgatgggaat aaccacgaag tca                                       23

<210> SEQ ID NO 42
<211> LENGTH: 22
<212> TYPE: DNA
<213> ORGANISM: Artificial sequence
<220> FEATURE:
<223> OTHER INFORMATION: Synthetic primer

<400> SEQUENCE: 42
cgaagtgtgt ctcaaactcc ac                                        22

<210> SEQ ID NO 43
<211> LENGTH: 21
<212> TYPE: DNA
<213> ORGANISM: Artificial sequence
<220> FEATURE:
<223> OTHER INFORMATION: Synthetic primer

<400> SEQUENCE: 43
gggagtgcag tgcctaaatt c                                         21

<210> SEQ ID NO 44
<211> LENGTH: 22
<212> TYPE: DNA
<213> ORGANISM: Artificial sequence
<220> FEATURE:
<223> OTHER INFORMATION: Synthetic primer

<400> SEQUENCE: 44
gtacctcgta tgtccgattc ca                                        22

<210> SEQ ID NO 45
<211> LENGTH: 22
<212> TYPE: DNA
<213> ORGANISM: Artificial sequence
<220> FEATURE:
<223> OTHER INFORMATION: Synthetic primer

<400> SEQUENCE: 45
gctgtgctct attgaagtga ca                                        22

<210> SEQ ID NO 46
<211> LENGTH: 21
<212> TYPE: DNA
<213> ORGANISM: Artificial sequence
<220> FEATURE:
<223> OTHER INFORMATION: Synthetic primer

<400> SEQUENCE: 46
ttgggcagaa accaccatta g         21

<210> SEQ ID NO 47
<211> LENGTH: 22
<212> TYPE: DNA
<213> ORGANISM: Artificial sequence
<220> FEATURE:
<223> OTHER INFORMATION: Synthetic primer

<400> SEQUENCE: 47
tgcatatagt ggagatgtct cg        22

<210> SEQ ID NO 48
<211> LENGTH: 22
<212> TYPE: DNA
<213> ORGANISM: Artificial sequence
<220> FEATURE:
<223> OTHER INFORMATION: Synthetic primer

<400> SEQUENCE: 48
gctccatatc catggccgac aa        22

<210> SEQ ID NO 49
<211> LENGTH: 22
<212> TYPE: DNA
<213> ORGANISM: Artificial sequence
<220> FEATURE:
<223> OTHER INFORMATION: Synthetic primer

<400> SEQUENCE: 49
cccaacttct tcaagatggt gg        22

<210> SEQ ID NO 50
<211> LENGTH: 21
<212> TYPE: DNA
<213> ORGANISM: Artificial sequence
<220> FEATURE:
<223> OTHER INFORMATION: Synthetic primer

<400> SEQUENCE: 50
agaggctcaa cacatggttg c         21

<210> SEQ ID NO 51
<211> LENGTH: 21
<212> TYPE: DNA
<213> ORGANISM: Artificial sequence
<220> FEATURE:
<223> OTHER INFORMATION: Synthetic primer

<400> SEQUENCE: 51
accgcacaga tgaatctcag c         21

<210> SEQ ID NO 52
<211> LENGTH: 19
<212> TYPE: DNA
<213> ORGANISM: Artificial sequence
<220> FEATURE:
<223> OTHER INFORMATION: Synthetic primer

<400> SEQUENCE: 52
atgggcaggt actcgtggt                                                  19

<210> SEQ ID NO 53
<211> LENGTH: 21
<212> TYPE: DNA
<213> ORGANISM: Artificial sequence
<220> FEATURE:
<223> OTHER INFORMATION: Synthetic primer

<400> SEQUENCE: 53
tgggcgagaa caatgaagtg t                                               21

<210> SEQ ID NO 54
<211> LENGTH: 19
<212> TYPE: DNA
<213> ORGANISM: Artificial sequence
<220> FEATURE:
<223> OTHER INFORMATION: Synthetic primer

<400> SEQUENCE: 54
cccaggatgg tttgggcag                                                  19

<210> SEQ ID NO 55
<211> LENGTH: 23
<212> TYPE: DNA
<213> ORGANISM: Artificial sequence
<220> FEATURE:
<223> OTHER INFORMATION: Synthetic primer

<400> SEQUENCE: 55
tgccacccaa agatcataga tgc                                             23

<210> SEQ ID NO 56
<211> LENGTH: 23
<212> TYPE: DNA
<213> ORGANISM: Artificial sequence
<220> FEATURE:
<223> OTHER INFORMATION: Synthetic primer

<400> SEQUENCE: 56
tgtactcctc gtattcacca agg                                             23

<210> SEQ ID NO 57
<211> LENGTH: 20
<212> TYPE: DNA
<213> ORGANISM: Artificial sequence
<220> FEATURE:
<223> OTHER INFORMATION: Synthetic primer

<400> SEQUENCE: 57
ctcagcgagc ctatcttgcc                                                 20

<210> SEQ ID NO 58
<211> LENGTH: 22
<212> TYPE: DNA
<213> ORGANISM: Artificial sequence
<220> FEATURE:
<223> OTHER INFORMATION: Synthetic primer

<400> SEQUENCE: 58
cacgttgttt aggtcctcat cc                                              22

<210> SEQ ID NO 59

```
<211> LENGTH: 20
<212> TYPE: DNA
<213> ORGANISM: Artificial sequence
<220> FEATURE:
<223> OTHER INFORMATION: Synthetic primer

<400> SEQUENCE: 59
gtctctctcc agctagccca                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic primer

<400> SEQUENCE: 60
caaacaggag ctgatgtcca                                               20

<210> SEQ ID NO 61
<211> LENGTH: 16
<212> TYPE: DNA
<213> ORGANISM: Artificial sequence
<220> FEATURE:
<223> OTHER INFORMATION: Synthetic primer

<400> SEQUENCE: 61
tctatgaggg ctcgcg                                                   16

<210> SEQ ID NO 62
<211> LENGTH: 16
<212> TYPE: DNA
<213> ORGANISM: Artificial sequence
<220> FEATURE:
<223> OTHER INFORMATION: Synthetic primer

<400> SEQUENCE: 62
cgtcagggtt gtagca                                                   16

<210> SEQ ID NO 63
<211> LENGTH: 20
<212> TYPE: DNA
<213> ORGANISM: Artificial sequence
<220> FEATURE:
<223> OTHER INFORMATION: Synthetic primer

<400> SEQUENCE: 63
tgaggaccgc tagcaagttt                                               20

<210> SEQ ID NO 64
<211> LENGTH: 20
<212> TYPE: DNA
<213> ORGANISM: Artificial sequence
<220> FEATURE:
<223> OTHER INFORMATION: Synthetic primer

<400> SEQUENCE: 64
tgtagcgacc aatcggaaat                                               20

<210> SEQ ID NO 65
<211> LENGTH: 21
<212> TYPE: DNA
<213> ORGANISM: Artificial sequence
<220> FEATURE:
<223> OTHER INFORMATION: Synthetic primer

<400> SEQUENCE: 65
```

-continued ggccttggaa gcatgtagag g                                21

<210> SEQ ID NO 66
<211> LENGTH: 23
<212> TYPE: DNA
<213> ORGANISM: Artificial sequence
<220> FEATURE:
<223> OTHER INFORMATION: Synthetic primer

<400> SEQUENCE: 66
ggagaactcg ttagagacga ctt                              23

<210> SEQ ID NO 67
<211> LENGTH: 23
<212> TYPE: DNA
<213> ORGANISM: Artificial sequence
<220> FEATURE:
<223> OTHER INFORMATION: Synthetic primer

<400> SEQUENCE: 67
ttcagatggg catgaatgtt tct                              23

<210> SEQ ID NO 68
<211> LENGTH: 23
<212> TYPE: DNA
<213> ORGANISM: Artificial sequence
<220> FEATURE:
<223> OTHER INFORMATION: Synthetic primer

<400> SEQUENCE: 68
ccaaatccga gctgttgttc tat                              23

<210> SEQ ID NO 69
<211> LENGTH: 23
<212> TYPE: DNA
<213> ORGANISM: Artificial sequence
<220> FEATURE:
<223> OTHER INFORMATION: Synthetic primer

<400> SEQUENCE: 69
atgagttttt cccttatggg gac                              23

<210> SEQ ID NO 70
<211> LENGTH: 21
<212> TYPE: DNA
<213> ORGANISM: Artificial sequence
<220> FEATURE:
<223> OTHER INFORMATION: Synthetic primer

<400> SEQUENCE: 70
gctggaagtt ggacacctca a                                21

<210> SEQ ID NO 71
<211> LENGTH: 21
<212> TYPE: DNA
<213> ORGANISM: Artificial sequence
<220> FEATURE:
<223> OTHER INFORMATION: Synthetic primer

<400> SEQUENCE: 71
gcccacaaca tcaaagaaca g                                21

<210> SEQ ID NO 72
<211> LENGTH: 21
<212> TYPE: DNA

```
<213> ORGANISM: Artificial sequence
<220> FEATURE:
<223> OTHER INFORMATION: Synthetic primer

<400> SEQUENCE: 72
aaccagccac atagcacaca t                                              21

<210> SEQ ID NO 73
<211> LENGTH: 19
<212> TYPE: DNA
<213> ORGANISM: Artificial sequence
<220> FEATURE:
<223> OTHER INFORMATION: Synthetic primer

<400> SEQUENCE: 73
agcaaggacg gcgaatgtt                                                 19

<210> SEQ ID NO 74
<211> LENGTH: 21
<212> TYPE: DNA
<213> ORGANISM: Artificial sequence
<220> FEATURE:
<223> OTHER INFORMATION: Synthetic primer

<400> SEQUENCE: 74
gggtggacat ataagcggtt c                                              21

<210> SEQ ID NO 75
<211> LENGTH: 20
<212> TYPE: DNA
<213> ORGANISM: Artificial sequence
<220> FEATURE:
<223> OTHER INFORMATION: Synthetic primer

<400> SEQUENCE: 75
gtggactgct gaaatgttcg                                                20

<210> SEQ ID NO 76
<211> LENGTH: 18
<212> TYPE: DNA
<213> ORGANISM: Artificial sequence
<220> FEATURE:
<223> OTHER INFORMATION: Synthetic primer

<400> SEQUENCE: 76
agcatccgca gcctcaac                                                  18

<210> SEQ ID NO 77
<211> LENGTH: 19
<212> TYPE: DNA
<213> ORGANISM: Artificial sequence
<220> FEATURE:
<223> OTHER INFORMATION: Synthetic primer

<400> SEQUENCE: 77
gatacagctg tcagccggg                                                 19

<210> SEQ ID NO 78
<211> LENGTH: 20
<212> TYPE: DNA
<213> ORGANISM: Artificial sequence
<220> FEATURE:
<223> OTHER INFORMATION: Synthetic primer

<400> SEQUENCE: 78
agtttctagg aaaggccgga                                                20
```

<210> SEQ ID NO 79
<211> LENGTH: 20
<212> TYPE: DNA
<213> ORGANISM: Artificial sequence
<220> FEATURE:
<223> OTHER INFORMATION: Synthetic primer

<400> SEQUENCE: 79
atggagccgg acagaaaagc                                               20

<210> SEQ ID NO 80
<211> LENGTH: 19
<212> TYPE: DNA
<213> ORGANISM: Artificial sequence
<220> FEATURE:
<223> OTHER INFORMATION: Synthetic primer

<400> SEQUENCE: 80
cttgccactc agggaagga                                                19

<210> SEQ ID NO 81
<211> LENGTH: 21
<212> TYPE: DNA
<213> ORGANISM: Artificial sequence
<220> FEATURE:
<223> OTHER INFORMATION: Synthetic primer

<400> SEQUENCE: 81
acgtagccat ccaggctggt g                                             21

<210> SEQ ID NO 82
<211> LENGTH: 18
<212> TYPE: DNA
<213> ORGANISM: Artificial sequence
<220> FEATURE:
<223> OTHER INFORMATION: Synthetic primer

<400> SEQUENCE: 82
tggcgtgagg gagagcat                                                 18

<210> SEQ ID NO 83
<211> LENGTH: 20
<212> TYPE: DNA
<213> ORGANISM: Artificial sequence
<220> FEATURE:
<223> OTHER INFORMATION: Synthetic primer

<400> SEQUENCE: 83
agagagagag ttgggggaca                                               20

<210> SEQ ID NO 84
<211> LENGTH: 20
<212> TYPE: DNA
<213> ORGANISM: Artificial sequence
<220> FEATURE:
<223> OTHER INFORMATION: Synthetic primer

<400> SEQUENCE: 84
tctgctcatg cattacccac                                               20

<210> SEQ ID NO 85
<211> LENGTH: 20
<212> TYPE: DNA
<213> ORGANISM: Artificial sequence
<220> FEATURE:

<223> OTHER INFORMATION: Synthetic primer

<400> SEQUENCE: 85
ctggcttttg tgacggaaat                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic primer

<400> SEQUENCE: 86
gtttccggca ccttcagact                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic primer

<400> SEQUENCE: 87
cactgtaagt gatgaggggg                                              20

<210> SEQ ID NO 88
<211> LENGTH: 20
<212> TYPE: DNA
<213> ORGANISM: Artificial sequence
<220> FEATURE:
<223> OTHER INFORMATION: Synthetic primer

<400> SEQUENCE: 88
tggatctctt tctccaccca                                              20

<210> SEQ ID NO 89
<211> LENGTH: 20
<212> TYPE: DNA
<213> ORGANISM: Artificial sequence
<220> FEATURE:
<223> OTHER INFORMATION: Synthetic primer

<400> SEQUENCE: 89
ctttcaccaa gggcgattta                                              20

<210> SEQ ID NO 90
<211> LENGTH: 20
<212> TYPE: DNA
<213> ORGANISM: Artificial sequence
<220> FEATURE:
<223> OTHER INFORMATION: Synthetic primer

<400> SEQUENCE: 90
ggcatttatc atttggctgg                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic primer

<400> SEQUENCE: 91
tttgctttcc ttggtcaggc                                              20

```
<210> SEQ ID NO 92
<211> LENGTH: 20
<212> TYPE: DNA
<213> ORGANISM: Artificial sequence
<220> FEATURE:
<223> OTHER INFORMATION: Synthetic primer

<400> SEQUENCE: 92
gcttgcgacc ttgaccatct                                                20
```